(12) United States Patent
Han et al.

(10) Patent No.: US 9,789,485 B2
(45) Date of Patent: Oct. 17, 2017

(54) MICRO-FLUIDIC DEVICE AND USES THEREOF

(71) Applicants: Massachusetts Institute of Technology, Cambridge, MA (US); National University of Singapore, Singapore (SG)

(72) Inventors: Jongyoon Han, Cambridge, MA (US); Chao Yu Peter Chen, Singapore (SG); Chong Jin Ong, Singapore (SG); Guofeng Guan, Singapore (SG); Ali Asgar Bhagat, Singapore (SG); Lidan Wu, Cambridge, MA (US)

(73) Assignees: Massachusetts Institute of Technology, Cambridge, MA (US); National University of Singapore, Singapore (SG)

( * ) Notice: Subject to any disclaimer, the term of this patent is extended or adjusted under 35 U.S.C. 154(b) by 72 days.

(21) Appl. No.: 14/429,280

(22) PCT Filed: Sep. 20, 2013

(86) PCT No.: PCT/SG2013/000412
§ 371 (c)(1),
(2) Date: Mar. 18, 2015

(87) PCT Pub. No.: WO2014/046621
PCT Pub. Date: Mar. 27, 2014

(65) Prior Publication Data
US 2015/0238963 A1 Aug. 27, 2015

Related U.S. Application Data

(60) Provisional application No. 61/704,128, filed on Sep. 21, 2012.

(51) Int. Cl.
*B01D 21/26* (2006.01)
*B01L 99/00* (2010.01)
(Continued)

(52) U.S. Cl.
CPC ........ *B01L 3/502753* (2013.01); *B01D 21/00* (2013.01); *B01D 21/0087* (2013.01);
(Continued)

(58) Field of Classification Search
CPC .................. B01D 21/265; B01D 21/00; B01L 2400/0463; B01L 2300/0883; B01L 2200/0652
See application file for complete search history.

(56) References Cited

U.S. PATENT DOCUMENTS 7,294,503 B2 11/2007 Quake et al.
7,309,486 B1 12/2007 Zamoyski
(Continued)

FOREIGN PATENT DOCUMENTS

JP 2007-268490 10/2007
WO WO 2007/021409 A1 2/2007
(Continued)

OTHER PUBLICATIONS

Allard, W.J., et al., "Tumor Cells Circulate in the Peripheral Blood of All Major Carcinomas but not in Healthy Subjects or Patients With Nonmalignant Diseases", *Clin. Cancer Res.*, 10: 6897-6904 (Oct. 15, 2004).
(Continued)

*Primary Examiner* — Paul Hyun
(74) *Attorney, Agent, or Firm* — Hamilton, Brook, Smith & Reynolds. P.C.

(57) ABSTRACT

A micro-fluidic device includes at least one inlet and a curvilinear microchannel having a trapezoidal cross section defined by a radially inner side, a radially outer side, a
(Continued)

bottom side, and a top side, the cross section having a) the radially inner side and the radially outer side unequal in height, or b) the radially inner side equal in height to the radially outer side, and wherein the top side has at least two continuous straight sections, each unequal in width to the bottom side.

15 Claims, 41 Drawing Sheets

(51) Int. Cl.
    *B01L 3/00*           (2006.01)
    *B01D 21/00*         (2006.01)
    *B01F 5/06*           (2006.01)
    *B03B 5/62*           (2006.01)

(52) U.S. Cl.
    CPC .......... *B01D 21/265* (2013.01); *B01F 5/0606* (2013.01); *B01L 3/50273* (2013.01); *B03B 5/62* (2013.01); *B01L 2200/0652* (2013.01); *B01L 2300/0816* (2013.01); *B01L 2300/0864* (2013.01); *B01L 2300/0883* (2013.01); *B01L 2400/0463* (2013.01); *B01L 2400/0478* (2013.01); *B01L 2400/0487* (2013.01); *B01L 2400/084* (2013.01)

(56) References Cited

U.S. PATENT DOCUMENTS

| | | | |
|---|---|---|---|
| 7,517,453 | B2 | 4/2009 | Bitensky et al. |
| 8,186,913 | B2 | 5/2012 | Toner et al. |
| 8,208,138 | B2 | 6/2012 | Papautsky et al. |
| 9,458,489 | B2 | 10/2016 | Lim et al. |
| 2007/0026381 | A1 | 2/2007 | Huang et al. |
| 2007/0131622 | A1 | 6/2007 | Oakey et al. |
| 2007/0263477 | A1* | 11/2007 | Sudarsan .......... B01F 5/0644 366/3 |
| 2007/0264675 | A1 | 11/2007 | Toner et al. |
| 2008/0128331 | A1 | 6/2008 | Lean et al. |
| 2009/0014360 | A1* | 1/2009 | Toner .......... B01D 21/0087 209/208 |
| 2009/0050538 | A1 | 2/2009 | Lean et al. |
| 2009/0053749 | A1 | 2/2009 | Manalis et al. |
| 2009/0114607 | A1 | 5/2009 | Lean et al. |
| 2009/0136982 | A1 | 5/2009 | Tang et al. |
| 2009/0283452 | A1 | 11/2009 | Lean et al. |
| 2010/0150880 | A1 | 6/2010 | Aubin et al. |
| 2010/0314323 | A1 | 12/2010 | Lean et al. |
| 2010/0314327 | A1 | 12/2010 | Lean et al. |
| 2012/0028272 | A1* | 2/2012 | Sethu .......... G01N 15/1404 435/7.1 |
| 2013/0011210 | A1 | 1/2013 | Toner et al. |
| 2013/0109011 | A1 | 5/2013 | Park et al. |
| 2013/0130226 | A1 | 5/2013 | Lim et al. |
| 2014/0093867 | A1 | 4/2014 | Burke et al. |
| 2014/0093952 | A1 | 4/2014 | Serway |
| 2014/0154795 | A1 | 6/2014 | Lipkens et al. |
| 2015/0238963 | A1 | 8/2015 | Han et al. |
| 2017/0009208 | A1 | 1/2017 | Poon et al. |

FOREIGN PATENT DOCUMENTS

| | | |
|---|---|---|
| WO | WO 2007/081902 A3 | 7/2007 |
| WO | WO 2008/130977 A2 | 10/2008 |
| WO | WO 2010/115025 A2 | 10/2010 |
| WO | WO 2011/109762 A1 | 9/2011 |
| WO | WO 2013/050445 A1 | 4/2013 |
| WO | WO 2013/116696 A1 | 8/2013 |
| WO | WO 2014/046621 A1 | 3/2014 |
| WO | WO 2015/057159 | 4/2015 |
| WO | WO 2015/126528 A1 | 8/2015 |
| WO | WO 2016/044537 | 3/2016 |
| WO | WO 2016/044555 | 3/2016 |

OTHER PUBLICATIONS

Al-Soud, W.A. et al., "Purification and Characterization of PCR-Inhibitory Components in Blood Cells", *Journal of Clinical Microbiology*, 39(2): p. 485-493 (2001).

Atkin. S.L., et al., "Hypotonic Lysis of Red Blood Cell Contamination from Human Anterior Pituitary Adenoma Cell Preparations", In Vitro Cell Dev Biol Anim, 31(9): p. 657-658 (Oct. 1995).

Bhagat AAS, et al. "Inertial microfluids for sheath-less high-throughput flow cytometry", *Biomedical Microdevices*, 12(2): 187-95 (2010).

Bhagat, A.A.S., et al., "Continuous particle separation in spiral microchannels using dean flows and differrential migration", *The Royal Society of Chemistry Lab on a Chip*, 8(11): 1906-1914 (2008).

Bhagat, A.A.S., et al., "Inertial microfluidics for continuous particle filtration and extraction", *Microfluid* Nanofluid 7: 217-226 (2009).

Bhagat, A.A.S., et al., "Pinched flow coupled shear-modulated inertial microfluidics for high-throughput rare blood cell separation", *The Royal Society of Chemistry Lab on a Chip*, 11: 1870-1878 (2011).

Bruil, A., et al., "Asymmetric membrane filters for the removal of leukocytes from blood", *Journal of Biomedical Materials Research*, 25(12): 1459-1480 (1991).

Chatterjee, A., et al., "Inertial microfluidics for continuous separation of cells and particles", Proceedings of the SPIE, vol. 7929: 10 pgs. (2011).

Cristofanilli, M., et a., "Circulating Tumor Cells, Disease Progression, and Survival in Metastatic Breast Cancer", *N. Engl. J Med.*, 351(8), 781-791 (Aug. 19, 2004).

Dean, W.R., LXXII. The stream-line motion of fluid in a curved pipe (Second Paper), *The London, Edinburgh and Dublin Philosophical Magazine and Journal of Science*, Series 7, 5:30, 673-695 (1928).

Dean, W.R., XVI. Note on the motion of fluid in a curved pipe, *The London, Edinburgh and Dublin Philosophical Magazine and Journal of Science*, Series 7, 4(20): p. 208-223 (1927).

Di Carlo D. "Inertial microfluidics", *The Royal Society of Chemistry Lab on a chip*, 9(21):3038-46 (2009).

Di Carlo, D., et al., "Continuous inertial focusing, ordering, and separation of particles in microchannels", *Proceedings of the National Academy of Sciences*, 104(48): p. 18892-18897.

DiCarlo, D., et al., "Equilibrium Separation and Filtration of Particles Using Differential Inertial Focusing", *Anal. Chem.*, 80(6): p. 2204-2211 (2008).

Downey, G.P., et al., "Retention of leukocytes in capillaries: role of cell size and deformability", *Journal of Applied Physiology*, 69(5): p. 1767-1778 (1990).

Fredriksson, K., et al., Red Blood Cells Inhibit Proliferation and Stimulate Apoptosis in Human Lung Fibroblasts In Vitro, Scandinavian Journal of Immunology, 59(6): p. 559-565 (2004).

Han, K.-H., et al., "Paramagnetic Capture mode magnetophoretic microseparator for high efficiency blood cell separations", *The Royal Society of* Chemistry, 6(2): p. 265-273 (2006).

Hou, H.W., et al., "Microfluidic Devices for Blood Fractionation", *Micromachines*, 2(3): p. 319-343 (2011).

Huang, L.R., et al., "Continuous Particle Separation Through Deterministic Lateral Displacement", *Science*, 304: 987-990 (2004).

Hur, S.C., et al., "Deformability-based cell classification and enrichment using inertial microfluidics", *The Royal Society of Chemistry, Lab on a Chip*, 11(5): 912-920 (2011).

Inglis, D.W., ct al. "Continuous microfluidic immunomagnctic cell separation", *Applied Physics Letters*, 85(21): 5093-5095 (2004).

Jaeger, BAS, et al., "Abstract P2-01-02: Circulating Tumor Cells (CTC) may Express HER2/neu in Patients With Early HER2/neu Nagative Breast Cancer—Results of the German SUCCESS C Trial", *Cancer Research*, 72(24 Suppl): Abstract nr P2-01-02 (2012).

Kuntaegowdanahalli, S.S., et al., "Inertial microfluidics for continuous particle separation in spiral microchannels", *The Royal Society of Chemistry, Lab on a Chip*, 9(20): 2973-2980 (2009).

(56) References Cited

OTHER PUBLICATIONS

Members of the Toxicogenonics Research Consortium, "Standardizing global gene expression analysis between laboratories and across platforms", *Nature Methods*, 2(5): p. 351-356 (May 2005).
Metzner, K., et al., "Abstract 3619: The absence of cleaved caspase-3 in circulating tumor cells detected using a non-enrichment based assay", *Cancer Res.*, 72, Supplement 1 (2012).
Needham, P.L., "Separation of human blood using 'Mono-Poly Resolving Medium'" *Journal of Immunological Methods*, 99: 283-284 (1986).
Notification Concerning Transmittal of International Preliminary Report on Patentability for International Application No. PCT/SG2013/000412, titled: Micro-Fluidic Device and Uses Thereof, Date of Mailing Nov. 25, 2013.
Notification of Transmittal of the International Search Report and the Written Opinion of the International Searching Authority for Int'l Application No. PCT/SG2013/000412, titled: Micro-Fluidic Device and Uses Thereof, Date of Mailing: Nov. 25, 2013.
Notification of Transmittal of the International Search Report and the Written Opinion of the International Searching Authority for Int'l Application No. PCT/US2015/000029, titled: Biophysically Sorted Osteoprogenitors From Culture Expanded Bone Marrow Derived Mesenchymal Stromal Cells (MSCs), Date of Mailing: Jun. 4, 2015.
Ookawara, S., et al., "Quasi-direct numerical simulation of lift force-induced particle separation in a curved microchannel by use of a macroscopic particle model", *Chemical Engineering Science*, 62(9): 2454-2465 (2007).
Ookawara, S., et al., Feasibility study on concentration of slurry and classification of contained particles by microchannel, *Chemical Engineering Journal*, 101(1-3): 171-178 (2004).
Panaro, N.J., et al., "Micropillar array chip for integrated white blood cell isolation and PCR", *Biomolecular Engineering*, 21(6): 157-162 (2005).
Powell, A.A., et al., "Single Cell Profiling of Circulating Tumor Cells: Transcriptional Heterogeneity and Diversity from Breast Cancer Cell Lines", *PLOS One*, 7(5): e33788, 11 pgs. (2012).
Riethdorf, S., et al., "Detection of Circulating Tumor Cells in Peripheral Blood of Patients with Metastatic Breast Cancer: A Validation Study of the CellSearch System", *Clin. Cancer Res.*, 13(3): 920-928 (2007).
Ring, A., et al. "Circulating tumour cells in breast cancer", *The lanced* Oncology, 5: 79-88 (2004).
Russom, A., et al., "Differential inertial focusing of particles in curved low-aspect-ration microchannels", *New Journal of Physics*,11: p. 075025 (2009).
Selzner, N ., et al., "Water induces autocrine stimulation of tumor cell killing through ATP release and P2 receptor binding", *Cell Death and Differentiation*, 11: p. S 172-S 180 (2004).
Seo, J., et al., Membrane-Free microfiltration by asymmetric inertial migration, *Applied Physics Letters*, 91(3): p. 033901-3 (2007).
Sethu, P., et al., "Microfluidic Isolation of Leukocytes from Whole Blood for Phenotype and Gene Expression Analysis", *Analytical Chemistry*, 78(15): 5453-5461 (2006).
Toner, M. et al., "Blood-on-a-geneip", *Annual Review of Biomedical Engineering, Annual Reviews: Palo Alto.* p. 77-103 (2005).
Yamada, M. et al., "Hydrodynamic filtration for on-chip particle concentration and classification utilizing microfluidics", *The Royal Society of Chemistry, Lab on a Chip*, 5(11): 1233-1239 (2005).
Yamada, M., et al., "Pinched Flow Fractionation: Continuous Size Separation of Particles Utilizing a Laminar Flow Profile in a Pinched Microchannel", *Analytical Chemistry*, 76(18): 5465-5471 (2004).
Zeng, L., et al., "Wall-induced forces on a rigid sphere at finite Reynolds number", *J. Fluid Mech.*, 536: 1-25 (2005).
Adams, A. A., et al., "Highly Efficient Circulating Tumor Cell Isolation from Whole Blood and Label-Free Enumeration Using Polymer-Based Microfluidics with an Integrated Conductivity Sensor," Journal of the American Chemical Society, 130(27): 8633-8641 (2008).

Al-Nbaheen, M., et al. Human stromal (mesenchymal) stem cells from bone marrow, adipose tissue and skin exhibit differences in molecular phenotype and differentiation potential. *Stem Cell Rev* 9, 32-43 (2013).
Antia, M., et al., "Microfluidic Approaches to Malaria Pathogenesis," Cellular Microbiology, 10(10): 1968-1974 (2008).
Arai, F., et al. Tie2/angiopoietin-1 signaling regulates hematopoietic stem cell quiescence in the bone marrow niche. *Cell* 118, 149-161 (2004).
Asmolov, E.S., "The Inertial Lift on a Spherical particle in a Plane Poiseuille Flow at Large Channel Reynolds Number," Journal of Fluid Mechanics, 381: 63-87 (1999).
Awaya, N., Rupert, K., Bryant, E. & Torok-Storb, B. Failure of adult marrow-derived stem cells to generate marrow stroma after successful hematopoietic stem cell transplantation. *Experimental Hematology* 30, 937-942 (2002).
Ball, L.M., et al. Cotransplantation of ex vivo expanded mesenchymal stem cells accelerates lymphocyte recovery and may reduce the risk of graft failure in haploidentical hematopoietic stem-cell transplantation. *Blood* 110, 2764-2767 (2007).
Ball, L.M., et al. Graft dysfunction and delayed immune reconstitution following haploidentical peripheral blood hematopoietic stem cell transplantation. *Bone Marrow Transplantation* 35 Suppl 1, S35-38 (2005).
Battiwalla, M. & Hematti, P. Mesenchymal stem cells in hematopoietic stem cell transplantation. *Cytotherapy* 11, 503-515 (2009).
Bhagat A.A.S., et al., "Enhancing Particle Dispersion in a Passive Planar Micromixer Using Rectangular Obstacles," Journal of Micromechanics and Microengineering. 18(8): 085005 (9 pp) (2008).
Bhagat, "Inertial Microfluidics for Particle Separation and Filteration", Ph.D. thesis, College of Engineering, University of Cincinnati, 2009.
Bhagat, A.A.S., et al., "Enhanced Particle Filtration in Straight Microchannels Using Shear-Modulated Inertial Migration," Physics of Fluids, 20: 101702 (4 pp) (2008).
Bhagat, A.A.S., et al., "Microfluidics for Cell Separation," Medical and Biological Engineering and Computing, 48: 999-1014 (2010).
Bianco, P., Riminucci, M., Gronthos, S. & Robey, P.G. Bone marrow stromal stem cells: Nature, biology, and potential applications. *Stem Cells* 19, 180-192 (2001).
Born, C., et al., "Estimation of Disruption of Animal Cells by Laminar Shear Stress," Biotechnology and Bioengineering, 40(9): p. 1004-1010 (1992).
Boxall, S.A. & Jones, E. Markers for characterization of bone marrow multipotential stromal cells. *Stem Cells Int* 2012, 975871 (2012).
Calvi, L.M., et al. Osteoblastic cells regulate the haematopoietic stem cell niche. *Nature* 425, 841-846 (2003).
Cao, X., et al. Irradiation induces bone injury by damaging bone marrow microenvironment for stem cells. *Proceedings of the National Academy of Sciences of the United States of America* 108, 1609-1614 (2011).
Chen, F.M., Zhang, M. & Wu, Z.F. Toward delivery of multiple growth factors in tissue engineering. *Biomaterials* 31, 6279-6308 (2010).
Chen, L.W., Tredget, E.E., Liu, C.X. & Wu, Y.J. Analysis of Allogenicity of Mesenchymal Stem Cells in Engraftment and Wound Healing in Mice. *Plos One* 4(2009).
Chin, C.D., et al., "Lab-On-A-Chip Devices for Global Health: Past Studies and Future Opportunities," Lab-on-a-Chip,7:41-57 (2007).
Clines, G.A., "Prospects for osteoprogenitor stem cells in fracture repair and osteoporosis", Current Opinion in Organ Transplantation, (2010), 15:(1): 73-78.
Choi, S., et al., "Microfluidic Self-Sorting of Mammalian Cells to Achieve Cell Cycle Synchrony by Hydrophoresis," Analytical chemistry,.81(5): 1964-1968 (2009).
Chun, B. et al., "Inertial Migration of Neutrally Buoyant Particles in a Square Duct: An Investigation of Multiple Equilibrium Positions", Physics of Fluids, 18(3): p. 031704 (2006).

(56) References Cited

OTHER PUBLICATIONS

Cooke, B.M., et al., "Falciparum Malaria: Sticking Up, Standing Out, and Out-Standing," Parasitology Today. 16(10): 416-420 (2000).
Cooper, S., "Rethinking Synchronization of Mammalian Cells for Cell Cycle Analysis," Cellular and Molecular Life Sciences, 60(6): 1099-1106 (2003).
Coupier, G., et al., "Noninertial Lateral Migration of Vesicles in Bounded Poiseuille Flow," Physics of Fluids. 20(11): 4 (2008).
Cranston, H.A., et al. "Plasmodium Falciparum Maturation Abolishes Physiologic Red Cell Deformability," Science. 223(4634): 400-403 (1984).
Delamarche, E., et al., "Stability of Molded Polydimethylsiloxane Microstructures," Advanced Materials, 9(9): 741-746 (1997).
Demirev, P.A., et al. "Detection of Malaria Parasites in Blood by Laser Desorption Mass Spectrometry," Analytical Chemistry. 74(14): 3262-3266 (2002).
Ding, L. & Morrison, S.J. Haematopoietic stem cells and early lymphoid progenitors occupy distinct bone marrow niches. *Nature* 495, 231-235 (2013).
Dominici, et al., *Cytotherapy* 8(4): 315-317 (2006).
Dondorp, A.M., et al., "Abnormal Blood Flow and Red Blood Cell Deformability in Severe Malaria," Parasitology Today. 16(6): 228-232 (2000).
Evans, E., et al., "Static and Dynamic Rigidities of Normal and Sickle Erythrocytes," Journal of Clinical Investigation, 73(2):477-488 (1984).
Ehninger, A. & Trumpp, A. The bone marrow stem cell niche grows up: mesenchymal stem cells and macrophages move in. *J Exp Med* 208, 421-428 (2011).
El-Badri, N.S., Wang, B.Y., Cherry & Good, R.A. Osteoblasts promote engraftment of allogeneic hematopoietic stem cells. *Experimental Hematology* 26, 110-116 (1998).
Fan, R, et al., "Integrated Barcode Chips for Rapid, Multiplexed Analysis of Proteins in Microliter Quantities of Blood," Nature Biotechnology. 26(12): 1373-1378 (2008).
Fiebig, E, et al., "Rapid Leukocyte Accumulation by "Spontaneous" Rolling and Adhesion in the Exteriorized Rabbit Mesentery," International Journal of Microcirculation Clinical and Experimental. 10(2): 127-144 (1991).
Final Office Action dated Dec. 5, 2014 for U.S. Appl. No. 13/582,263, "Microfluidics Sorter for Cell Detection and Isolation".
Final Office Action dated Oct. 16, 2015 for U.S. Appl. No. 13/582,263, "Microfluidics Sorter for Cell Detection and Isolation".
Fouillard, L., et al. Infusion of allogeneic-related HLA mismatched mesenchymal stem cells for the treatment of incomplete engraftment following autologous haematopoietic stem cell transplantation. *Leukemia* 21, 568-570 (2007).
Fujiwara, H., et al., "Red Blood Cell Motions in High-Hematocrit Blood Flowing Through a Stenosed Microchannel," Journal of Biomechanics. 42(7): 838-843 (2009).
Gascoyne, P., et al. "Microsample Preparation by Dielectrophoresis: Isolation of Malaria," Lab on a Chip 2(2): 70-75 (2002).
Gleghorn, J.P., et al., "Capture of Circulating Tumor Cells from Whole Blood of Prostate Cancer Patients Using Geometrically Enhanced Differential Immunocapture (GEDI) and a Prostate-Specific Antibody," Lab on a Chip, 10(1): 27-29 (2010).
Glenister, F.K., et al., "Contribution of Parasite Proteins to Altered Mechanical Properties of Malaria-Infected Red Blood Cells," Blood, 99(3):1060-1063 (2002).
Goldsmith, H.L., et al., "Margination of Leukocytes in Blood Flow Through Small Tubes," Microvascular Research. 27(2): 204-222 (1984).
Goldsmith, H.L., et al., "Robin Fåhraeus: Evolution of his Concepts in Cardiovascular Physiology," American Journal of Physiology. 257(3): H1005-H1015 (1989).
Gossett, D.R., et al., "Label-Free Cell Separation and Sorting in Microfluidic Systems," Anal. Bioanal. Chem., 397:3249-3267 (2010).
Gupta, A, et al., "Effect of Aspect Ratio on Inertial Migration of Neutrally Buoyant Spheres in a Rectangular Channel," 47th AIAA Aerospace Sciences Meeting, Orlando, FL (Jan. 5-8, 2009).
Granero-Molto, F., et al. Regenerative effects of transplanted mesenchymal stem cells in fracture healing. *Stem Cells* 27, 1887-1898 (2009).
Greenbaum, A., et al. CXCL12 in early mesenchymal progenitors is required for haematopoietic stem-cell maintenance. *Nature* 495, 227-230 (2013).
Guan, et al., "Spiral microchannel with rectangular and trapezoidal cross-sections for size based particle separation", *Scientific Reports*, 3:1475 (2013), 9 pages.
Hampton, R.E., et al., "Migration of Particles Undergoing Pressure-Driven Flow in a Circular Conduit," Journal of Rheology, 41(3): 621 (1997).
Han, K and A.B. Frazier, "Lateral-Driven Continuous Dielectrophoretic Microseparators for Blood Cells Suspended in a Highly Conductive Medium", The Royal Society of Chemistry, Lab on a Chip, 8(7): 1079-1086 (2008).
Heo, S.C., et al. Tumor necrosis factor-alpha-activated human adipose tissue-derived mesenchymal stem cells accelerate cutaneous wound healing through paracrine mechanisms. *J Invest Dermatol* 131, 1559-1567 (2011).
Herricks, T., et al., "Deformability Limits of Plasmodium Falciparum-Infected Red Blood Cells," Cellular Microbiology. 11(9): 1340-1353 (2009).
Ho, M., et al., "Visualization of Plasmodium Falciparum-Endothelium Interactions in Human Microvasculature: Mimicry of Leukocyte Recruitment," Journal of Experimental Medicine. 192(8): 1205-1211 (2000).
Hou, H.W., et al., "Deformability Based Cell Margination—A Simple Microfluidic Design for Malaria-Infected Erythrocyte Separation," Lab on a chip, 10(19): 2605-2613 (2010).
Hooper, A.T., et al. Engraftment and reconstitution of hematopoiesis is dependent on VEGFR2-mediated regeneration of sinusoidal endothelial cells. *Cell Stem Cell* 4, 263-274 (2009).
Horwitz, E.M. MSC: a coming of age in regenerative medicine. *Cytotherapy* 8, 194-195 (2006).
Horwitz, E.M., Maziarz, R.T. & Kebriaei, P. MSCs in hematopoietic cell transplantation. *Biol Blood Marrow Transplant* 17, S21-29 (2011).
Hou, H.W., et al., "Deformability Study of Breast Cancer Cells Using Microfluidics," Biomedical Microdevices, 11(3): p. 557-564 (2009).
Hutson, E.L., et al., "Rapid Isolation, expansion, and differentiation of osteoprogenitors from full-term umbilical cord blood", *Tissue Engineering*, 11(9-10): 1407-1420 (2005).
International Search Report and Written Opinion for PCT/SG2013/000442, entitled: "Microfluidics Sorter for Cell Detection and Isolation," dated Feb. 10, 2014.
Isolation of monomuclear cells from human cord blood by density gradient centrifugation, MACS Miltenyi Biotec (2008) 1 pg.
Itoh, S., "Bone marrow-derived HipOP cell population is markedly enriched in osteoprogenitors", *International Journal of Molecular Sciences*, 13(8): 10229-10235 (2012).
Jäggi, R.D., et al., "Microfluidic Depletion of Red Blood Cells from Whole Blood in High-Aspect-Ratio Microchannels," Microfluidics and Nanofluidics. 3(1): 47-53 (2007).
Jain, A., et al., "Determinants of Leukocyte Margination in Rectangular Microchannels," PLoS One. 4(9):e7104 (8 pp) (2009).
Jung, S., Panchalingam, K.M., Wuerth, R.D., Rosenberg, L. & Behie, L.A. Large-scale production of human mesenchymal stem cells for clinical applications. *Biotechnology and Applied Biochemistry* 59, 106-120 (2012).
Karl, S., et al., "Enhanced Detection of Gametocytes by Magnetic Deposition Microscopy predicts higher potential for Plasmodium Falciparum Transmission," Malaria Journal. 7(1): 66 (2008).
Keating, A. Mesenchymal stromal cells: new directions. *Cell Stem Cell* 10, 709-716 (2012).
Kim, U., et al., "Selection of Mammalian Cells Based on Their Cell-Cycle Phase Using Dielectrophoresis," Proceedings of the National Academy of Sciences, 104(52): 20708 (2007).

(56) References Cited

OTHER PUBLICATIONS

Kolf, C.M., Cho, E. & Tuan, R.S. Mesenchymal stromal cells—Biology of adult mesenchymal stem cells: regulation of niche, self-renewal and differentiation. *Arthritis Research & Therapy* 9(2007).
Kong, Y., et al. Association of an impaired bone marrow microenvironment with secondary poor graft function after allogeneic hematopoietic stem cell transplantation. *Biol Blood Marrow Transplant* 19, 1465-1473 (2013).
Kopp, H.G., Hooper, A.T., Avecilla, S.T. & Rafii, S. Functional heterogeneity of the bone marrow vascular niche. *Ann N Y Acad Sci* 1176, 47-54 (2009).
Lange, C., et al. Radiation rescue: mesenchymal stromal cells protect from lethal irradiation. *Plos One* 6, e14486 (2011).
Lara, O., et al., "Enrichment of Rare Cancer Cells Through Depletion of Normal Cells Using Density and Flow-Through, Immunomagnetic Cell Separation," Experimental hematology, 32(10): 891-904 (2004).
Le Blanc, K., et al. Transplantation of mesenchymal stem cells to enhance engraftment of hematopoietic stem cells. *Leukemia* 21, 1733-1738 (2007).
Lee, R.H., et al. Characterization and expression analysis of mesenchymal stem cells from human bone marrow and adipose tissue. *Cell Physiol Biochem* 14, 311-324 (2004).
Lee, S.S., et al., "Extensional Flow-Based Assessment of Red Blood Cell Deformability Using Hyperbolic Converging Microchannel," Biomedical Microdevices, (2009).
Lee, W. C., et al., "Multivariate biophysical markers predictive of mesenchymal stromal cell multipotency", *PNAS*, E4409-E4418, (2014).
Li, Z., et al. Epigenetic dysregulation in mesenchymal stem cell aging and spontaneous differentiation. *Plos One* 6, e20526 (2011).
Lincoln, B., et al., "Deformability-Based Flow Cytometry," Cytometry Part A, 59(2): 203-209 (2004).
Loffredo, F.S., Steinhauser, M.L., Gannon, J. & Lee, R.T. Bone marrow-derived cell therapy stimulates endogenous cardiomyocyte progenitors and promotes cardiac repair. *Cell Stem Cell* 8, 389-398 (2011).
Marinkovic, M., et al., "Febrile Temperature Leads to Significant Stiffening of Plasmodium Falciparum Parasitized Erythrocytes," American Journal of Physiology—Cell Physiology. 296(1):C59-C64 (2009).
Matas, J.-P., et al., "Inertial Migration of Rigid Spherical Particles in Poiseuille Flow," Journal of Fluid Mechanics, 515: 171-195 (2004).
Matas, J.P., et al., "Lateral Forces on a Sphere," Oil & Gas Science and Technology, 59(1): 59-70 (2004).
McDonald, J.C., et al., "Poly(dimethylsiloxane) as a Material for Fabricating Microfluidic Devices," Accounts of Chemical Research. 35(7): 491-499 (2002).
Migita, S., et al., "Cell Cycle and Size Sorting of Mammalian Cells Using a Microfluidic Device," Analytical Methods, 2: 657-660 (2010).
Mohamed, H., et al., "Isolation of Tumor Cells Using Size and Deformation," Journal of Chromatography A, 1216(47): 8289-8295 (2009).
Morad, V., et al. The myelopoietic supportive capacity of mesenchymal stromal cells is uncoupled from multipotency and is influenced by lineage determination and interference with glycosylation. *Stem Cells* 26, 2275-2286 (2008).
Nagrath, S., et al., "Isolation of Rare Circulating Tumour Cells in Cancer Patients by Microchip Technology," Nature, 450(7173): 1235-1239 (2007).
Nash, G.B., et al., "Abnormalities in the Mechanical Properties of Red Blood Cells Caused by Plasmodium Falciparum," Blood. 74(2): 855-861 (1989).
Naveiras, O., et al. Bone-marrow adipocytes as negative regulators of the haematopoietic microenvironment. *Nature* 460, 259-263 (2009).
Neiva, K., Sun, Y.X. & Taichman, R.S. The role of osteoblasts in regulating hematopoietic stem cell activity and tumor metastasis. *Braz J Med Biol Res* 38, 1449-1454 (2005).
Nivedita and Papautsky, *Biomicrofluidics*, 7:054101-1-14 (2013).
Non-Final Office Action dated Apr. 22, 2015 for U.S. Appl. No. 13/582,263, "Microfluidics Sorter for Cell Detection and Isolation".
Non-Final Office Action dated Mar. 26, 2014 for U.S. Appl. No. 13/582,263, "Microfluidics Sorter for Cell Detection and Isolation".
Noort, W.A., et al. Mesenchymal stem cells promote engraftment of human umbilical cord blood-derived CD34(+) cells in NOD/SCID mice. *Experimental Hematology* 30, 870-878 (2002).
Notice of Allowance and Fees Due for U.S. Appl. No. 13/582,263, "Microfluidics Sorter for Cell Detection and Isolation", dated: May 20, 2016.
Notification Concerning Transmittal of International Preliminary Report on Patentability, with International Preliminary Report on Patentability, for International Application No. PCT/US2015/000029, entitled "Biophysically Sorted Osteoprogenitors From Culture Expanded Bone Marrow Derived Mesenchymal Stromal Cells (MSCs)", Date of Mailing: Sep. 1, 2016.
Notification of Transmittal of the International Search Report and the Written Opinion of the International Searching Authority, with International Search Report and Written Opinion, with the International Search Report and the Written Opinion, for International Application No. PCT/US2015/000029, entitled "Biophysically Sorted Osteoprogenitors From Culture Expanded Bone Marrow Derived Mesenchymal Stromal Cells (MSCs)", Date of Mailing: Jun. 4, 2015.
Notification Concerning Transmittal of International Preliminary Report on Patentability for International Application No. PCT/US2011/027276, entitled: "Microfluidics Sorter for Cell Detection and Isolation," Date of Mailing: Sep. 13, 2012.
Notification of Transmittal of the International Search Report and the Written Opinion of the International Searching Authority, or the Declaration for International Application No. PCT/US2011/027276, entitled: "Microfluidics Sorter for Cell Detection and Isolation,": Date of Mailing: May 13, 2011.
Olbrich, M., et al., "Isolation of osteoprogenitors from human jaw periosteal cells: a comparison of two magnetic separation methods", *PLOS One*, 7(10): e47176 (2012).
Owen, T.A., et al., "Isolation and culture of rosent osteoprogenitor cells", *Methods in Molecular Biology*, 455, 3-18 (2008).
Park, D., et al. Endogenous bone marrow MSCs are dynamic, fate-restricted participants in bone maintenance and regeneration. *Cell Stem Cell* 10, 259-272 (2012).
Park, J.S., Yang, H.N., Woo, D.G., Jeon, S.Y. & Park, K.H. The promotion of chondrogenesis, osteogenesis, and adipogenesis of human mesenchymal stem cells by multiple growth factors incorporated into nanosphere-coated microspheres. *Biomaterials* 32, 28-38 (2011).
Paterlini-Brechot, P. and Benali, N.L.,"Circulating Tumor Cells (CTC) Detection: Clinical Impact and Future Directions," Cancer letters, 253(2): p. 180-204 (2007).
Paulitschke, M., et al., "Membrane Rigidity of Red Blood Cells Parasitized by Different Strains of Plasmodium Falciparum," Journal of Laboratory and Clinical Medicine, 122(5): 581-589 (1993).
Phinney, D.G. & Prockop, D.J. Concise review: Mesenchymal stem/multipotent stromal cells: The state of transdifferentiation and modes of tissue repair—Current views. *Stem Cells* 25, 2896-2902 (2007).
Poncin, G., et al. Characterization of spontaneous bone marrow recovery after sublethal total body irradiation: importance of the osteoblastic/adipocytic balance. *Plos One* 7, e30818 (2012).
Poon, Z., et al., "Bone Marrow Regeneration Promoted by Biophysical Sorted Osteoprogenitors from Mesenchyman Stromal Cells", *Stem Cells Translational Medicine*, 4(1): 56-65 (2015).
Popel, A.S. et al., "Microcirculation and Hemorheology," Annual Review of Fluid Mechanics. 37: 43-69 (2005).
Price, A.K., et al., "Monitoring Erythrocytes in a Microchip Channel that Narrows Uniformly: Towards an Improved Microfluidic-Based Mimic of the Microcirculation," Journal of Chromatography A, 1111(2): 220-227 (2006).

(56) References Cited

OTHER PUBLICATIONS

Pries, A.R., et al., "Biophysical Aspects of Blood Flow in the Microvasculature," Cardiovascular Research. 32(4): 654-667 (1996).

Raaijmakers, M.H., et al. Bone progenitor dysfunction induces myelodysplasia and secondary leukaemia. *Nature* 464, 852-857 (2010).

Ranganath, S.H., Levy, O., Inamdar, M.S. & Karp, J.M. Harnessing the mesenchymal stem cell secretome for the treatment of cardiovascular disease. *Cell Stem Cell* 10, 244-258 (2012).

Robey, P.G. & Termine, J.D. Human bone cells in vitro. *Calcif Tissue Int* 37, 453-460 (1985).

Rosenbluth, M.J., et al., "Force Microscopy of Nonadherent Cells: A Comparison of Leukemia Cell Deformability," Biophysical Journal, 90(8): 2994-3003 (2006).

Sacchetti, B., et al., "Self-renewing osteoprogenitors in bone marrow sinusoids can organize a hematopoietic microenvironment", *Cell*, 131(2): 324-336 (2007).

Safeukui, I., et al., "Retention of Plasmodium Falciparum Ring-Infected Erythrocytes in the Slow, Open Microcirculation of the Human Spleen," Blood. 112(6):2520-2528 (2008).

Schallmoser, K., et al. Rapid large-scale expansion of functional mesenchymal stem cells from unmanipulated bone marrow without animal serum. *Tissue Engineering Part C—Methods* 14, 185-196 (2008).

Schaff, U.Y., et al., "Vascular Mimetics Based on Microfluidics for Imaging the Leukocyte-Endothelial Inflammatory Response," Lab-on-a-Chip, 7:448-456 (2007).

Schmid-Schonbein, G.W., et al., "Morphometry of Human Leukocytes," Blood, 56(5): 866-875 (1980).

Segre, G. et al., "Behaviour of Macroscopic Rigid Spheres in Poiseuille Flow," J. Fluid Mech, 14: 115-136 (1962).

Segre, G. et al., "Radial Particle Displacements in Poiseuille Flow of Suspensions," Nature, 189: 209-210 (1961).

Sethu, P., et al., "Microfluidic Diffusive Filter for Apheresis (Leukapheresis)," Lab on a Chip, 6(1): p. 83-89 (2006).

Shelby, J.P., et al., "A Microfluidic Model for Single-Cell Capillary Obstruction by Plasmodium Falciparum-Infected Erythrocytes," Proceedings of the National Academy of Sciences of the United States of America, 100(25): 14618-14622 (2003).

Shevkoplyas, S.S., et al., "Biomimetic Autoseparation of Leukocytes from Whole Blood in a Microfluidic Device," Analytical Chemistry. 77(3): 933-937 (2005).

Shevkoplyas, S.S., et al., "Direct Measurement of the Impact of Impaired Erythrocyte Deformability on Microvascular Network Perfusion in a Microfluidic Device," Lab on a Chip. 6(7): 914-920 (2006).

Shirota, T. & Tavassoli, M. Cyclophosphamide-induced alterations of bone marrow endothelium: implications in homing of marrow cells after transplantation. *Experimental Hematology* 19, 369-373 (1991).

Stevens, D.Y., et al., "Enabling a Microfluidic Immunoassay for the Developing World by Integration of On-Card Dry Reagent Storage," Lab on a Chip. 8(12): 2038-2045 (2008).

Suresh, S., et al., "Connections Between Single-Cell Biomechanics and Human Disease States: Gastrointestinal Cancer and Malaria," Acta Biomaterialia, 1(1): 15-30 (2005).

Sutton, N., et al., "A Novel Instrument for Studying the Flow Behaviour of Erythrocytes Through Microchannels Simulating Human Blood Capillaries," Microvascular Research, 53(3): 272-281 (1997).

Taichman, R.S., Reilly, M.J. & Emerson, S.G. Human osteoblasts support human hematopoietic progenitor cells in vitro bone marrow cultures. *Blood* 87, 518-524 (1996).

Tan, S.J., et al., "Microdevice for the Isolation and Enumeration of Cancer Cells from Blood," Biomedical Microdevices, 11(4): 883-892 (2009).

Thevoz, P., et al., "Acoustophoretic Synchronization of Mammalian Cells in Microchannels," Analytical chemistry 82: 3094-3098 (2010).

Tong, X, et al., "Separation and Characterization of Red Blood Cells with Different Membrane Deformability Using Steric Field-flow Fractionation," Journal of Chromatography B: Biomedical Sciences and Applications. 674(1): 39-47 (1995).

Vona, G., et al., "Enrichment, Immunomorphological, and Genetic Characterization of Fetal Cells Circulating in Maternal Blood," American Journal of Pathology, 160(1): 51-58 (2002).

Wang, X., et al., "Progenitors systemically transplanted into neonatal mice localize to areas of active bone formation in vivo: implications of cell therapy for skeletal diseases", *Stem Cells*, 24(8): 1869-1878 (2006).

Wersto, R.P., et al., "Doublet Discrimination in DNA Cell-Cycle Analysis," Cytometry Part B: Clinical Cytometry, 46(5): 296-306 (2001).

Whitfield, M.J., et al., "Onset of heterogeneity in culture-expanded bone marrow stromal cells", *Stem Cell Research*, 11: 1365-1377 (2013).

Whitfield, M.L., et al., "Identification of Genes Periodically Expressed in the Human Cell Cycle and Their Expression in Tumors," Molecular Biology of the Cell, 2002. 13(6): 1977-2000 (2002).

Xia, Y. et al., "Soft Lithography," Annual Review of Materials Science, 28(1): 153-184 (1998).

Yang, X., Balakrishnan, I., Torok-Storb, B. & Pillai, M.M. "Marrow Stromal Cell Infusion Rescues Hematopoiesis in Lethally Irradiated Mice despite Rapid Clearance after Infusion." *Adv Hematol* 2012, 142530 (2012).

Yeh, C., et al., "Transient Lateral Transport of Platelet-Sized Particles in Flowing Blood Suspensions," Biophysical Journal, 66(5): 1706-1716 (1994).

Zabaglo, L., et al., "Cell Filtration—Laser Scanning Cytometry for the Characterisation of Circulating Breast Cancer Cells," Cytometry Part A, 55(2): 102-108 (2003).

Zeng, L., Yan, Z., Ding, S., Xu, K. & Wang, L. Endothelial injury, an intriguing effect of methotrexate and cyclophosphamide during hematopoietic stem cell transplantation in mice. *Transplant Proc* 40, 2670-2673 (2008).

Zhao, R., et al., "Micro-Flow Visualization of Red Blood Cell-Enhanced Platelet Concentration at Sudden Expansion," Annals of Biomedical Engineering. 36(7): 1130-1141 (2008).

Zheng, S., et al., "Membrane Microfilter Device for Selective Capture, Electrolysis and Genomic Analysis of Human Circulating Tumor Cells," Journal of Chromatography A, 1162(2): 154-161 (2007).

Zheng, S., et al., "Streamline-Based Microfluidic Device for Erythrocytes and Leukocytes Separation," Journal of Microelectromechanical Systems, 17(4): 1029-1038 (2008).

Zimmerman, P.A., et al., "Diagnosis of Malaria by Magnetic Deposition Microscopy," American Journal of Tropical Medicine and Hygiene. 74(4): 568-572 (2006).

Di Carlo, D., "Inertial Microfluidics," *Lab-on-a-chip*. 9(21): p. 3038-3046 (2009).

Zeng, L., et al., "Wall-Induced Forces on a Rigid Sphere at Finite Reynolds Number," *Journal of Fluid Mechanics*, 536: 1-25 (2005).

Russom, A., et al., "Differential Inertial Focusing of Particles in Curved Low-Aspect-Ratio Microchannels," New Journal of Physics, 11: 075025 (9 pp) (2009).

Notification of Transmittal of the International Search Report and the Written Opinion of the International Searching Authority, or the Declaration for International Application No. PCT/US2015/050628, entitled: "System and Method for Inertial Focusing Microfiltration for Intra-Operative Blood Salvage Autotransfusion," Date of Mailing: Dec. 21, 2015.

Notification of Transmittal of the International Search Report and the Written Opinion of the International Searching Authority, or the Declaration for International Application No. PCT/US2015/050604, entitled: "Microfluidic System and Method for Perfusion Bioreactor Cell Retention," Date of Mailing: Dec. 7, 2015.

Christopeit, M., et al. Marked improvement of severe progressive systemic sclerosis after transplantation of mesenchymal stem cells from an allogeneic haploidentical-related donor mediated by ligation of CD137L. *Leukemia* 22, 1062-1064 (2008).

\* cited by examiner

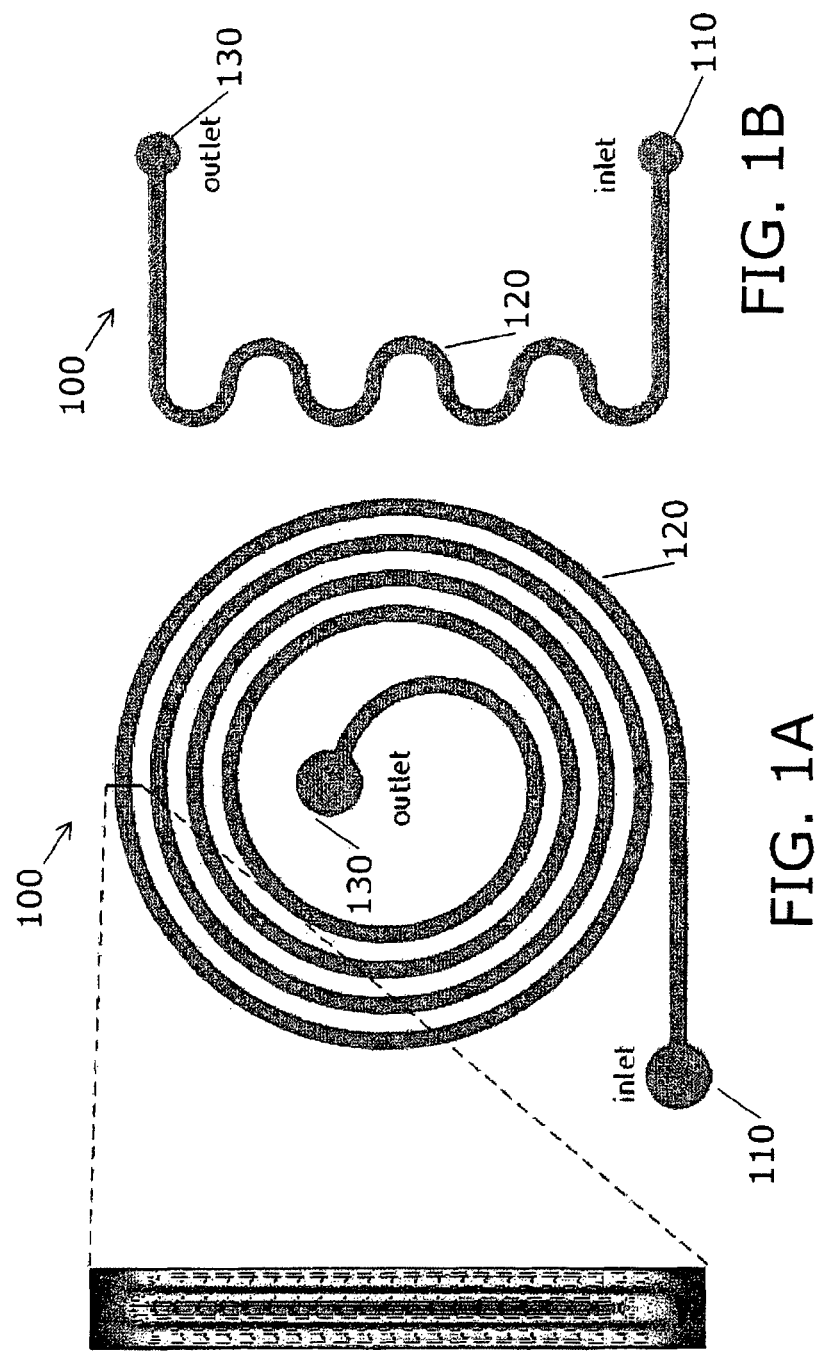

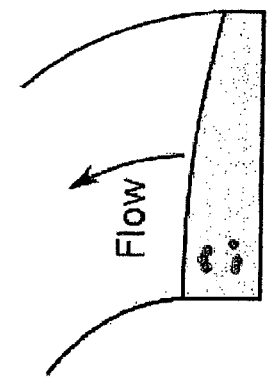
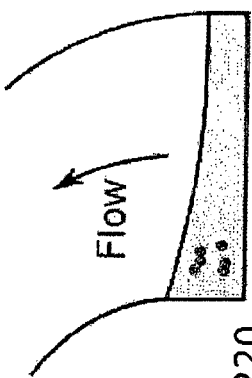
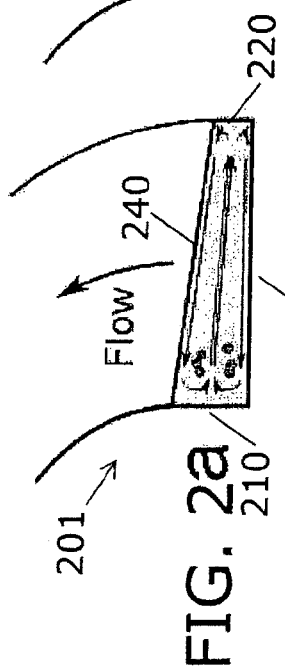
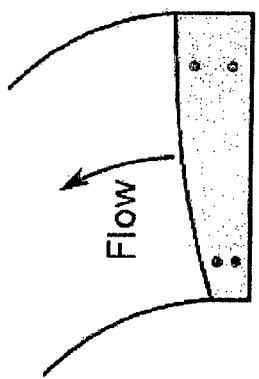
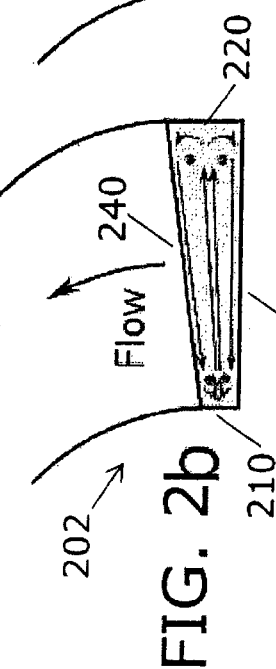
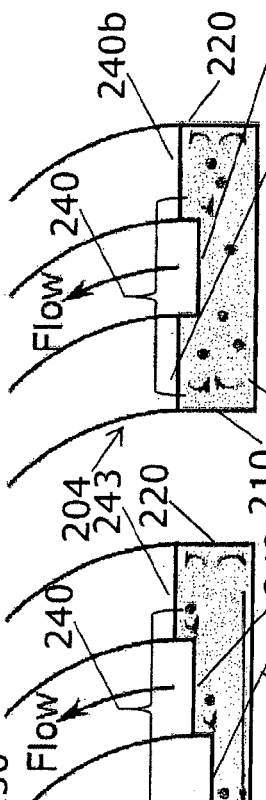
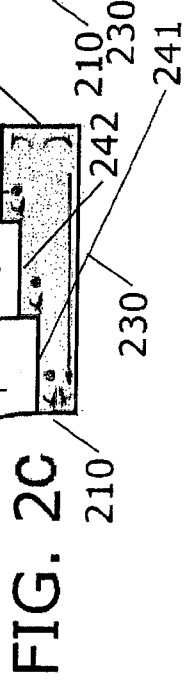
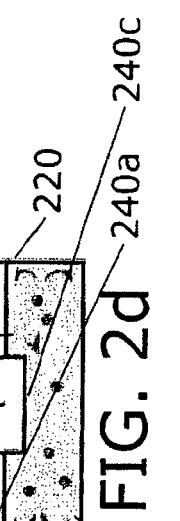

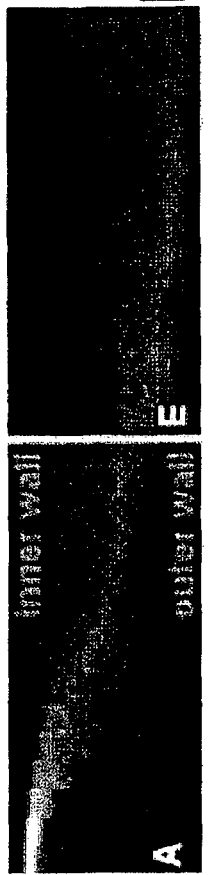
FIG. 4A
FIG. 4E
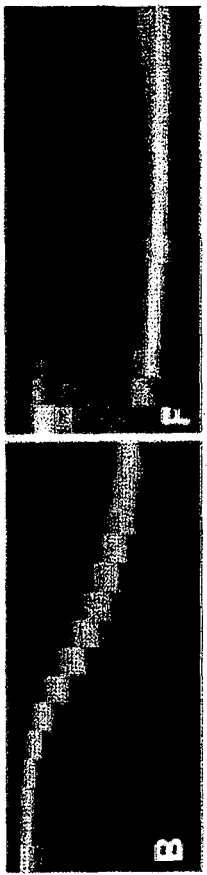
FIG. 4B
FIG. 4F
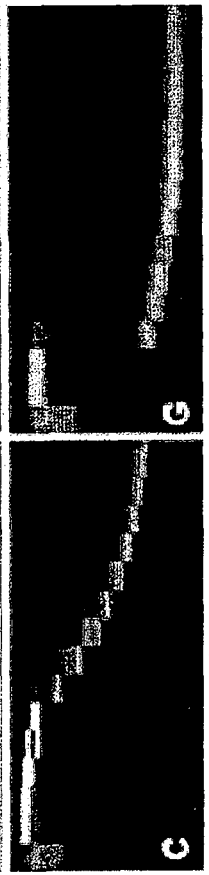
FIG. 4C
FIG. 4G
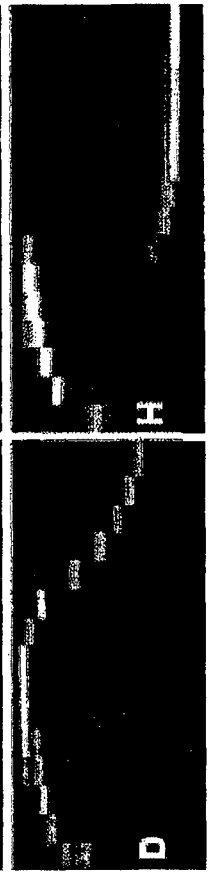
FIG. 4D
FIG. 4H

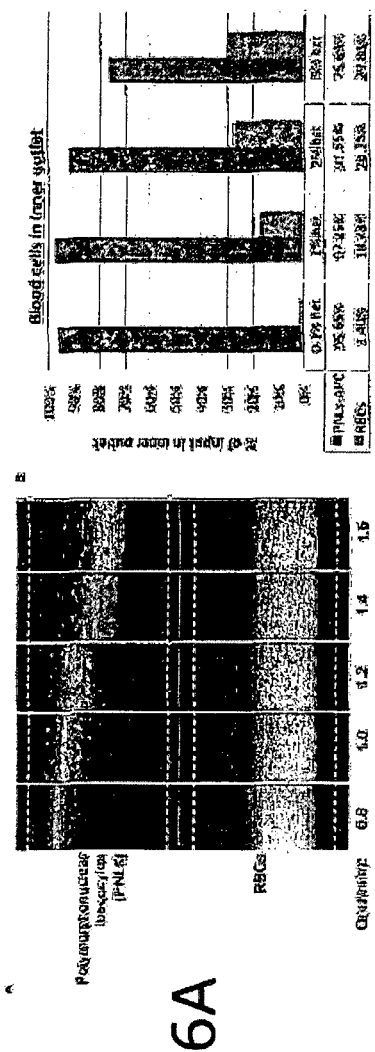
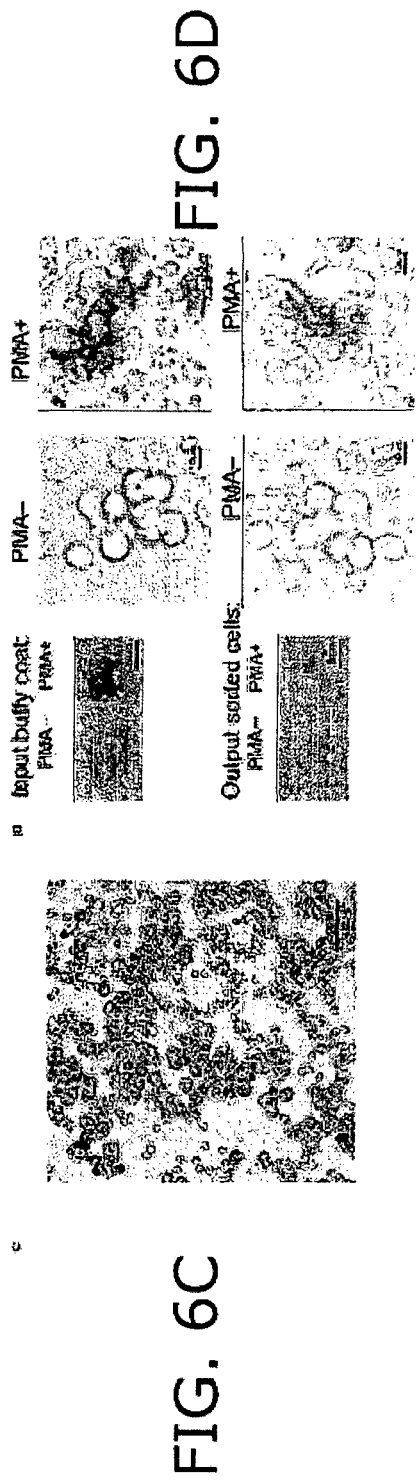
FIG. 6A
FIG. 6B
FIG. 6C
FIG. 6D

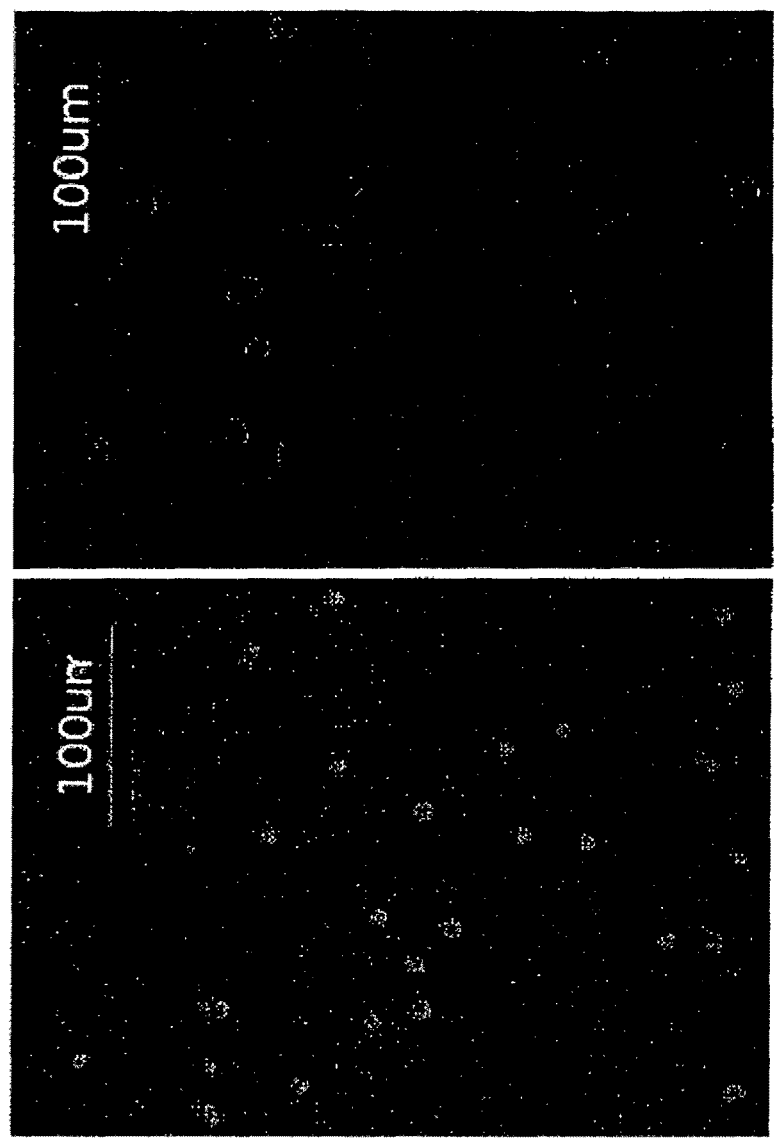

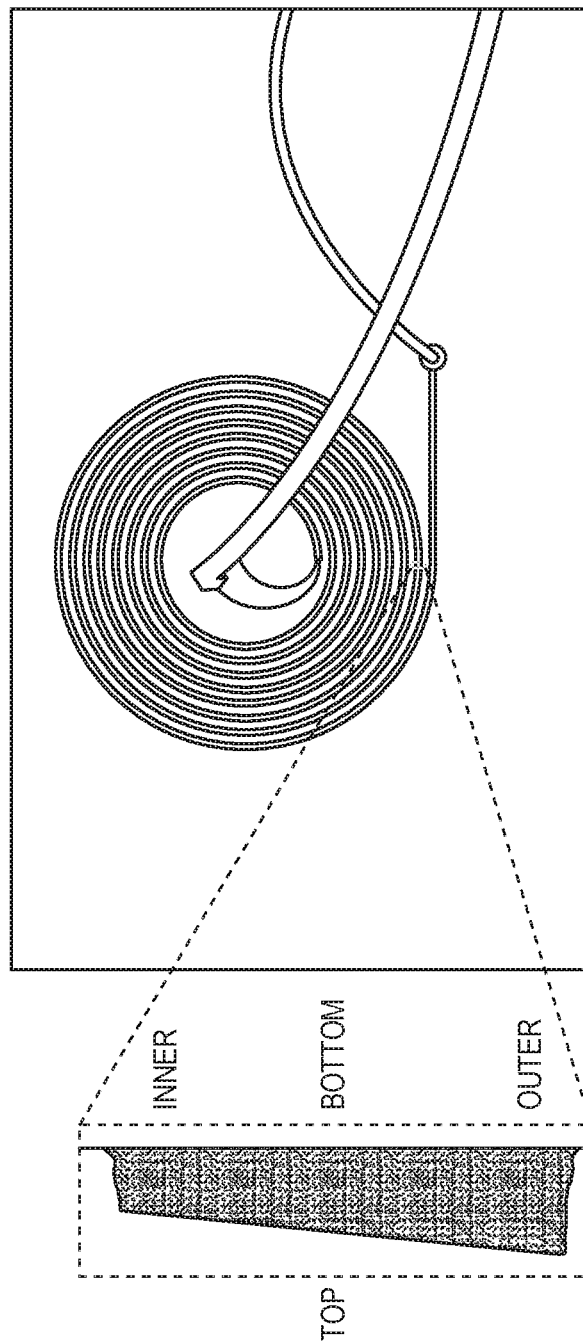

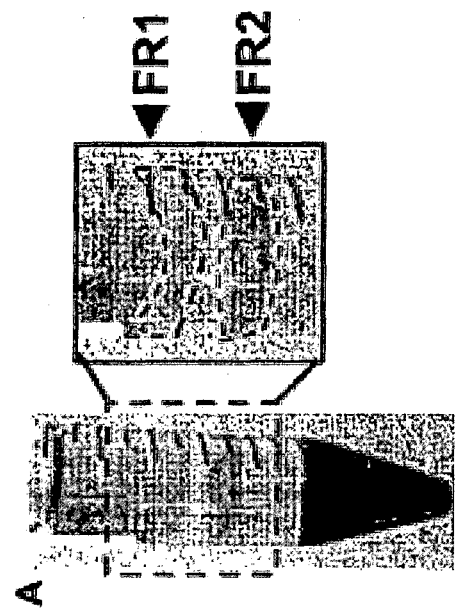
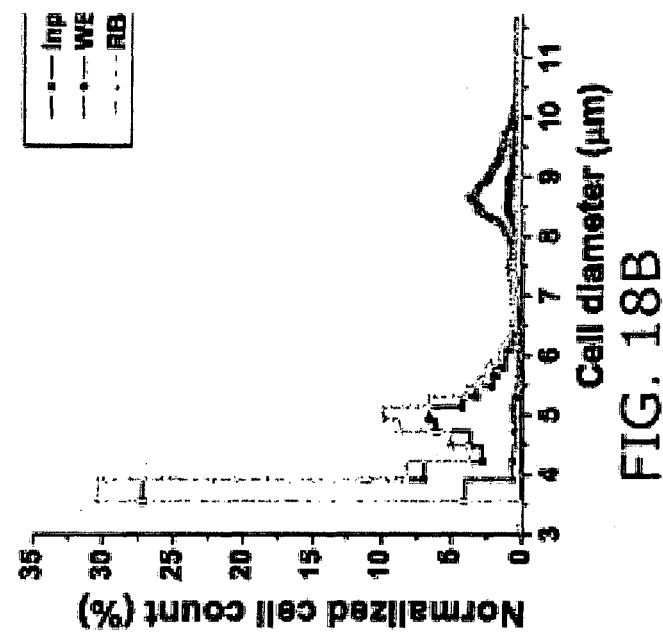
FIG. 18A
FIG. 18B

FIG. 36(A)   FIG. 36(B)
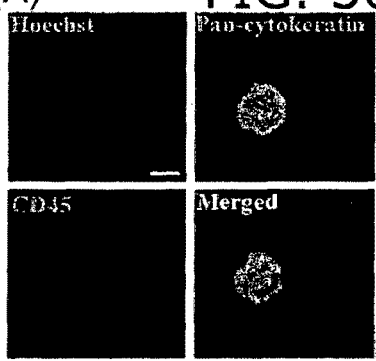
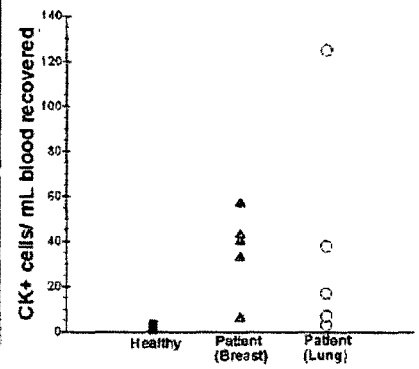
FIG. 36(C)
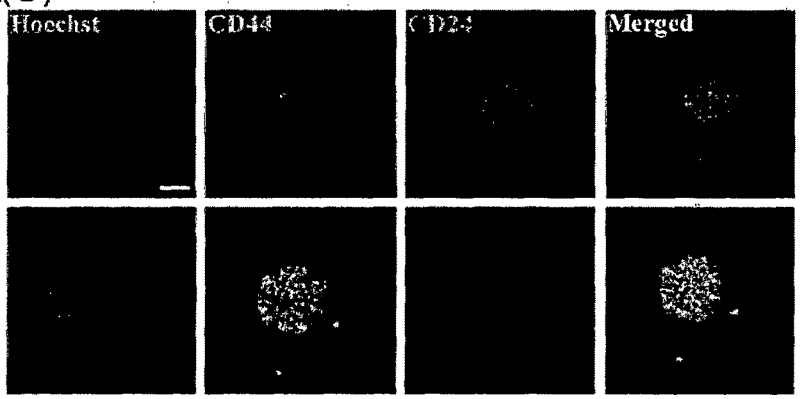
FIG. 36(D)
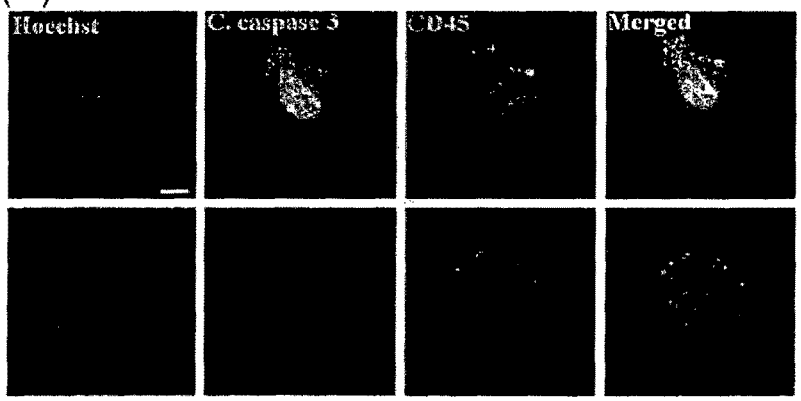

MICRO-FLUIDIC DEVICE AND USES THEREOF

RELATED APPLICATIONS

This application is the U.S. National Stage of International Application No. PCT/SG2013/000412, filed Sep. 20, 2013, which designates the U.S., published in English, and claims the benefit of U.S. Provisional Application No. 61/704,128, filed on Sep. 21, 2012. The entire teachings of these applications are incorporated herein by reference.

GOVERNMENT SUPPORT

This invention was made with government support under Grant No. N66001-11-1-4182 awarded by the Space and Naval Warfare Systems Command. The government has certain rights in this invention.

BACKGROUND OF THE INVENTION

Conventional macroscale methods for separation of cells include physical filtration using membrane-based filter and density gradient centrifugation which exploit differences in cell size, deformability, and density to filter out target cells. These techniques are labor-intensive and require multi-step sample preparations which may introduce artifacts or lead to loss of desired cells. Membrane filtration methods are also easily susceptible to clogging and require frequent cleaning. Further, evidence of mechanical stress-induced changes in original phenotype of target cells subjected to filtration and centrifugation techniques has also been reported. Recently, inertial micro-fluidic devices were explored as a filterless size-based cell fractionation method. See Di Carlo D. Inertial microfluidics. Lab on a chip. 2009; 9(21):3038-46; Kuntaegowdanahalli SS, et al. Lab on a chip. 2009; 9(20): 2973-80; Bhagat AAS, et al. Biomedical Microdevices. 2010; 12(2):187-95.

However, there is a continuing need to develop simpler and more efficient techniques to process blood samples that can minimize cell loss and maintain the original target cell phenotype for subsequent analysis.

SUMMARY OF THE INVENTION

The, invention is generally directed to micro-fluidic devices having curved micro-channels with non-rectangular cross sections for particle focusing and mixing. In a particular aspect, the invention is directed to a micro-fluidic device that includes at least one inlet and a curvilinear microchannel having a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side. The micro-fluidic device further includes at least one outlet. In certain aspects, the micro-fluidic device includes two outlets. In some aspects, the micro-fluidic device includes a single inlet.

In some aspects, the cross section of the micro-fluidic device can have (a) the height of the radially inner side larger than the height of the radially outer side, or (b) the height of the radially inner side smaller than the height of the radially outer side, or (c) the top side including at least one step forming a stepped profile, or (d) the top side including at least one shallow region in between the radially inner side and the radially outer side. The trapezoidal cross section can be a right trapezoidal cross section. In certain aspects, the top and/or bottom sides of the trapezoidal cross section can be curved, with a curvature that can be convex or concave.

In other aspects, the radially inner side and the radially outer side of the trapezoidal cross section can have a height in a range of between about 20 microns ($\mu$m) and about 200 $\mu$m. In certain aspects, the top side and the bottom side of the trapezoidal cross section can have a width in a range of between about 100 $\mu$m and about 2000 $\mu$m.

In one aspect, the curvilinear microchannel can be a spiral microchannel. In another aspect, the curvilinear microchannel can be a serpentine microchannel. The curvilinear microchannel can have a radius of curvature in a range of between about 2.5 mm and about 25 mm, and a length in a range of between about 4 cm and about 100 cm.

In yet another aspect, the invention is directed to a method of separating by size one or more particles from a mixture of particles. The method comprises introducing the mixture into at least one inlet of a micro-fluidic device that includes a curvilinear microchannel having a trapezoidal cross section defined by a radially inner side, a radially outer side, a bottom side, and a top side, the cross section having the height of the radially inner side smaller than the height of the radially outer side, at a flow rate that isolates particles along portions of the cross-section of the microchannel based on particle size, wherein larger particles flow along the radially inner side of the microchannel to a first outlet and smaller particles flow along other portions of the microchannel to at least one other outlet, thereby size separating the particles from the mixture. The method can include collecting size separated particles from the first outlet. In one aspect, the flow rate can be in a range of between about 0.5 mL/min and about 7.5 mL/min. In some aspects, the particles can be cells, such as stem cells.

In a particular aspect, the flow rate can be about 2.5 mL/min, the larger particles can have a diameter in a range of between about 18 $\mu$m and about 40 $\mu$m, and the smaller particles can have a diameter in a range of between about 10 $\mu$m and about 20 $\mu$m. In another particular aspect, the flow rate can be about 1.5 mL/min, the larger particles can have an diameter in a range of between about 15 $\mu$m and about 25 $\mu$m, and the smaller particles can have a diameter in a range of between about 5 $\mu$m and about 10 $\mu$m. In still another particular aspect, the flow rate can be in a range of between about 2.5 mL/min and about 3.0 mL/min, the larger particles can have a diameter in a range of between about 25 $\mu$m and about 40 $\mu$m, and the smaller particles can have a diameter in a range of between about 5 $\mu$m and about 15 $\mu$m.

In another aspect, the mixture of cells can be a blood sample, and the larger cells can be circulating tumor cells (CTCs), and the smaller cells can be hematologic cells. In one aspect, he flow rate can be adapted to size separate about 7.5 mL of blood in about 8 minutes. In still another aspect, the larger cells can be leukocytes, and the smaller cells can be hematologic cells. In yet another aspect, the mixture can be a bone marrow sample, wherein stem cells can be separated from hematologic cells.

In still another aspect, the invention is directed to a method of concentrating cells from a mixture. The method comprises introducing the mixture into at least one inlet of a micro-fluidic device that includes a curvilinear microchannel having a trapezoidal cross section defined by a radially inner side, a radially outer side, a bottom side, and a top side, the cross section having the height of the radially inner side larger than the height of the radially outer side, at a flow rate that isolates the cells along the radially inner side of the cross section of the microchannel and directs them to a first outlet, thereby concentrating the cells from the mixture. The method can include collecting concentrated cells from the first outlet. In particular aspects, the flow rate can be in a range of between about 0.5 mL/min and about 10 mL/min.

In yet another aspect, the invention is directed to a method of filtering particulates from a mixture. The method comprises introducing a particulate containing mixture into at least one inlet of a micro-fluidic device that includes a curvilinear microchannel having a trapezoidal cross section defined by a radially inner side, a radially outer side, a bottom side, and a top side, the cross section having the height of the radially inner side larger than the height of the radially outer side, at a flow rate that isolates particulates along the radially inner side of the cross section of the microchannel and directs them to a first outlet, thereby filtering the particulates from the mixture. In some aspects, the mixture can be water. The method can include collecting particulates from, the first outlet. In particular aspects, the flow rate can be in a range of between about 0.5 mL/min and about 10 mL/min.

In another aspect, the invention is directed to a method of distributing cells in a mixture. The method comprises introducing the mixture into at least one inlet of the micro-fluidic device that includes a curvilinear microchannel having a trapezoidal cross section defined by a radially inner side, a radially outer side, a bottom side, and a top side, the cross section having the top side that includes at least one step forming a stepped profile, at a flow rate that distributes cells along portions of the stepped profile, wherein cells do not impact the sides before, during, or after distribution to separate outlets, thereby distributing the cells in the mixture. The method can include collecting distributed cells from the separate outlets. In particular aspects, the flow rate can be in a range of between about 2 mL/min and about 10 mL/min.

In yet another aspect, the invention is directed to a method of mixing cells in a liquid. The method comprises introducing a liquid and cells into at least one inlet of the micro-fluidic device having a curvilinear microchannel having a trapezoidal cross section defined by a radially inner side, a radially outer side, a bottom side, and a top side, the cross section having the top side including at least one shallow region in between the radially inner side and the radially outer side, at a flow rate that mixes cells along the microchannel and directs the mixture to a first outlet. The method can include collecting the mixture from the first outlet. In particular aspects, the flow rate can be in a range of between about 0.1 mL/min and about 2 mL/min.

This invention has many advantages, including higher resolution separation than could be obtained with present micro-fluidic devices. The magnitude of the channel dimensions are normally >3 times the particle diameter, which not only makes the device free of clogging issues and high throughput, but also reduce the cost of fabrication. These advantages suggest a broad range of applications of curved micro-fluidic device in the future. Moreover, with the variation of channel shape, the invention described here offers many distinct advantages over traditional rectangular curved micro-channels. In particular for the application of high resolution particle separation, particles are separated into two main streams along the inner and outer side according to their diameter and the flow rate. This type of device is able to achieve high resolution, high throughput separation, which is not feasible with traditional rectangular channels.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1A and 1B are schematic illustrations showing the top-view of two typical curvilinear micro-channels (FIG. 1A: spiral, FIG. 1B: serpentine). The cutaway view of the spiral micro-channel is shown on the left. The width of the channels is typically larger than the depth. The Dean flows in a rectangular cross section channel have a main flow from inner side to outer side with the flows being parallel to the top and bottom wall. Under the influence of Dean flow and inertial lift, particles will focus at the inner half of the channel that have lower Dean flow. The positions of the particles are controlled by parameters such as channel dimensions, aspect ratio, radius of curvature, particle diameter, and flow rate.

FIGS. 2a-2d are schematic illustrations of different cross sections of curved channels: FIG. 2a) Curved micro-channels with a deeper inner side (near curvature center) and shallow outer side. The two Dean vortex cores are skewed towards the inner side, trapping particles within them. This type of micro-channel has applications in particle concentration and filtration; FIG. 2b) Curved micro-channel having a shallow inner side and a deeper outer side. The two vortex cores are skewed towards the outer side and have the ability to entrain particles of certain smaller diameter within them, which can be used for size based separation; FIG. 2c) in a curved microchannel with step-like cross-section, particles are trapped at the corners of the steps; FIG. 2d) Curved microchannels with sandwiched shallow regions create complex Dean flow and inertial lift profiles preventing particle focusing or trapping. Such channels can be used as a mixer.

FIGS. 4A-4H are top views showing the comparison of fluorescent beads distribution at the outlet of FIGS. 4A-4D) a 80 μm height 600 μm width rectangular cross section spiral microchannel, and FIGS. 4E-4H) a trapezoid cross section spiral microchannel as described in FIG. 1A with flow rates increased from 0.5 mL/min (left) to 7.5 mL/min (right). The diameters of beads shown are FIGS. 4A & 4E) 5.78 μm, FIGS. 4B & 4F) 9.77 μm, FIGS. 4C & 4G) 15.5 μm, FIGS. 4D & 4H) 26.25 μm.

FIGS. 6A-6D are results and photographs showing separation of neutrophils from fresh human blood using a spiral channel with a trapezoidal cross-section. FIG. 6A) Polymorphonuclear leukocytes (PNLs), mainly neutrophils, isolated from fresh human blood using Mono-Poly Resolving Medium (Catalog #1698049, MP Biomedicals) and 0.1% hematocrit blood sample diluted with 1× PBS were used to reveal the positions of each kind of cells inside the channel under various flow rates. The top-view images shown resulted from taking standard deviation of a series of bright-field images captured by Phantom v9.1 fast camera. The channel employed in this experiment had a trapezoidal cross-section of 500 μm in width, 90 μm and 120 μm in depth at inner or outer wall, respectively. The dashed lines on top indicate the inner channel walls, while the dashed lines on the bottom indicate the outer channel wall. FIG. 6B) Blood samples with different hematocrit were spiked with isolated PNLs, which were stained with APC-conjugated anti-CD45 antibody and used as input samples to the spiral channel at 0.8 ml/min flow rate. The recovery of PNLs and RBC cell counts in output fraction of inner outlet were determined by flow cytometry analysis and by hemocytometer, respectively. FIG. 6C) Giemsa staining for the output fraction of inner outlet when 0.1% hematocrit fresh human blood was used as input sample under 0.8 ml/min. Most of the cells were neutrophils. FIG. 6D) 1% hematocrit buffy coat of human blood were processed via the spiral under 0.8 ml/min flow rate and the nitroblue-tetrazolium (NBT) test were performed for both the input and output cells in a condition with or without 1 μM PMA. The images showed that cells turned blue only under condition of extraneous PMA, indicating that the device did not activate the neutrophils in the sample and the output neutrophils remained alive and capable of being activated by in vitro stimuli.

FIG. 7A) Sample is pumped in with 2.2 mL/min flow rate. FIG. 7B) Sample is pumped in with 3.0 mL/min flow rate.

FIGS. 8A and 8B are microscope images of MSCs collection from inner (FIG. 8B) and outer (FIG. 8A) output of 80 μm-inner,130 μm-outer and 600 μm-width trapezoid cross section spiral device at 2.5 ml/min flow rate.

FIG. 9B shows line drawings of an actual PDMS cast trapezoidal cross section spiral microfluidic device with two outlet tubes removed. The cut view of the cross section is shown on the left. The radius of the spiral curve varies from 7.5 mm to 12.5 mm. The inner & outer heights of the channel cross section are 80 μm and 130 μm, respectively. The width of the channel is 600 μm.

FIG. 11A: Input with 16.68 μm and 26.9 μm particle of 0.665% volume to volume concentration (about 2.6×10$^6$/mL), FIG. 11B: Inner side output, FIG. 11C: Outer side output.

FIG. 14B) spiral channel with rectangular cross-section of 500 μm×120 μm under optimal flow rate: 2 ml/min (De=8.63); FIG. 14C) spiral channel with trapezoid cross-section of 500 μm width, 70 μm (inner) and 100 μm (outer) depth under optimal flow rate: 0.8 ml/min (De=4.22). FIG. 14D) spiral channel with trapezoid cross-section of 500 μm width, 90 μm (inner) and 120 μm (outer) depth under optimal flow rate: 0.8 ml/min (De=4.32). Dashed horizontal lines indicate the positions of the channel walls.

FIG. 15A) 15.5 μm particles, $a_p/D_h$=0.104, $a_p/D_{inner}$=0.213; FIG. 15B) 10 μm particles, $a_p/D_h$=0.067, $a_p/D_{inner}$=0.137; FIG. 15C) 6 μm particles, $a_p/D_h$=0.040, $a_p/D_{inner}$=0.082. Dashed horizontal lines indicate the position of channel walls, while the inner channel walls were shown on the top side of the images.

FIG. 17A) Normalized intensity line scan indicating the distribution of polymorphonuclear leukocytes (PMLs), mononuclear leukocytes (MNLs) and RBCs (0.1% hematocrit) across the channel width at 0.8 ml/min. The inner channel wall is represented by x=0, and the outer channel wall is represented by x=500. FIG. 17B) Single-pass recovery percentage of total WBCs, PMNs, MNLs and RBCs at different hematocrit. Recovery percentage of 1% hematocrit (FIG. 17C) and 1.5% hematocrit (FIG. 17D) input sample after processing by a trapezoidal cross-sectional spiral in a 2-stage cascade manner. The amount of RBCs was measured by Coulter counter, and the amounts of WBCs, PMNs and MNLs were based on FACS analysis of Hochest-positive, CD66b-positive cells, Hochest-positive but CD66b-negative cells, separately. Error bars indicate the standard deviation of results from three tests.

FIGS. 18A-18B are illustrations of spiral processing of buffy coat obtained via differential centrifugation. FIG. 18A) A photo of healthy blood sample after centrifugation with Mono-Poly Resolving Medium. The first layer (FR1) consisted of MNLs, while the second layer (FR2) contained the majority of PMNs and some RBC residual. Cells from these two layers were re-suspended in the same volume of the original whole blood sample and further processed by the spiral microchannel with trapezoidal cross-section. FIG. 18B) Size distribution of cells in input and output samples of the trapezoidal cross-section spiral microchannel.

FIG. 19A) Nitroblue-tetrazolium (NBT) test on WBCs isolated by differential centrifugation method (MPRM) or spiral processing under conditions with or without 1 µM PMA. Scale bar: 10 µm. FIG. 19B) Comparison of activated PMNs in sample processed by different RBC removal methods based on FACS analysis of CD66b+ CD18+ cells. Error bars represent standard deviation of results from three tests.

FIG. 31A: Convex trapezoidal cross-section. FIG. 31B: Normal trapezoidal cross-section. FIG. 31C: Concave trapezoidal cross-section.

FIGS. 36A-D are photographs of blood from healthy donors (n=5) as well as patients with metastatic breast and lung cancer (n=10) that was processed using the spiral chip. FIG. 36A: Immunofluorescence staining of isolated CTC. CTC is identified by the following criteria: Hoechst positive, pan-cytokeratin positive and CD45 negative. FIG. 36B: CTCs enumeration plot for healthy donors, breast cancer patients, and lung cancer patients. FIG. 36C: Identification of cancer stem cells (CSCs) in breast samples using standard markers. No CD44+/CD24+ were detected. It was found that CD44+ cells are larger than CD24+ cells. FIG. 36D: Staining for apoptotic cells. The absence of cleaved caspase-3 in the isolated CTCs. Majority of the cells (>95%) expressing cleaved caspase-3 were CD45+.

DETAILED DESCRIPTION OF THE INVENTION

Figure 3A:
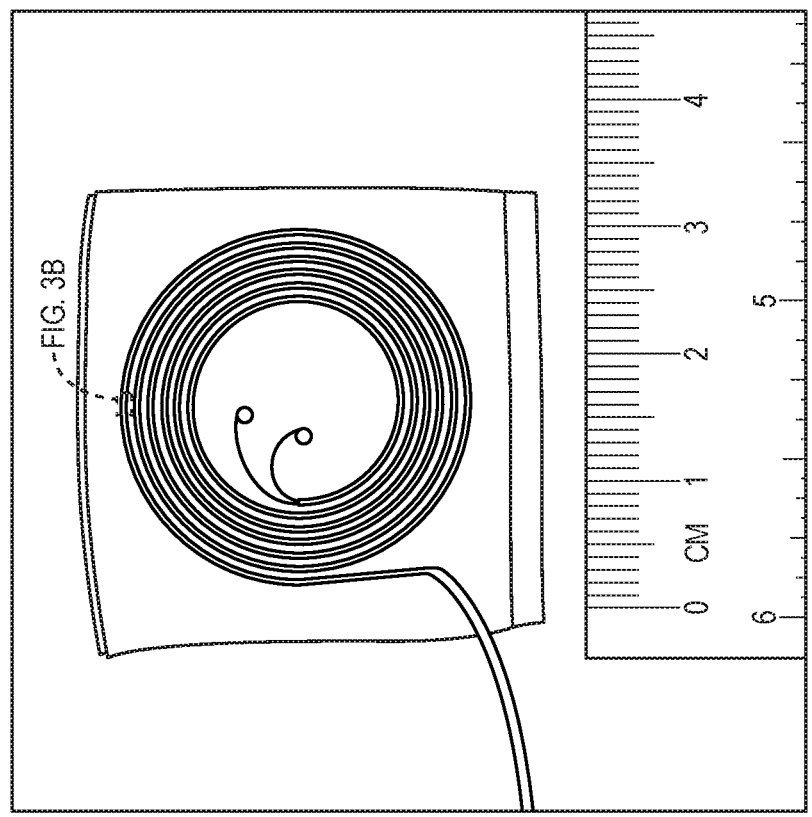
FIGS. 3A and 3B are line drawings of an actual trapezoid cross section spiral microfluidic device with a single inlet and two outlet tubes. The channels shown in FIG. 3A are filled with a dye for visualization. The device is made of two PDMS layers bonded via plasma. One of the layers that have a spiral pattern is cast from a micro milled PMMA mold. The cut view of the channel is shown in FIG. 3B. The width of the channel is 600 μm, the inner height (bottom) is 80 μm and outer height (top) is 140 μm.
Figure 3B:
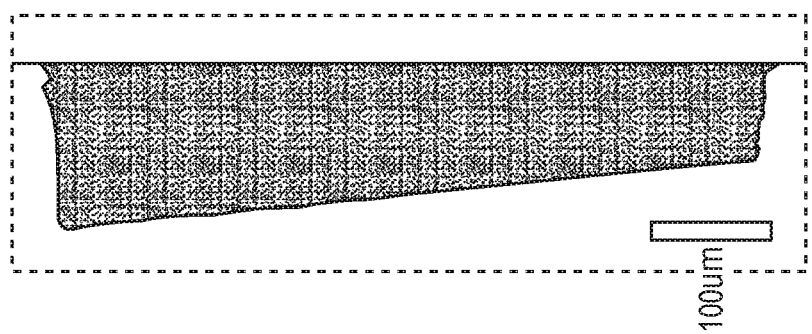

A description of example embodiments of the invention follows.

In micro-fluidic devices, particles flowing in curvilinear channels are influenced by both inertial migration and secondary Dean flows. The combination of Dean flow and inertial lift results in focusing and positioning of particles at distinct positions for concentration and separation applications.

Described herein is a set of curved micro-channels with non-rectangular cross-sections which are introduced into a microfluidic device resulting in the alteration of the shapes and positions of the Dean vortices which generates new focusing positions for particles. For example, as shown herein, a curved micro-channel with a deeper inner side (along the curvature center) and a shallow outer side generates two strong Dean vortex cores near the inner wall, trapping all particles irrespective of size within the vortex. Such a channel finds vast applications in particle and cell concentration applications, such as water filtration and purification at ultra-high throughputs.

Ultra-high throughput is a flow rate in a range of between about 0.5 mL/min and about 1 L/min. Ultra-high throughput can be achieved by combining multiple channels in a variety of combinations. In some aspects, multiple channels can be combined into a single micro-fluidic device. In other aspects, multiple channels can be combined into a multiplexed micro-fluidic device. Thus, an ultra-high throughput flow rate can be about 0.5 mL/min, about 5 mL/min, about 10 mL/min, about 20 mL/min, about 40 mL/min, about 50 mL/min, about 100 mL/min, about 200 mL/min, about 300 mL/min, about 400 mL/min, about 500 mL/min, about 600 mL/min, about 700 mL/min, about 800 mL/min, about 900 mL/min, or about 1 L/min.

As also shown herein, if the curved micro-channel has a shallow inner side and a deeper outer side, the vortex centers are skewed near the outer wall at the outer side which entrains particles and cells within the vortex. However, larger particles with dominant inertial force are focused near the inner channel walls, similar to rectangular cross-section channels. Thus, shown herein is that by designing appropriate channel parameters, small particles/cells are trapped in the vortex at the outside, while relatively large particles focus along the inner microchannel wall. The threshold diameter determining whether a particle/cell is trapped within the Dean vortex or focused towards the inner channel wall is dependent on the flow rate. This enables such a device to achieve good separation resolution between mixtures having a wide range of particle sizes. In aspects in which only two outlets are used for collection, the throughput is much higher than in rectangular channels where the particles are focusing near the inner side of the channel, toward the outlet collection branches placed at the inner side. This leads to low separation resolution, as well as carrying high risks of channel clogging. As shown herein, with a trapezoidal cross-section, higher particle/cell concentrations can be processed, with minimal interaction between them to achieve ultra-high throughputs.

The device described herein demonstrates separation of polynuclear leukocytes (PNLs) (diameters in a range of between about 10 µm and about 15 µm) from red blood cells (RBCs) (diameters of about 7-8 µm), and small mesenchymal stem cells (MSCs) (diameters in a range of between about 14 µm and about 20 µm) from large MSCs, (diameters larger than about 20 µm) and shows that the device achieved good separation resolution and high throughput for use, e.g., in clinical analysis and cell study. Moreover, as shown herein, channels with stepped cross-section and sandwiched shallow regions can be used for particle trapping and mixing.

Several types of curved channel (spiral, serpentine, arc) have been introduced in micro-fluidics recently. Experiments have shown that particles flowing in curved channels are influenced by both inertial force and Dean flow. The balance of these two effects can provide precise focusing and positioning of particles. This phenomenon can be used in many applications such as concentration or size selective separation of particles, or liquid filtration.

Fluid flowing through a channel with a laminar profile has a maximum velocity component near the centroid of the cross section of the channel, decreasing to zero near the wall surface. In a curved channel, the fluid experiences centrifugal acceleration directed radially outward. Since the magnitude of the acceleration is proportional to quadratic velocity, the centrifugal force in the centroid of the channel cross section is higher than at the channel walls. The non-uniform centrifugal force leads to the formation of two counter-rotating vortices known as Dean vortices in the top and bottom halves of the channel, which have a radially outward flow in the center and two inward flows near the channel walls as shown in FIG. 1A. Thus, particles flowing in a curvilinear channel experience a drag force due to the presence of these transverse Dean flows. Under Stokes' law, the drag force will be proportional to the Dean velocity at that point and proportional to the diameter of the particle. In the absence of other dominating forces, the Dean drag force will drive particles along the direction of flow within the vortex and finally entrain them within the core. In high aspect ratio rectangular cross section channels, this motion can be observed by observing particles moving back and forth along the channel width between the inner and outer walls with increasing downstream distance when visualized from the top or bottom.

Apart from the Dean drag force, larger cells with diameters comparable to the micro-channel dimensions also experience appreciable inertial lift forces resulting in their focusing and equilibration along the channel walls. In micro-channels with curvilinear geometry, the interplay between the inertial lift force and the Dean drag force reduces the equilibrium positions to just two near the inner channel wall at low flow rate, and move outward with an increase in flow rate, each within the top and bottom Dean vortex. The two equilibrium positions overlay each other along the micro-channel height and are located at the same distance from the micro-channel inner wall for a given cell size, i.e. viewed as a single position across the micro-channel width.

Figure 21:
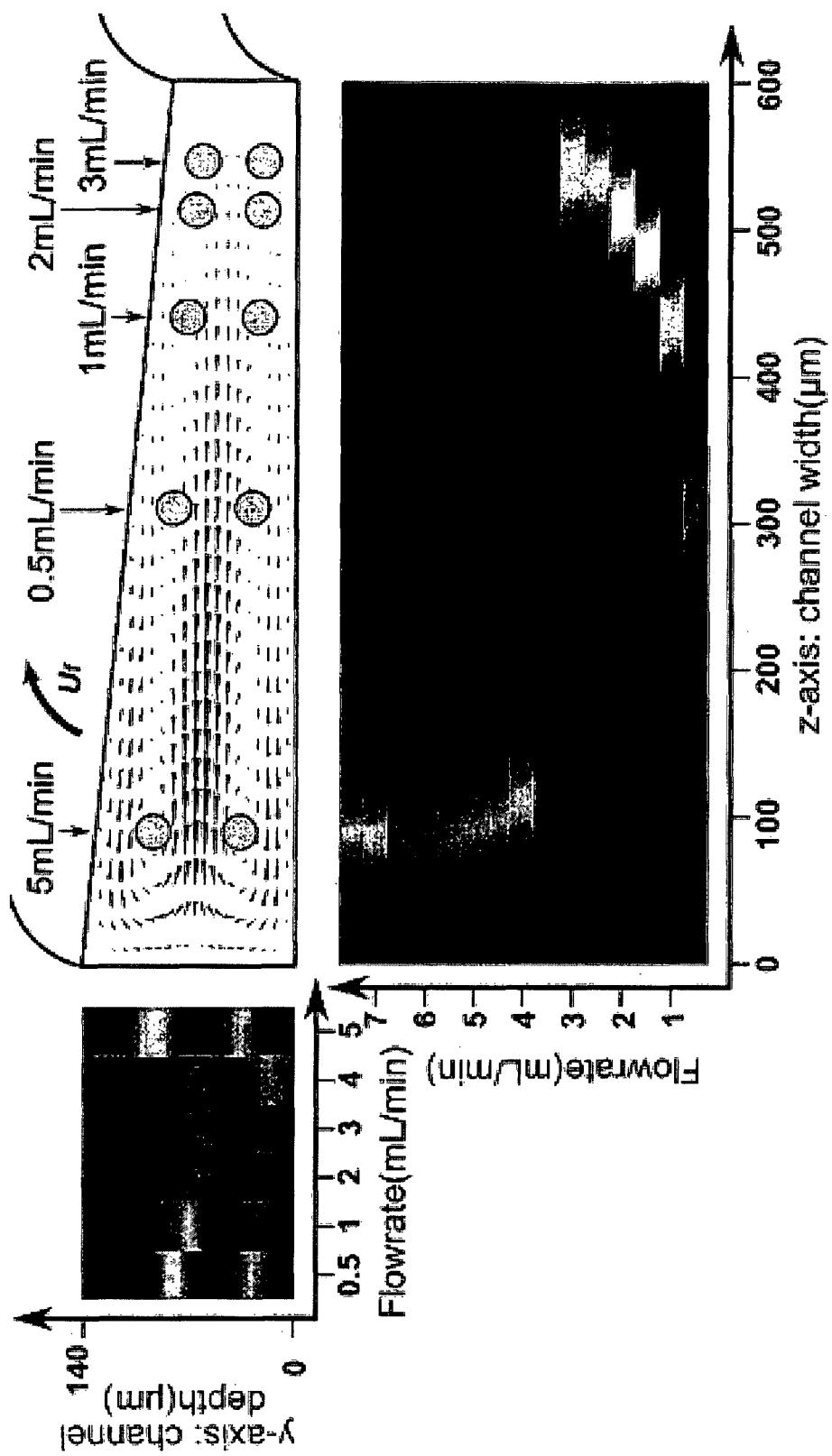
FIG. 21 is an illustration of balance of particles in a trapezoidal cross-section spiral microchannel with 80/140 µm inner/outer depth and 600 µm width. The black cones within channel cross-section are CFD simulation result of the Dean flow velocity (also Dean drag force) at a flow rate of 3.5 mL/min in a channel with radius 7.5 mm. The experimental images of 26.25 µm fluorescent beads distribution from the top view and side view are placed at the bottom and the left side of the simulation. By combining the top and side view observations, the positions of 26.25 µm beads at typical flow rate are drawn in gray circles in the channel cross-section.

As described herein, spiral microchannels with trapezoidal cross sections have been tested. These channels are different from rectangular cross section, in that the maximum velocity is asymmetric along the channel cross-section resulting in the formation of stronger Dean vortex cores skewed towards the deeper channel side. These vortex cores have high probability to entrain particles within them. As shown herein, in a spiral channel with trapezoidal cross-section, the particle focusing behavior is different from that in a rectangular channel. In a trapezoidal channel, as shown in FIG. 21, particles focus near the inner channel wall at low flow rate (similar to channels with rectangular cross-section), while beyond a certain threshold flow rate, they switch to an equilibrium position located at the outer half. Careful examination of the focusing positions in the top and side view revealed that particles are trapped at the centers of the two Dean vortices formed at the outer half of the channel.

Along the depth direction, according to experimental measurements, particles are focused between about 25.5-27.1% of the channel depth at flow rates of about 0.5-3.0 mL/min. This result indicates that the distance between the focused particle and the channel wall in a trapezoidal channel in the depth direction is larger than that in the rectangular channel.

If the inner wall of the channel is deeper, then these strong Dean vortices will appear at the inner side, i.e. particles will be trapped near the inner side, even at high flow rates. Curved channels with this cross section can be used to collect a larger size range of particles at the inner side of the outlet and filtered particle free liquid at the outer side of the outlet, finding numerous applications in water filtration, for example. On the other hand, if the outer wall of the channel is deeper, Dean vortices are skewed towards the outer side. At the inner side, the Dean flow field is much like that in a rectangular channel. At certain flow rates, the larger particle can focus along the inner wall influenced by both Dean flow and inertial lift, while the smaller particles tend to get trapped in the vortex center at the outer side. The different type of particle positioning (inside or outside) relative to their diameter presents a new size selective separation process.

Figure 5:
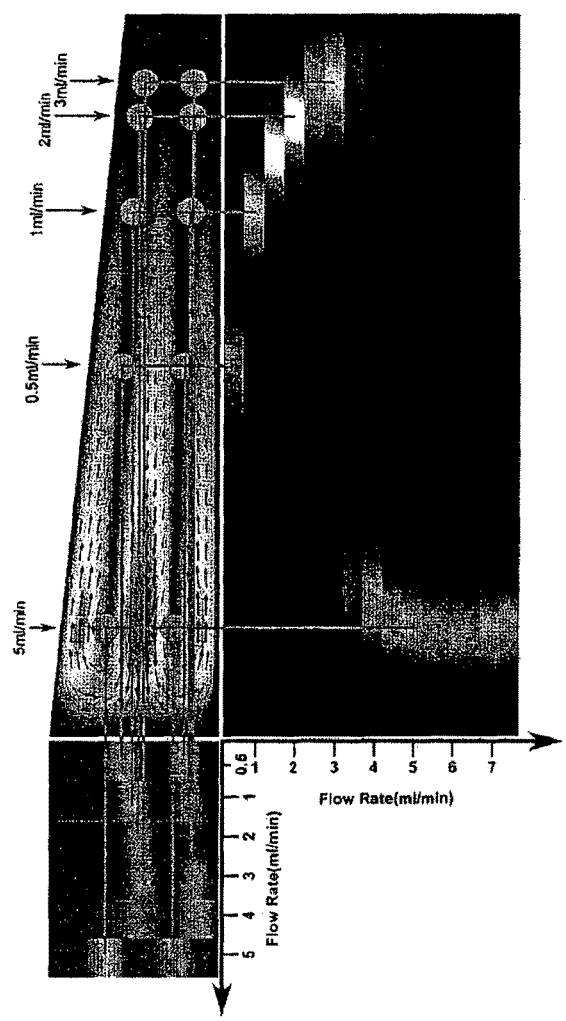
FIG. 5 is an illustration of a computational fluid dynamics (CFD) simulation result of the Dean flow field across a trapezoidal cross section spiral channel compared with experimental results indicating the force balanced position of particles in the cross section of a spiral channel. Arrows indicate the direction and magnitude of Dean flow, map indicates the magnitude of Dean flow. Dots are positions of 26.25 μm beads from experimental results.
Figures 7A, 7B:
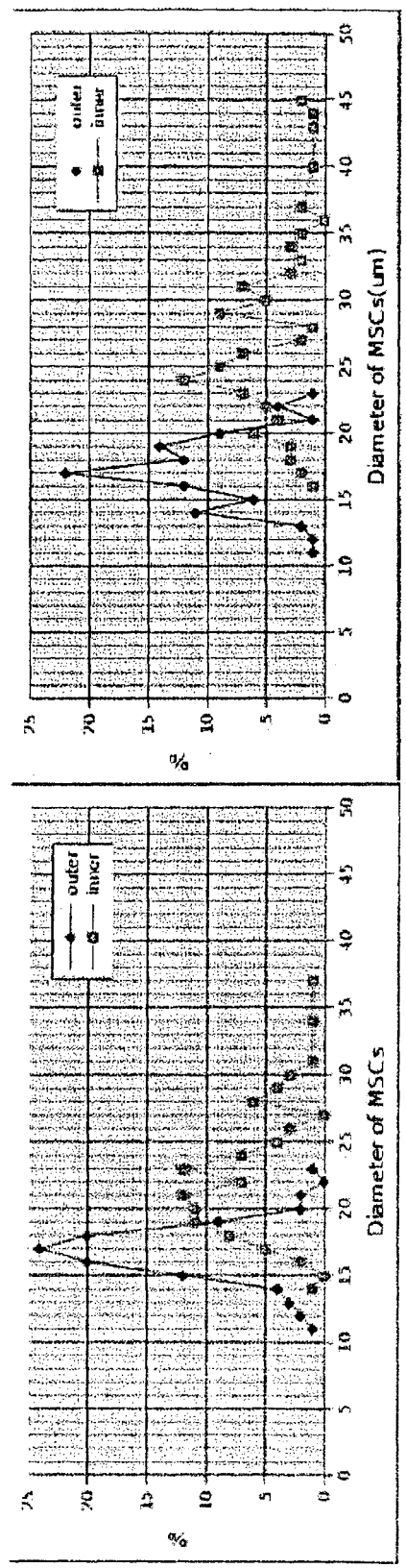
FIGS. 7A and 7B are graphs illustrating the size distribution of MSCs collected from two outlets after separation with a 80 μm-inner, 130 μm-outer and 600 μm-width trapezoid cross section spiral device, 100 cells are manually measured from each outlet collection.

FIG. 5 illustrates the phenomenon by simulating the Dean flow field with computational fluid dynamics (CFD) software and observing particle position from top and side view. It can be seen that the particles were flowing along the low Dean flow area. When the flow rate was lower than about 3 ml/min, particles were focused at the inner side as in rectangular channels, and when the flow rate increased over about 4 ml/min, the particles were trapped in the Dean vortex and move towards the outer channel wall.

FIGS. 4A-4H present the position of different size particles within the cross-section when viewed from the top view for increasing flow rates. In this device, there were two typical regimes of focusing based on the particle size, the inertial dominant and Dean dominant regimes. For small particles (e.g., 5.78 μm particles), the large channel dimension prevented them from focusing and these particles got trapped in the Dean vortex even at low flow rate. The larger particles (e.g., about 9.77 μm particles) also could not focus at the inner wall and were trapped within the Dean vortices at flow rates≥about 1 ml/min. The 15.5 μm particles focused at the inner wall at low flow rates, about 1.5 ml/min, but transitioned from the inertial dominant regime to Dean dominant regime at about 2 ml/min. For the same micro-channel, the 26.25 μm particles transitioned from the inertial regime to Dean regime at flow rates about 3 ml/min. From these results, at a flow rate of about 1.5 ml/min, particles>about 15.5 μm can be separated from smaller ones by collecting from the inner and outer outlets separately. Similarly, at a flow rate of about 2.5 ml/min, about 26.25 μm particles can be separated from a mixture of about 26.25 μm and about 15.5 μm particles. In some aspects, a low flow rate can be in a range of between about 0.5 mL/min and about 2 mL/min. Thus, a low flow rate can be a flow rate of about 0.5 mL/min, about 0.6 mL/min, about 0.7 mL/min, about 0.8 mL/min, about 0.9 mL/min, about 1.0 mL/min, about 1.1 mL/min, about 1.2 mL/min, about 1.3 mL/min, about 1.4 mL/min, about 1.5 mL/min, about 1.6 mL/min, about 1.7 mL/min, about 1.8 mL/min, about 1.9 mL/min, or about 2.0 mL/min. In certain aspects, a high flow rate can be a flow rate in a range of between about 6 mL/min and about 10 mL/min. Thus a high flow rate can be a flow rate of about 6 mL/min, about 6.5 mL/min, about 7.0 mL/min, about 7.5 mL/min, about 8.0 mL/min, about 8.5 mL/min, about 9.0 mL/min, about 9.5 mL/min, or about 10.0 mL/min.

Accordingly, in some aspects, the invention relates to a set of curved micro-channels with non-rectangular cross-section that give rise to unique Dean vortices for varying applications in micro-fluidic field relating to particle focusing, separation, and mixing. In a particular aspect, the invention is directed to a micro-fluidic device that includes at least one inlet and a curvilinear microchannel having a trapezoidal cross section defined by a radially inner side, a radially outer side, a bottom side, and a top side, the cross section having a) the radially inner side and the radially outer side unequal in height, or b) the radially inner side equal in height to the radially outer side, and wherein the top side has at least two continuous straight sections, each unequal in width to the bottom side. The device further comprises at least one outlet. In certain aspects, a spiral channel with a trapezoidal cross-sections consisting of a shallow inner side and deeper outer wall is used as a high resolution size based particle separator.

In some aspects, the micro-fluidic device includes a single inlet, 2 inlets, 3 inlets, 4 inlets, 5 inlets, 6 inlets, 7 inlets, 8 inlets, 9 inlets, or 10 or more inlets.

In one aspect, the curvilinear microchannel 120 can be a spiral microchannel as shown in FIG. 1A. In another aspect, the curvilinear microchannel 120 can be a serpentine microchannel as shown in FIG. 1B. The curvilinear microchannel 120 can have a radius of curvature in a range of between about 2.5 mm and about 25 mm. For example, the curvilinear microchannel can have a radius of curvature of about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. The curvilinear microchannel can also have a length in a range of between about 4 cm and about 100 cm. For example, the curvilinear microchannel can have a length of about 5 cm, about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, about 95 mm, or about 100 cm.

The micro-fluidic device further includes at least one outlet. In certain aspects, the micro-fluidic device includes two outlets, 3 outlets, 4 outlets, 5 outlets, 6 outlets, 7 outlets, 8 outlets, 9 outlets, or 10 or more outlets. In a particular aspect, the micro-fluidic device has two outlets for waste and particle collection, respectively. In another aspect, the micro-fluidic device has a single inlet and only 2 outlets.

For a trapezoidal cross-section spiral microchannel, there are several factors that affect the focusing position and separation efficiency, such as the width of the microchannel, inner and outer depth of the microchannel cross-section, the radius of the spiral curvature, and the slant angle. The width can be in a range of between about 100 μm and about 2000 μm, such as a width of about 200 μm, about 300 μm, about 400 μm, about 500 μm, about 600 μm, about 700 μm, about 800 μm, about 900 μm, about 1000 μm, about 1100 μm, about 1200 μm, about 1300 μm, about 1400 μm, about 1500 μm, about 1600 μm, about 1700 μm, about 1800 μm, or about 1900 μm.

The outer depth can be in a range of between about 20 μm and about 200 μm, such as an outer depth of about 40 μm, about 60 μm, about 80 μm, about 100 μm, about 120 μm, about 140 μm, about 160 μm, or about 180 μm. The inner depth can be in a range of between about 20 μm and about 200 μm, such as an inner depth of about 40 μm, about 60 μm, about 80 μm, about 100 μm, about 120 μm, about 140 μm, about 160 μm, or about 180 μm. The radius of curvature can be in a range of between about 2.5 mm and about 25 mm, such as a radius of about 5 mm, about 7.5 mm, about 10 mm, about 12.5 mm, about 15 mm, about 17.5 mm, about 20 mm, or about 22.5 mm.

The slant angle is the angle between the top of the channel and the bottom of the channel. The slant angle can be in a range of between about 2 degrees and about 60 degrees. Thus, the slant angle can be about 2 degrees, about 4 degrees, about 6 degrees, about 8 degrees, about 10 degrees, about 12 degrees, about 14 degrees, about 16 degrees, about 18 degrees, about 20 degrees, about 22 degrees, about 24 degrees, about 26 degrees, about 28 degrees, about 30 degrees, about 32 degrees, about 34 degrees, about 36 degrees, about 38 degrees, about 40 degrees, about 42 degrees, about 42 degrees, about 46 degrees, about 48 degrees, about 50 degrees, about 52 degrees, about 54 degrees, about 56 degrees, about 58 degrees, or about 60 degrees. The slant angle of the channel affects the focusing behavior in two ways: (i) the threshold flow rate required to trap particles in the Dean vortex as a function of particle size and (ii) the location of the Dean vortex core. A large slant angle (i.e., in a range of between about 10 degrees and about 60 degrees) will lead to strong Dean at the outer side and increase the particle trapping capability. A large slant angle can also decrease the threshold flow rate required to trap particles of a given size within the Dean vortex.

In a particular aspect, the invention is directed to a micro-fluidic device 100 as shown in FIG. 1A that includes at least one inlet 110 and a curvilinear microchannel 120 having a trapezoidal cross section 201 as shown in FIG. 2a or 202 as shown in FIG. 2b, defined by a radially inner side 210, a radially outer side 220, a bottom side 230, and a top side 240, the cross section having a) the radially inner side 210 and the radially outer side 220 unequal in height, or b) the radially inner side 210 equal in height to the radially outer side 220 as shown in FIG. 2d, and wherein the top side 240 has at least two continuous straight sections 240a and 240b, each unequal in width to the bottom side 230. The micro-fluidic device further includes at least one outlet 130.

Figures 31A, 31B, 31C:
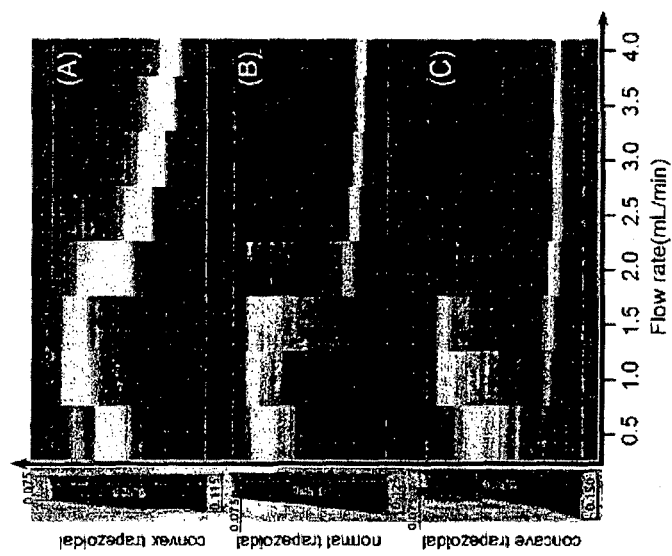
FIGS. 31A-31C are top view microscopy images of 15.5 µm fluorescent particles focus band shift with flow rate under different geometry of channel cross-section. The width of the channels is 500 µm. The inner depth is 75 µm. Area of channel cross-sections is designed to be equal in all three channels, $5.0 \times 10^{-2}$ mm$^2$. Lines indicate the channel walls.

In some aspects, the cross section 201 of the micro-fluidic device can have the height of the radially inner side 210 larger than the height of the radially outer side 220 as shown in FIG. 2a. In other aspects, the height of the radially inner side 210 can be smaller than the height of the radially outer side 220 as shown in FIG. 2b. In yet other aspects, the top side 240 can include at least one step (241, 242, 243, etc.) forming a stepped profile 203 as shown in FIG. 2c. In this specific aspect, the radially inner side 210 can be larger or smaller than the height of the radially outer side 220. In still other aspects, the top side 240 can include at least one shallow region 240c in between the radially inner side 210 and the radially outer side 220 as shown in FIG. 2d. The trapezoidal cross section can be a right (i.e., normal) trapezoidal cross section as shown in FIG. 31B. In certain aspects, the top and/or bottom sides of the trapezoidal cross section can be curved, with a curvature that can be convex, as shown in FIG. 31A, or concave, as shown in FIG. 31C.

In other aspects, the radially inner side 210 and the radially outer side 220 of the trapezoidal cross section can have a height in a range of between about 20 microns (μm) and about 200 μm. Thus, the height of the radially inner side 210 can be about 20 μm, about 40 μm, about 60 μm, about 80 μm, about 100 μm, about 120 μm, about 140 μm, about 160 μm, about 180 μm, or about 200 μm, and the height of the radially outer side 220 can be about 20 μm, about 40 μm, about 60 μm, about 80 μm, about 100 μm, about 120 μm, about 140 μm, about 160 μm, about 180 μm, or about 200 μm. In some aspects, the height of the radially inner side 210 can be about 70 µm, or about 80 µm, or about 90 µm, and the height of the radially outer side 220 can be about 100 µm, or about 120 µm, or about 130 µm, or about 140 µm.

In certain aspects, the top side 240 and the bottom side 230 of the trapezoidal cross section can have a width in a range of between about 100 µm and about 2000 µm, such as a width of about 200 µm, about 300 µm, about 400 µm, about 500 µm, about 600 µm, about 700 µm, about 800 µm, about 900 µm, about 1000 µm, about 1100 µm, about 1200 µm, about 1300 µm, about 1400 µm, about 1500 µm, about 1600 µm, about 1700 µm, about 1800 µm, or a width of about 1900 µm.

Figures 24A, 24B:
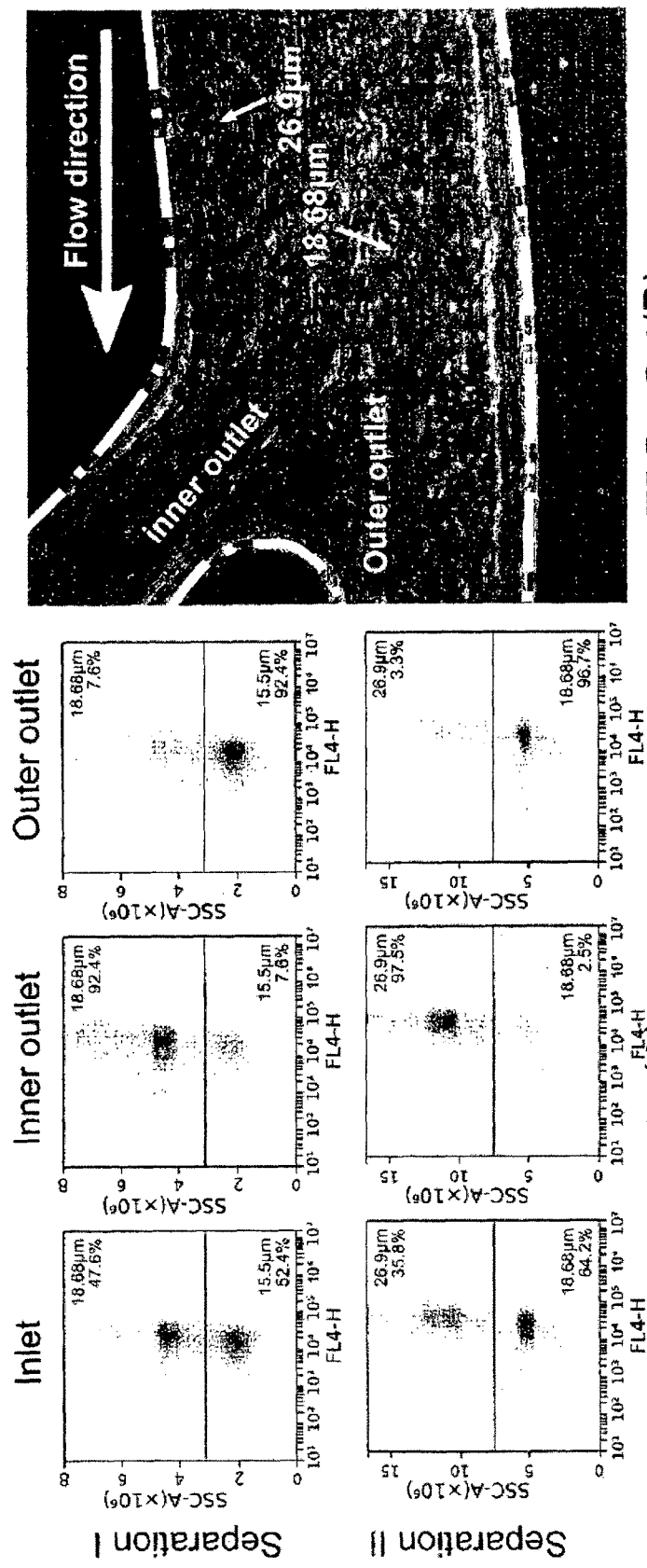
FIG. 24A shows scatter plots captured using flow cytometer (Accuri C6, BD Biosciences, USA) showing the results of separations of particle mixtures in a 80 µm inner depth, 130 µm outer depth, and 600 µm wide trapezoidal cross-section channel.
FIG. 24B is a high speed microscope image (Phantom V9.1, Vision. Research Inc. USA, exposure time=4 µs) captured at the outlet bifurcation clearly showing the separation of 18.68 µm and 26.9 µm particles at a flow rate of 3.4 mL/min.

FIG. 24A shows experimental results confirming the three dimensional particle focusing in spiral microchannels. The results indicate that particles form two bands along the depth symmetrically between the zero-lift force plane and the centers of the Dean vortex in spiral channels. In a particular aspect, a multi-loop microchannel was employed to calibrate the focusing of different size standard micro particles of about 5.78 µm, about 9.77 µm, about 15.5 µm, and about 26.25 µm diameter for flow rates ranging from about 0.5 to about 7.5 mL/min.

Figure 9A:
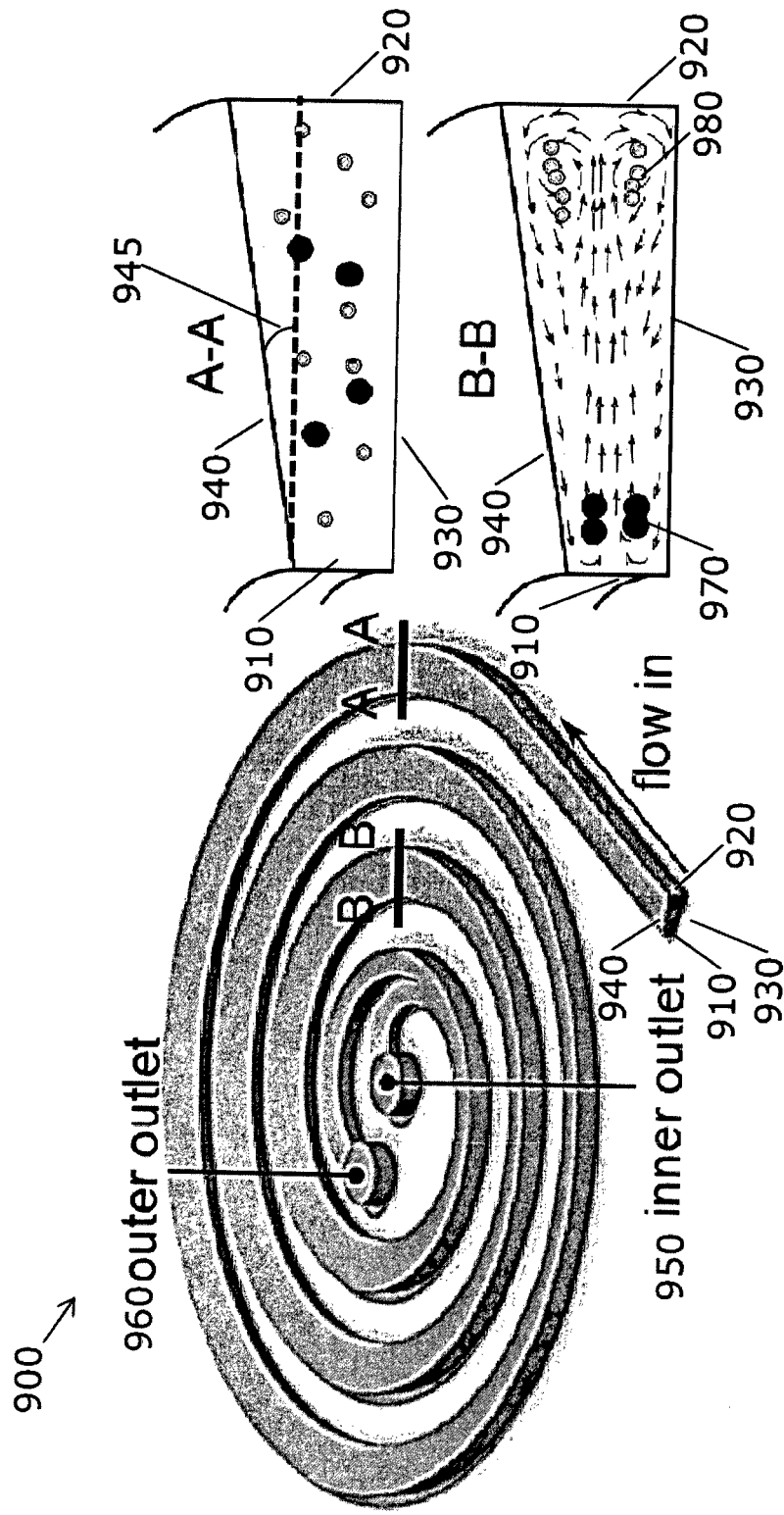
FIG. 9A is a schematic of a trapezoidal cross section channel illustrating the principle of particle focusing and trapping within the Dean vortices.

Thus, as described herein, spiral microchannels can comprise one or more loops. In certain aspects, the multi-loop microchannel can be a 2 loop microchannel, a 3 loop microchannel, a 4 loop microchannel a 5 loop microchannel, a 6 loop microchannel, a 7 loop microchannel, an 8 loop microchannel, a 9 loop microchannel, a 10 loop microchannel, etc. In a particular aspect, shown in FIG. 9B, the multi-loop microchannel can be an 8 loop microchannel. In one specific aspect of an 8 loop microchannel, the device can be an 8-loop spiral microchannel with one inlet and two outlets with radius of curvature decreasing from about 24 mm at the inlet to about 8 mm at the two outlets for efficient cell migration and focusing. The width of the channel cross-section can be about 600 µm and the inner/outer heights can be about 80 µm and about 130 µm, respectively, for the trapezoid cross-section. In another aspect, shown in FIG. 1A, the multi-loop microchannel can be a 4 loop microchannel.

The experimental results indicate that particles occupied an equilibrium position near the inner microchannel wall when particles were introduced under a lower flow rate. However, beyond a threshold flow rate (which is dependent on the particle size) the equilibrium position was moved to the outer microchannel wall, suggested to be a Dean vortex trap. Taking advantage of this sudden transition, the trapezoidal cross-section spiral microchannel produced higher resolution separation of particles than conventional rectangular cross-section spiral. Separation of 15.5 µm and 18.68 µm beads at an ultra-high throughput of about $1.61 \times 10^7$/min with over 92% efficiency was achieved with this device. Ultra-high throughput can be a throughput in a range of between about 1 particles/min to about $1 \times 10^9$ particles/min.

As will be appreciated by those of skill in the art, depending upon the use, one or more micro-fluidic devices can be coupled, thereby generating a multiplexed device, For example, the outlet of one micro-fluidic device can be connected to the inlet of one or more micro-fluidic devices. Alternatively or additionally, multiple channels can be integrated into a micro-fluidic device. The number of channels that can be multiplexed and/or integrated into a micro-fluidic device can be in a range of between about 2 channels and about 500 channels. Thus, the number of channels can be about 2 channels, about 5 channels, about 10 channels, about 20 channels, about 30 channels, about 40 channels, about 50 channels, about 100 channels, about 200 channels, about 300 channels, about 400 channels, or about 500 channels.

As will also be appreciated by those of skill in the art, the micro-fluidic device can further comprise other components upstream, downstream, or within (e.g., a multiplexed) a device. For example, one or more micro-fluidic devices can further comprise one or more collection devices (e.g., a reservoir), flow devices (e.g., a syringe, pump, pressure gauge, temperature gauge), analysis devices (e.g., a 96-well microtiter plate, a microscope), filtration devices (e.g., a membrane), e.g., for upstream or downstream analysis (e.g., immunostaining, polymerase chain reaction (PCR) such as reverse PCR, quantitative PCR), fluorescence (e.g., fluorescence in situ hybridization (FISH)), sequencing, and the like. An imaging system may be connected to the device, to capture images from the device, and/or may receive light from the device, in order to permit real time visualization of the isolation process and/or to permit real time enumeration of isolated cells. In one example, the imaging system may view and/or digitize the image obtained through a microscope when the device is mounted on a microscope slide. For instance, the imaging system may include a digitizer and/or camera coupled to the microscope and to a viewing monitor and computer processor.

The microfluidic device described herein can be used for a variety of purposes. In one aspect, shown in FIG. 9A, the invention is directed to a method of separating by size one or more particles from a mixture of particles. The method comprises introducing the mixture into at least one inlet (not shown) of a micro-fluidic device 900 that includes a curvilinear microchannel having a trapezoidal cross section defined by a radially inner side 910, a radially outer side 920, a bottom side 930, and a top side 940, the cross section having the height of the radially inner side 910 smaller than the height of the radially outer side 920, thereby defining a slant angle 945, at a flow rate that isolates particles along portions of the cross-section of the microchannel based on particle size, wherein larger particles 970 flow along the radially inner side 910 of the microchannel to a first (inner) outlet 950 and smaller particles 980 flow along other portions of the microchannel to at least one other (outer) outlet 960, thereby size separating the particles from the mixture. The method can include collecting size separated particles from the first outlet 950.

Particles present in a variety of mixtures can be introduced into the device. Examples of mixtures include biological fluids (e.g., a biological sample such as blood, lymph, urine, and the like), liquids (e.g., water), culture media, emulsions, sewage, etc. In the aspect in which the biological sample is whole blood, the blood can be introduced unadulterated or adulterated (e.g., lysed, diluted). Methods of lysing blood are known in the art. In some aspects, the volume to volume concentration of the particles as compared to other cells can be less than about 5%. Thus, the volume to volume concentration can be about 4%, about 3%, or about 2%. In some aspects, dilution of blood sample can be to a hematocrit in a range of between about 0.5% and about 2%. Thus, the hematocrit of a diluted blood sample can be about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2%.

In yet another aspect, the invention is directed to a method of concentrating cells from a mixture. The method comprises introducing the mixture into at least one inlet of a micro-fluidic device that includes a curvilinear microchannel having a trapezoidal cross section 201 as shown in FIG.

2a defined by a radially inner side 210, a radially outer side 220, a bottom side 230, and a top side 240, the cross section having the height of the radially inner side 210 larger than the height of the radially outer side 220, at a flow rate that isolates the cells along the radially inner side of the cross section of the microchannel and directs them to a first outlet (not shown), thereby concentrating the cells from the mixture. The method can include collecting concentrated cells from the first outlet. In particular aspects, the flow rate can be in a range of between about 0.5 mL/min and about 10 mL/min.

In yet another aspect, the invention is directed to a method of filtering particulates from a mixuture (e.g., water). Particulates can include bacteria, fungi, parasites, floc, or other sedimentary aggregates present in water. The method comprises introducing particulate containing water into at least one inlet of a micro-fluidic device that includes a curvilinear microchannel having a trapezoidal cross section 201 as shown in FIG. 2a defined by a radially inner side 210, a radially outer side 220, a bottom side 230, and a top side 240, the cross section having the height of the radially inner side 210 larger than the height of the radially outer side 220, at a flow rate that isolates particulates along the radially inner side 210 of the cross section of the microchannel and directs them to a first outlet (not shown), thereby filtering the particulates from the water. The method can include collecting particulates from the first outlet. In particular aspects, the flow rate can be in a range of between about 0.5 mL/min and about 10 mL/min.

In another aspect, the invention is directed to a method of distributing cells in a mixture. The method comprises introducing the mixture into at least one inlet of the micro-fluidic device that includes a curvilinear microchannel having a trapezoidal cross section 203 as shown in FIG. 2c defined by a radially inner side 210, a radially outer side 220, a bottom side 230, and a top side 240, the cross section having the top side 240 that includes at least one step (241, 242, 243, etc.) forming a stepped profile, at a flow rate that distributes cells along portions of the stepped profile, wherein cells do not impact the sides before, during, or after distribution to separate outlets (not shown), thereby distributing the cells in the mixture. The method can include collecting distributed cells from the separate outlets. In particular aspects, the flow rate can be in a range of between about 2 mL/min and about 10 mL/min.

In yet another aspect, a method of mixing cells in a liquid includes introducing a liquid and cells into at least one inlet of the micro-fluidic device having a curvilinear microchannel having a trapezoidal cross section 204 as shown in FIG. 2d defined by a radially inner side 210, a radially outer side 220, a bottom side 230, and a top side 240, the cross section having the top side 240 including at least one shallow region 240c in between the radially inner side 210 and the radially outer side 220, at a flow rate that mixes cells along the microchannel and directs the mixture to a first outlet (not shown). The method can include collecting the mixture from the first outlet. In particular aspects, the flow rate can be in a range of between about 0.1 mL/min and about 2 mL/min.

In the methods described herein, fluid can be introduced into the micro-fluidic device in a variety of ways. In one aspect, fluid can be introduced into the micro-fluidic device using a syringe pump. In other aspects, fluid can be introduced into the micro-fluidic device using a piston pump, a gear pump, a peristaltic pump, a piezoelectric micropump, or using a controllable pressure regulator. The flow rate of fluid through the micro-fluidic device will vary depending on the use. In some aspects, the flow rate can be in a range of between about 0.5 mL/min and about 10 mL/min, such as a flow rate of about 1 mL/min, about 2 mL/min, about 3 mL/min, about 4 mL/min, about 5 mL/min, about 6 mL/min, about 7 mL/min, about 8 mL/min, or about 9 mL/min.

A variety of particles can be separated using the micro-fluidic device. In a particular aspect, larger particles can be separated from smaller particles. Larger particles can have a diameter from about 18 µm to about 50 µm. For example, larger particles can have a diameter of about 19 µm, about 20 µm, about 21 µm, about 22 µm, about 23 µm, about 24 µm, about 25 µm, about 26 µm, about 27 µm, about 28 µm, about 29 µm, about 30 µm, about 31 µm, about 32 µm, about 33 µm, about 34 µm, about 35 µm, about 36 µm, about 37 µm, about 38 µm, about 39 µm, about 40 µm, about 41 µm, about 42 µm, about 43 µm, about 44 µm, about 45 µm, about 46 µm, about 47 µm, about 48 µm, about 49 µm, or about 50 µm. Smaller particles can have a diameter from about 2 µm to about 14 µm. For example, smaller particles can have a diameter of about 2 µm, about 3 µm, about 4 µm, about 5 µm, about 6 µm, about 7 µm, about 8 µm, about 9 µm, about 10 µm, about 11 µm, about 12 µm, about 13 µm, or about 14 µm. In a particular aspect, the flow rate can be about 2.5 mL/min, the larger particles can have a diameter in a range of between about 18 µm and about 40 µm, and the smaller particles can have a diameter in a range of between about 10 µm and about 20 µm. In another particular aspect, the flow rate can be about 1.5 mL/min, the larger particles can have an diameter in a range of between about 15 µm and about 25 µm, and the smaller particles can have a diameter in a range of between about 5 µm and about 10 µm. In still another particular aspect, the flow rate can be in a range of between about 2.5 mL/min and about 3.0 mL/min, the larger particles can have a diameter in a range of between about 25 µm and about 40 µm, and the smaller particles can have a diameter in a range of between about 5 µm and about 15 µm.

In some aspects, the particles can be cells, such as stem cells. In another aspect, the cells can be present in a biological fluid (e.g., blood, urine, lymph, cerebrospinal fluid, and the like). In a particular aspect, the cells are present in a blood sample, wherein the larger cells are circulating tumor cells (CTCs), and the smaller cells are hematologic cells. In some aspects, the CTCs are cancer cells (e.g., metastatic cancer cells) from a (one or more) breast cancer, colorectal cancer, kidney cancer, lung cancer, gastric cancer, prostate cancer, ovarian cancer, squamous cell cancer, hepatocellular cancer, nasopharyngeal cancer and other types of cancer cells. Because this approach does not require initial cell surface biomarker selection, it is suitable for use in different cancers of both epithelial and non-epithelial origin.

The methods described herein can further comprise collecting and isolating the separated particles (e.g., cells). In certain aspects, the method can further comprise downstream analysis such as immunostaining, qRT-PCR, FISH and sequencing. In a particular aspect, the method can further comprise conducting a heterogeneity study.

In the methods described herein, unless otherwise specified, the capture efficiency of particles (e.g., CTCs) can be in a range of between about 60% and about 100%, such as about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, and about 99%. In a particular aspect, the capture efficiency can be an average recovery of 80%, or 85%, or 87%. In another particular aspect, detection of HER2 amplification in CTCs can identify high-risk breast cancer patients who may benefit from HER2 associated therapeutic strategies.

The micro-fluidic device described herein can process milliliter quantities of fluid, e.g., blood, in minutes. In a specific aspect, the micro-fluidic device having a trapezoidal cross section can process 7.5 mL of blood, (e.g., lysed red blood cells) in about 8 minutes, allowing enrichment of viable CTCs, and can process smaller quantities of blood, such as 4 mL in about 5 minutes, and can process larger quantities of blood, such as about 20 mL in about 15 minutes, or 40 mL in about 30 minutes, or 60 mL in about 45 minutes, or 80 mL in about 60 minutes, or larger quantities in more than 1 hour.

In still another aspect, the larger cells can be leukocytes, and the smaller cells can be hematologic cells. In yet another aspect, the mixture can be a bone marrow sample, wherein stem cells can be separated from hematologic cells.

Size based cell separation is a challenging requirement in cell study for the isolation of certain types of cells from cell mixtures. For example, cancer metastasis, mortal consequence of tumorigenesis, accounts for about 90% of all cancer related deaths. During metastasis, viable tumor-derived epithelial cells (circulating tumor cells or CTCs) are shed into peripheral blood of patients with metastatic carcinomas during early stages of tumorigenesis and are probably responsible for extravasation at distant organs to form new metastatic sites. Clinical reports have shown that detection of CTCs can provide valuable insights associated with disease stage and cancer progression. Separation based on size difference between CTCs, which are typically about 20 μm in diameter, and the other blood cells (RBC about 8 μm; leukocytes about 10-15 μm) would be a good way to separate these rare CTCs from hematologic cells.

Another example is neutrophils, which are key effectors of the innate immune response against bacterial infection; over-exuberant response could lead to systemic inflammation and organ dysfunction in sepsis. Therefore, neutrophils themselves have been recognized as a potential target in controlling sepsis. In animal models of sepsis, studies showed that depleting neutrophils or antagonizing their activities helps to maintain organ function. It's tempting to hypothesize that deletion of circulating neutrophils in sepsis patients' blood might help to control inflammation, and a continuous blood separation technique is necessary to validate the hypothesis. Since it's well known that blood cells with various cell types have different cell size, such as polymorphonuclear leukocytes (PNLs) with cell diameter in a range of between about 10 μm and about 15 μm, monocytes and lymphocytes with cell diameter in a range of between about 7 μm and about 8 μm, and erythrocytes with a disk diameter in a range of between about 6 μm and about 8 μm, a size-based separation technique might be helpful in fractionating blood into different blood components.

Mesenchymal stem cells(MSCs) are adult stem cells from bone marrow that can differentiate into multiple non hematopoietic cell lineages. Previous papers have reported that single-cell-derived colonies of marrow stromal cells contained several morphologically distinct cell types. In early colonies, very small round cells rapidly self-renew, as compared with large ones. Samples enriched in the smaller cells had a greater potential for multipotential differentiation than samples enriched in the larger cells. High resolution size based separation is also required for this kind of application.

FIGS. 6A-6D show the performance of an exemplary device in separating PNLs from fresh human blood. The spiral channel with a trapezoidal cross-section of 500 μm in width, 90 μm and 120 μm in depth at inner or outer wall, respectively, was fabricated in PDMS polymer. The device achieved >90% PNL recovery for a 2% hematocrit blood sample, while maintaining ~75% RBC removal, in a continuous and high-throughput manner, allowing the selective transfusion of neutrophil-depleted blood when being coupled. Giemsa staining of the output sample further confirmed that 98% of isolated PNLs were neutrophils. Although it has been known that mechanical stress could lead to neutrophil activation, the NBT test on both the input and output sample demonstrated that the isolated neutrophils remained alive and non-activated after being processed by this device. Therefore, the subsequence clinical and molecular diagnostics tests on the isolated neutrophils should reveal the initial state of the input sample.

As a demonstration of MSCs separation, an early passage MSCs cell line was diluted to about 10 k/ml and tested in a 80 μm inner and 130 μm outer height, 600 μm width 8 loops spiral. After experiment, 100 random cells were measured manually from each outlet. The size distribution results are shown in FIGS. 7A-7B and 8A-8B. As expected, cells are separated into two subgroups according to their size. At 2.2 mL/min flow rate, the majority of cells collected at the inner outlet are 18-30 μm cells (about 30% of the test MSCs), while the cells at the outer outlet range from 15 μm to 19 μm (about 70% of the test MSCs). If the flow rate increases to 3 mL/min, then there are more 20 μm cells in the outer side and fewer cells under 22 μm collected in the inner side, and the separation threshold is thus shifted. The results indicate that the trapezoid cross-section is able to reach high resolution separation that has never been reported with rectangular cross section channels.

In the case of a spiral channel having stepped cross-section as shown in FIG. 2-c, the Dean flows near the steps are interrupted by the steps, creating local Dean vortices. Initial results indicate that these vortices have the ability to trap particles within them. A potential application of this type of channel can be as a distributor for high flow rate cell delivery. Cells are trapped at the different positions, which prevent them from being damaged by hitting the channel wall when they are separated to multiple sub-branches.

A spiral microchannel with a sandwiched shallow region between two deeper regions, as shown in FIG. 2d, makes the Dean flow and inertial lift profiles even more complex. A two cores spiral channel with height switch between 0.3 and 0.45 mm has shown that particles cannot be focused or trapped in any position. The result indicates that such a pattern can be used as a mixer. An advantage of this type of mixer is that the samples are mixed according to the secondary flows, thus the mixing process is gentler than with mixers having pillar patterns.

EXEMPLIFICATION

Example 1

High Resolution Size Based Micro Particle/Cell Separator with Trapezoidal Cross Section Spiral Microchannels Particle focusing behavior in a spiral microfluidic channel with trapezoidal cross section is described below. By observing the position of a particle stream from both side and top views, combined with numerical simulation of the Dean flow field, the force balance conditions within these channels are studied for better understanding of the particle focusing mechanism in a spiral inertial microfluidic channel. In the spiral inertial microfluidic channel, modifying the channel cross section can lead to a shift in Dean flow field, affecting the particle focusing behavior significantly. Based on this mechanism, particles separation with both high resolution and high throughput is accomplished.

Theory

Figure 10A:
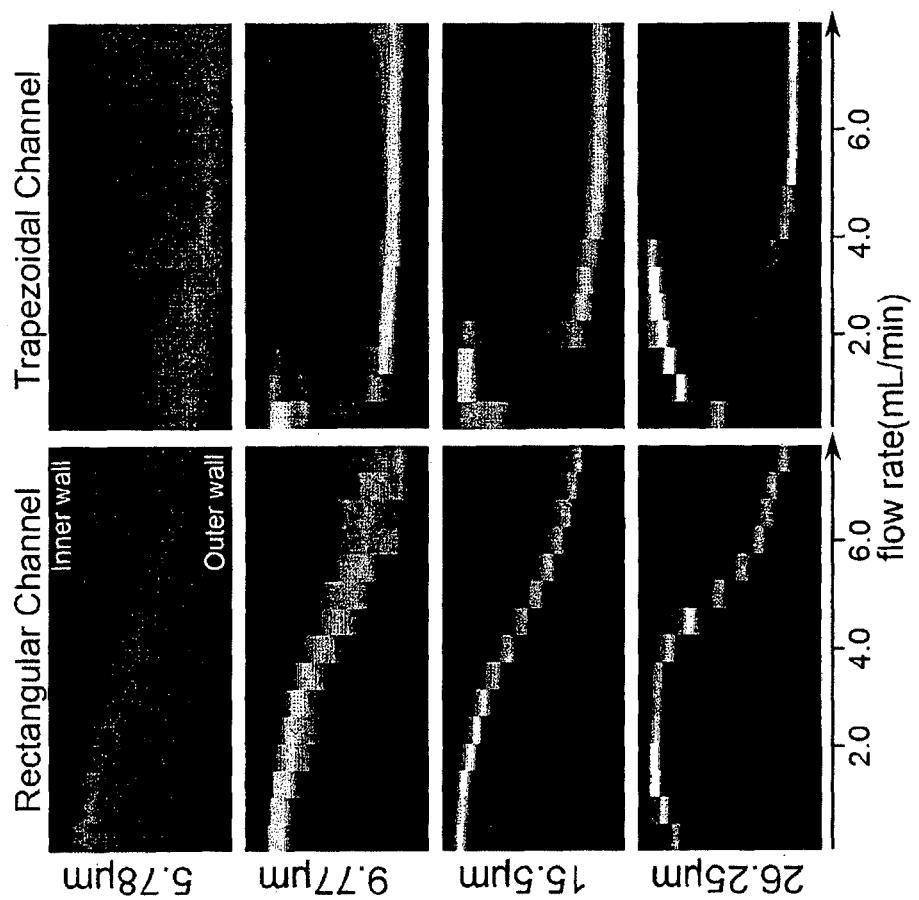
FIG. 10A is a top view image showing the comparison of fluorescent beads distribution at the outlet of a 80/130 μm inner/outer depth, trapezoidal cross section spiral microchannel, and a 80 μm height rectangular channel with flow rates ranging from 0.5 mL/min to 7.5 mL/min.

In a rectangular cross-section spiral channel, Dean vortices are symmetrical in the width direction, and particles are mostly focused at the inner side of the curved channel. Particles with diameter/height ratio ≥0.07 normally focus into two streams within the Dean vortex at the top and bottom halves of the channels. With increasing flow rate, the particle focusing position initially moves closer to the inner channel walls due to the increased inertial lift forces, while the centrifugal forces begin to dominate at higher flow rates pushing the particle position away from the inners walls towards the outer wall (FIG. 10A). This phenomenon limits the throughput and resolution of particle/cell separation, because the focusing positions of particles with different sizes are close to one another. See Kuntaegowdanahalli, et al. In a trapezoidal cross-section spiral channel, with inner walls shallower than the outer walls, the transition from the 'inertial-dominant' to the 'Dean-dominant' regime is sudden, therefore the focusing position immediately jumps from the inner half to the outer half of the channel. This is due to the evolution of a strong Dean vortex core skewed towards the outer half of the microchannel (the deep region in FIG. 9A), rendering the Dean force field nonlinear. As the inertial lift forces are highly size dependent, particles/cells of different sizes shift from the inertial dominant to the Dean dominant regime at different flow rates. Using this principle, particles/cells of different sizes can be separated with greater spatial resolution than in a traditional rectangular cross-section microchannel.

Experiment

Microfluidic channels were cast from a polymethy methacrylate (PMMA) mold made by a precision milling process (Whits Technologies, Singapore). The design consists of a single inlet, two-outlet spiral channel with multiple loops and curvature radius of about 10 mm. The patterns were cast with Sylgard 184 Silicone Elastomer (PDMS) prepolymer mixed in a 10:1 ratio with the curing agent. After curing, the PDMS mold with patterns was peeled and plasma bonded to another 3 mm thick PDMS layer. Input and output ports were punched prior to bonding. For the observation of particle position from the side, the device was cut along the output section of the channel with about 2 mm distance and then a second cast was made by keeping the device vertical to a flat bottle container. Tubings were connected to the ports before the second cast to prevent PDMS mixer flow into the channel.

During testing, the microfluidic device was placed on an inverted microscope (Olympus X71) and fluorescence images were captured with a Phantom V9.1 camera (Vision Research Inc. USA) near the end of the channel. Input samples were made by diluting 1% solid fluorescent particles (Bangs Laboratories, Inc. USA) of different sizes with DI water and pumped into the channel under different flow rates with a NE-1000 syringe pump (New Era Pump Systems, Inc. USA) to observe the focusing positions. For evaluating the separation quality of the device, higher concentration particles of two different sizes were mixed.

Results and Discussion

Figures 11A, 11B, 11C:
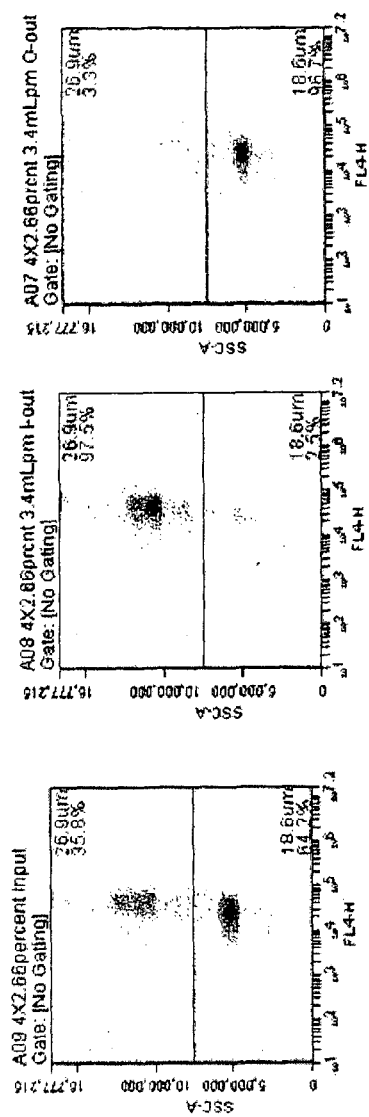
FIGS. 11A, 11B, and 11C are graphs of FACS results of particle separation with 80/130 μm inner/outer depth, 600 μm width trapezoidal cross spiral microchannel at 3.4 mL/min flow rate.

FIG. 10A shows the focusing bands of different sized particles with increasing flow rates as viewed from the top. The results clearly show the separation principle, with particle streams of different sizes shifting from the inner wall (inertial regime) to the outer wall (Dean regime) at different flow rate. For example, with a trapezoidal cross-section, at a flow rate of 1.5 mL/min, particles with >15.5 μm diameter can be separated from smaller ones by collecting from the inner and outer outlets. In the same channel, increasing the flow rate to 2.5 mL/min enables the separation of particles with >26.25 μm diameter from smaller ones. In comparison, in a rectangular channel, although particles of different sizes tend to focus at different positions in the channel at a certain flow rate, the distances between them are minimal and can be blurred if the particle/cell concentration is high, limiting the ability to process high hematocrit cell samples. FIGS. 11A-11C present the separation efficiency of two different size particles (16.68 μm and 26.9 μm) at an optimized flow rate of 3.4 mL/min. The purity of both outlets collection are over 96%, while throughputs of $8.85 \times 10^6$/min can be reached, which is 1.33% volume to volume concentration (equivalent to hematocrit number in blood samples).

Figure 10B:
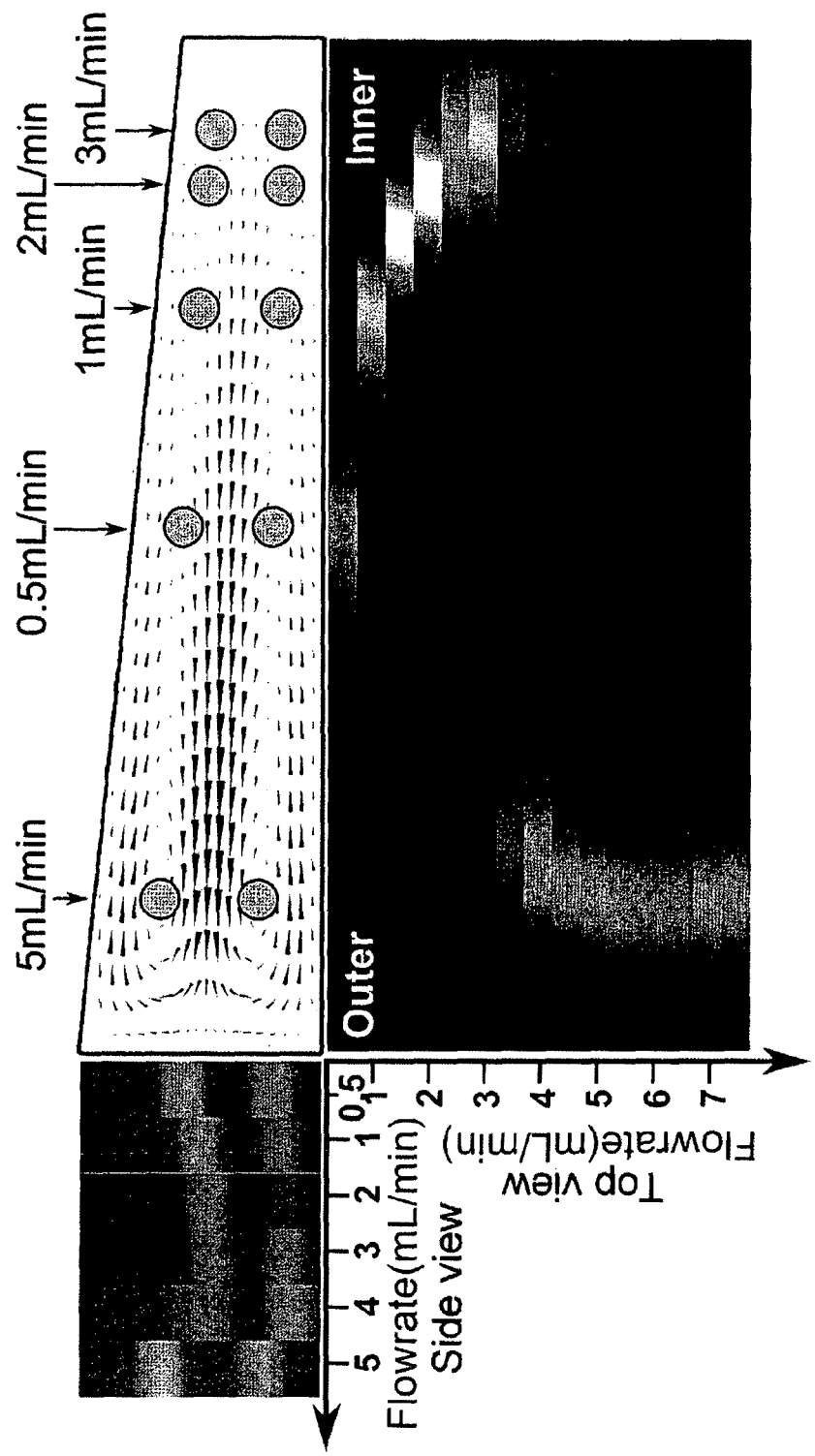
FIG. 10B is a CFD simulation of Dean flow field (inner/outer depth: 80/140 μm, width: 600 μm, flow rate: 3.5 mL/min, channel radius: 7.5 mm) combined with 26.25 μm fluorescent beads distribution from the top view and the side view, indicating the force balanced position of particles. Black cones indicate the direction and magnitude of Dean flow. Gray circles are positions of 26.25 μm beads at typical flow rates from experimental results.

Previously, particles were assumed to focus at the center of the channel depth in a spiral inertial microfluidic channel, since the Dean drag force ($F_D \propto U_f^2$, where $U_f$ is the average flow velocity) and the inertial force ($F_L \propto U_f^{1.63}$) are dominant at the center area of the channel cross section, while the centrifugal force ($F_C \propto U_f^2$) is neglected. But according to the experimental result shown in FIG. 10B, particles are focusing at two different depths. Numerical simulation indicates that only minor changes occur in the distribution of Dean flow field at different flow rates, and the maximum Dean flow velocity is always found at the center in the depth direction. At the positions of particle focusing (experimentally found to be between zero Dean line and zero lift force line), $F_D$ is mainly directed towards the inner wall, and is also much smaller than the maximum Dean force. In such conditions, $F_C$ cannot be neglected.

Figure 12:
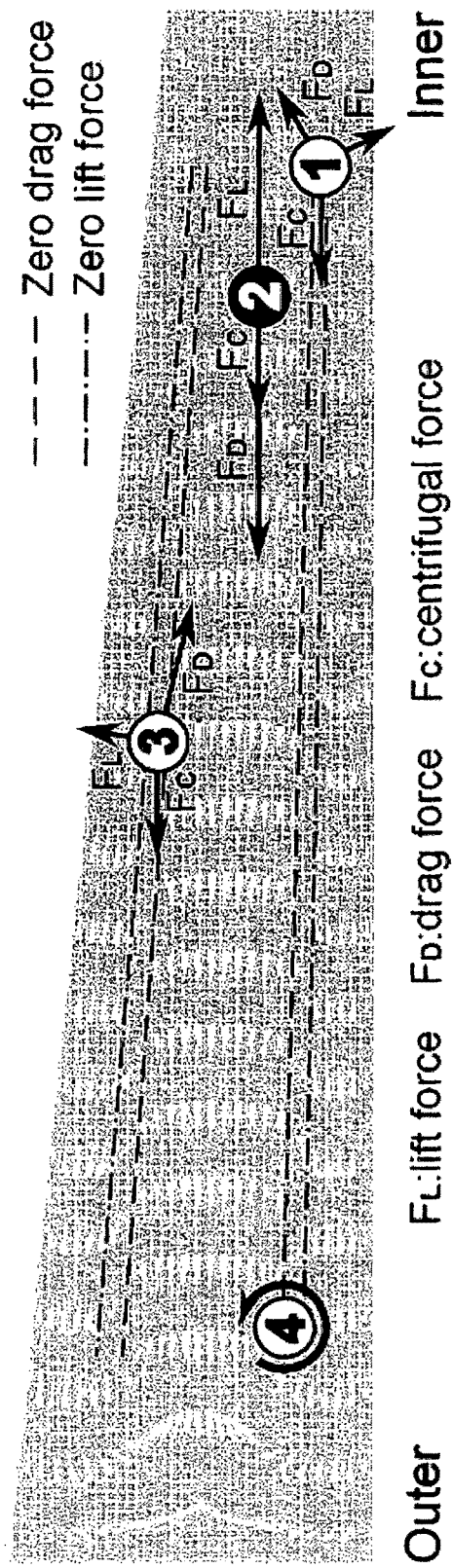
FIG. 12 is a schematic diagram illustrating the direction of forces on particles at different positions. Black circles indicate locations of unstable balanced point. White circles indicate stable force balanced points. White cones indicate the direction and logarithmic magnitude of Dean velocity.

FIG. 12 illustrates the forces that act on particles at different positions in the channel cross section. At Position #2, all the forces are in the channel width direction, but a slight disturbance along the channel depth direction will make $F_L$ change direction and increase in magnitude, which renders this point an unstable balance point. Position #3 is a stable force balance point at a low flow rate (0.5 mL/min). With the increase in flow rate, $F_L$ grows faster than $F_D$, and the particle balance point will have to move towards the top or bottom wall, which increases the component of $F_D$ to balance out increased $F_C$ (Position #1). If the flow rate continues to increase, $F_C$ will become dominant and no other forces can balance it laterally, therefore particles will move to the outer side and eventually will be trapped in one of the center vortices (Position #4) due to the strong Dean flow there. Since all of the forces are related to the size of the particles, the flow rate for them to shift from Position #1 to #4 is size-dependent, which makes size based separation possible.

Conclusion

A trapezoidal cross-section spiral microfluidic channel has been developed for size based particle separation. The experimental results show that the channel is able to achieve high resolution and high throughput cell separation. Particles were successfully separated between 16.68 μm and 26.9 μm particles at 1.33% concentration under a flow rate of 3.4 mL/min with over 96% efficiency, which is the highest throughput and efficiency among microfluidic methods so far. The mechanism of particle focusing was studied by observing the position of force balanced particle streams, along with numerical simulation of Dean flow field. The analysis indicates that particles are focusing at a location where the inertial lift force and the Dean drag force are not dominant, and that centrifugal force should be considered for the explanation of the particle force balance.

Example 2

Separation of Leukocytes From Blood Using a Spiral Channel with a Trapezoidal Cross-Section Inertial microfluidics has recently drawn wide attention as an efficient, high-throughput microfluidic cell separation method. However, the achieved separation resolution and throughput, as well as the issues with cell dispersion due to cell-cell interaction, have appeared to be limiting factors in the application of the technique to real-world samples such as blood and other biological fluids. A novel design of spiral inertial microfluidic (trapezoidal cross section) sorter with enhanced separation resolution is presented herein and its ability is demonstrated in separating/recovering polymorphonuclear leukocytes (PMNs) and mononuclear leukocytes (MNLs) from diluted human blood (1-2% hematocrit) with high efficiency (>80%). PMNs enriched by this method also showed negligible activation as compared to the original input sample, while conventional RBC lysis method clearly induced artificial activation to the sensitive PMNs. Therefore, this technique would be a promising alternative to enrich/separate sensitive blood cells for therapeutic or diagnostic applications.

Red blood cells (RBCs) or erythrocytes are the most abundant cell component in many biological fluids, including blood (where it makes up about 45% of the volume), bone marrow aspirate and peritoneal aspirate. Depletion of contaminating RBCs from those samples is often an indispensable sample preparation step before the application of any scientific, clinical and diagnostic tests due to various reasons. (See Guder, W. G., et al., 1st ed 1996, Darmstadt, Germany: GIT Verlag). For example, inadvertent lysis of RBCs releases hemoglobin, leading to chemical interference and deteriorating the PCR-based test performances. (See Al-Soud, W. A. and P. Rådström, Journal of Clinical Microbiology, 2001. 39(2): p. 485-493). Reports supporting the anti-proliferative and pro-apoptotic role of RBCs in primary cell culture of human cells have also been published. (See Fredriksson, K., et al., Scandinavian Journal of Immunology, 2004. 59(6): p. 559-565. and Atkin, S. L., et al., In Vitro Cell Dev Biol Anim, 1995. 31(9): p. 657-8). While the required degree of RBC removal varies widely depending on the downstream applications, avoiding artificial alteration on the phenotypes of sorted cells is an important criterion for all studies. This is especially important in the case of removing RBCs from human blood to isolate white blood cells (WBCs) or leukocytes, which play a key role in carrying out and mediating the immune response to various pathogens. The information extracted from the isolated leukocytes would be meaningful to facilitate disease prognosis only when the key features of leukocytes' original state are not masked by sample preparation artifacts.

Conventional methodologies for blood cell separation on the macroscale include differential centrifugation and selective RBC lysis. While the performance of differential centrifugation is affected by the blood source, especially for blood from individuals with diseases, such as recurrent infections (See Needham, P. L., Journal of Immunological Methods, 1986. 99: p. 283-284.), the RBC lysis method, which is usually used in combination with the centrifugation to get complete RBC removal, exposes the cells to hypotonic environment, altering cell metabolism in a cell type-specific manner. (See Selzner, N., et al., Cell Death and Differentiation 2004. 11: p. S172-S180). Besides, several cases have been reported stating that those sample preparation procedures could result in altered immuno-phenotype or impaired viability of the isolated WBCs. Moreover, the macroscale sample handling introduces variability to the separation and downstream application results due to imprecise control and non-uniform conditions, making the comparison of analogous results across different laboratories and platforms non trivial. (See Consortium, M.o.t. T. R., Nature Methods, 2005. 2(5): p. 351-356).

Several high-resolution, continuous microfluidic separation techniques (See Hou, H. W., et al., Micromachines, 2011. 2(3): p. 319-343; Toner, M. and D. Irimia, Blood-on-a-chip, in Annual Review of Biomedical Engineering 2005, Annual Reviews: Palo Alto. p. 77-103; Huang, L. R., et al., Science, 2004. 304(5673): p. 987-990; and Yamada, M., M. Nakashima, and M. Seki, Analytical Chemistry, 2004. 76(18): p. 5465-5471) utilizing size-dependent hydrodynamic effects have been reported to achieve the discrimination of few micrometers particle size differences, which is comparable to the intrinsic difference in size observed among blood cells (RBCs: 6~8 μm discoid; mononuclear leukocytes (MNLs): 7~10 μm sphere; polymorphonuclear leukocytes (PMNs): 10~12 μm sphere; WBCs include both MNLs and PMNs). (See Downey, G. P., et al., Journal of Applied Physiology, 1990. 69(5): p. 1767-1778 and Daniels, V. G., P. R. Wheater, and H. G. Burkitt, Functional histology: A text and colour atlas.1979, Edinburgh: Churchill Livingstone.) These approaches are considered to be promising alternatives to bypass the issues associated with macroscale blood cell separation methods mentioned above and are able to process the sample in a label-free and continuous manner. Size-based microfluidic separation techniques do not require the addition of any lytic agent or prior cell labeling treatment and allow better control of the microenvironment during the blood sample handling. The cell separation is achieved by driving individual cells uniformly through a microchannel with well-designed geometry, which leads to the alignment of cells in different positions across the channel width in a cell-size-dependent manner, followed by continuous sample collection at different outlets. The channel design is extremely critical for both the separation resolution and throughput, and differs as the working principle of the exact size-based hydrodynamic effects varies. In one example, a "deterministic lateral displacement (DLD)" microchannel containing an array of microposts leads to differential lateral displacement for particles above or below the critical hydrodynamic diameter as a result of the asymmetric bifurcation of laminar flow around the microposts. (See Huang, L. R., et al., Science, 2004. 304(5673): p. 987-990). In another type of microfluidic device, "pinched-flow fractionation (PFF)" patterned with a contraction-expansion segment (See Yamada, M., M. Nakashima, and M. Seki, Analytical Chemistry, 2004. 76(18): p. 5465-5471), the parabolic velocity profile of laminar flow within the contraction region leads to the alignment of particles near the channel sidewall in a size-based manner, so that large particles with comparable diameter to the channel width of the contraction region stay closer to the middle streamlines, but smaller particles have their center closer to the channel sidewall. This difference in lateral positions of particles with varying size is further amplified upon entering the expansion region, resulting in efficient separation. Both techniques have the high resolution required for separating RBCs from other cell types but are severely limited in their practical application on clinical samples by the low processing throughput. On the other hand, inertial microfluidics-based techniques using Dean flows in curvilinear microchannels with rectangular cross-section has been reported to achieve high throughput size-based particle separation (See Di Carlo, D., et al., Proceedings of the National Academy of Sciences, 2007. 104(48): p.

18892-18897 (hereinafter "Di Carlo et al., 2007"); Bhagat, A. A. S., S. S. Kuntaegowdanahalli, and I. Papautsky, Lab on a Chip, 2008. 8(11): p. 1906-1914; Di Carlo, D., et al., Analytical Chemistry, 2008. 80(6): p. 2204-2211; Kuntaegowdanahalli, S. S., et al., Lab on a Chip, 2009. 9(20): p. 2973-2980 and Seo, J., M. H. Lean, and A. Kole, Applied Physics Letters, 2007. 91(3): p. 033901-3).

As described below, the separation resolution of curvilinear microchannels has been improved, while maintaining the high-throughput feature, by modifying the channel cross-section to be trapezoidal rather than rectangular, and its ability is demonstrated below for efficient RBC depletion from a human blood sample with negligible effects on PMN immuno-phenotype. Moreover, to fit the needs of processing samples with volume ranging from microliter to milliliter scale, the current design can directly process the diluted whole blood sample when the blood sample volume is on the order of a microliter, (e.g. fingerprick), and as a replacement for the RBC lysis method, it can also be used in combination with differential centrifugation to get pure WBCs with no sign of alteration in activation status of the sorted cells for a larger sample volume (e.g., about 1 mL). The trapezoidal cross-sectional spiral microchannel described herein can be used as a generic, highthroughput method for removing RBCs and enriching target cells from other biological fluids, such as harvesting mesenchymal stem cells (MSCs) from bone marrow aspirates.

Materials and Methods
Microchannel Fabrication

The trapezoid cross-sectional spiral channels were made of polydimethylsiloxane polymer (PDMS, Sylard 184 Silicone Elastomer Kit, Dow Corning, USA) using standard soft lithography techniques from a poly(methyl methacrylate) (PMMA) master template. The PMMA template master was fabricated by a milling process (Whits Technologies, Singapore) to meet the special requirements in cross-sectional geometry. Given the available milling machine capability, the actual pattern of the template mold had a tolerance of ±10 µm compared to the virtual design, and a surface roughness of $R_a$=0.8 µm. Subsequently, PDMS prepolymer mixed with curing agent in a 10:1 (w/w) ratio was then cast on the PMMA template master and cured under 80° C. for 2 hours to replicate the microchannel features. The cured PDMS molds were peeled off from the PMMA master and punched for the inlet and outlet reservoirs using a 1.5 mm-diameter biopsy punch. Finally, the PDMS molds were irreversibly bonded to another flat 0.5 cm-thick PDMS sheet following oxygen plasma treatment (Harrick Plasma Cleaner/Sterilizer, Harrick Plasma, Inc., USA), The resulting PDMS devices were cut at four different locations and the cross-sections were measured under microscope to determine the exact dimensions of the devices. The rectangular cross-sectional spiral channels were also fabricated in PDMS polymer, but by using a double molding process from an etched silicon wafer master (See Bhagat, A. A. S., et al., Lab on a Chip, 2011. 11(11): p. 1870-1878). Briefly, positive AZ4620 photoresist was first patterned on a 6-inch silicon wafer to define the microchannel features. Then, the patterned wafer was etched to the desired depth using deep reactive ion etching (DRIE), followed by residual photoresist removal using oxygen plasma treatment. Next, trichloro (1H,1H,2H,2H-perfluorooctyl)silane (Sigma-Aldrich, USA) was coated on the etched wafer for 1.5 hours (h) to assist PDMS mold release. PDMS liquid mixture with 5 parts of prepolymer and 1 part of curing agent was then poured onto the silicon wafer and cured under 80° C. for 2 hours. The resulting PDMS mold had channel features protruding from the surface and served as a master for subsequent PDMS molding. The silane treatment and PDMS curing was repeated with this PDMS master to get a negative replica. As a last step, the negative replica, with inlet and outlet reservoirs punched, was bonded to another PDMS substrate by standard plasma-assisted bonding.

Sample Preparation

For bead experiments, fluorescent polystyrene particles (1 wt. % solid content) with a diameter of 6 µm (5.518 µm±0.122 µm), 10 µm (10.3 µm±0.4 µm) (Polysciences, Inc., USA), or 15.5 µm (15.5 µm±1.52 µm, Bangs Laboratories, Inc.) were diluted in deionized water (0.1% volume fraction) containing 0.025 mg/mL PEG-PPG-PEG Pluronic® F-108 (Sigma-Aldrich, USA), respectively, serving as the input sample. The small amount of PEG-PEG-PEG Pluronic® F-108 added was not enough to change the viscosity and density of the fluid but minimized the non-specific adherence of the particles to the channel walls. (See Inglis, D. W., et al., Applied Physics Letters, 2004. 85(21): p. 5093-5095).

For experiments with blood samples, fresh human whole blood from healthy donors with sodium heparin as anti-coagulant was purchased from Research Blood Component, LLC (Boston, Mass., USA) and processed within 6 hours after collection to ensure viability of PMNs. The PMNs and MNLs were isolated using Mono-Poly Resolving Media (MP-RM; MP Biomedicals, LLC, USA). Briefly, a 15 mL centrifuge tube containing 3.5 mL of whole blood layer atop a 3 mL MP-RM layer was centrifuged under 300 g for 30 min with brakes off. The bands of cells containing MNLs and PMNs were collected in separate tubes, washed and resuspended in sample buffer (1× PBS with 0.5% BSA), respectively. The isolated MNLs and PMNs could also be mixed together, serving as the representative WBC sample isolated via differential centrifugation. WBCs isolated using selective RBC lysis method were obtained by treating whole blood with RBC lysis buffer (eBioscience Inc., USA) (1:10) for 10 minutes, followed by washing and resuspension in sample buffer. Finally, for blood samples, whole blood was spun down at 400 g for 10 minutes with brake off to obtain the cell and plasma fractions. The cell fraction was then resuspended in sample buffer and adjusted to varying hematocrits (0.5-2% hematocrit) to constitute the various samples.

Device Characterization

The device was mounted on an inverted phase contrast/epifluorescence microscope (Olympus IX71, Olympus Inc., USA) equipped with a 12-bit CCD camera (C4742-80-12AG, Hamamatsu Photonics K.K., Japan). Samples were loaded within a syringe and pumped through the microchannel at varying flow rates using a syringe pump (Harvard Apparatus PHD 2000, Harvard Apparatus Inc., USA). To prevent the particle/cell sedimentation, a small magnetic stir bar placed inside the syringe was agitated during sample processing. Using ImageJ ® software, the positions of fluorescent particles within the channel cross-section were determined by taking the average fluorescence intensity of the image series. For cells, high speed videos captured using a high-speed camera, Phantom v9.1 (Vision Research Inc., USA) under phase contrast were analyzed to determine the cell positions. The standard deviation of light intensity of the high speed video was calculated to visualize the positions of fast moving cells.

FACS Analysis

All antibodies were purchased from BD Pharmingen™ (BD Biosciences, USA). To determine the separation efficiency, whole blood was stained with 0.1 mg/ml Hoechst 33342 (Invitrogen, USA) and FITC-conjugated mouse anti-human CD66b monoclonal antibody (1:25 v/v) for 30 minutes at 4° C. in the dark. The stained blood cell fraction was then collected by centrifugation and resuspended in sample buffer to the desired hematocrit as the input sample. Both the input sample and the output samples from two outlets were collected and analyzed on BD™ LSR II flow cytometer (BD Biosciences, USA) to determine the WBCs (Hoechst-positive cells) and PMNs (CD66b-positive cells) in each sample. Given the fact that MNLs comprise various cell types and there are no convenient surface markers available to determine the total amount of MNLs, the MNL count was based on the number of Hoechst-positive but CD66b-negative cells. Additionally, the RBC concentration was further measured by Z2 Coulter counter (Beckman Coulter Inc, USA). Similarly, to evaluate the device performance on buffy coat sample, WBCs isolated by centrifugation with MP-RM were stained for surface marker, CD66b, and nucleus. The stained WBCs were then resuspended in sample buffer with the same volume of the initial whole blood volume and processed by the device. Next, the size distribution of cells in the sample was measured by Z2 Coulter counter and a flow cytometer was used to analyze the sample composition.

For comparison between different RBC removal techniques, whole blood (without staining) was diluted to 1% hematocrit in sample buffer and then processed by the microchannel device. Subsequently, input and output samples of the device, as well as the WBCs isolated by differential centrifugation with MP-RM or by 10 minutes of hypotonic RBC lysis (methods described in the sample preparation section above), were stained with FITC-conjugated mouse anti-human CD66b monoclonal antibody (1:25 v/v) and APC-conjugated mouse anti-human CD18 monoclonal antibody (1:25 v/v) for 30 minutes at 4° C. in the dark. After staining, the samples were washed with sample buffer and analyzed on a flow cytometer. The gates for activated PMNs (i.e., CD18-positive PMNs), were drawn based on PMNs treated with 30 minutes of 1 μM phorbol 12-myristate 13-acetate (PMA; Sigma-Aldrich, USA) under 37° C. (complete activation achieved), followed with immunofluorescence staining and FACS analysis.

Nitro Blue Tetrazolium (NBT) Test

The WBCs isolated by differential centrifugation with MP-RM and the WBCs isolated by the spiral process with 1% hematocrit input sample were resuspended in sample buffer to a final concentration of about 1 million cells/mL. 40 μL of each cell sample was deposited onto Poly-L-lysine coated glass slide (Sigma-Aldrich, USA), respectively, where the sample region had been circled using Hydrophobic Barrier Pen (ImmEdge™ Pen, Vector Laboratories, Inc., USA). Samples on the slide were then incubated at 37° C. for 10 minutes to allow the cell attachment. The assay buffer for NBT test was freshly prepared and consisted of 1× $Ca^{2+}/Mg^{2+}$-containing DPBS buffer (Dulbecco's Phosphatase Buffered Saline; Invitrogen, USA) and 0.25% (w/w) NBT (Sigma-Aldrich, USA). For the conditions with PMA stimulation, the assay buffer also contained 1 μM PMA. After incubation, 40 μL of assay buffer was added onto the slide for 20 minutes of incubation at 37° C. Lastly, the cell sample was observed under phase contrast microscope (Olympus C10 (41, Olympus Inc., USA) and color images were taken by a DSLR camera (Canon EOS 500D, Canon, USA) with a 60× objective under microscope using a NDPL-1 (2×) connecting lens (Vivitar® Sakar International, Inc., USA).

Results and Discussion

Design Principle

When flowing through a microchannel, particles suspended in a fluid experienced inertial lift forces and viscous drag. Inertial lift forces include the shear-induced lift force resulting from the parabolic velocity profile of flows in a confined channel (See Di Carlo et al., 2007) and the wall-induced lift force arising from the disturbed rotational wake around the particles when close to the wall (See Zeng, L., S. Balachandar, and P. Fischer, Journal of Fluid Mechanics, 2005. 536: p. 1-25). For particles satisfying $a_p/D_h \geq 0.07$ (where $a_p$ represents particle diameter, and $D_h=4A/P$ is the microchannel hydraulic diameter, A and P are the area and perimeter of channel cross-section, respectively), the interplay between shear-induced and wall-induced lift forces leads to lateral migration of the initial randomly distributed particles to stable equilibrium positions around the microchannel periphery. (See Di Carlo, D., et al., 2007; Bhagat, A. A. S., S. S. Kuntaegowdanahalli, and I. Papautsky, Lab on a Chip, 2008. 8(11): p. 1906-1914 and Di Carlo, D., et al., Analytical Chemistry, 2008. 80(6): p. 2204-2211). Many studies revealed that the net inertial lift force ($F_L$) acting on the particles is highly dependent on particle size ($F_L \propto a_p^4$) and fluid shear rate ($F_L \propto G^2$). Apart from these, the resulting equilibrium positions are also affected by the geometry of the channel cross-section. Within a square cross-sectional straight microchannel, particles focus at 8 equilibrium positions in low Reynolds number flows ($Re_c<100$, where $$Re_c = \frac{\rho U_f D_h}{\mu}$$

and $\rho$, $U_f$, $\mu$ represent the density, velocity and viscosity of the fluid medium separately) but 4 equilibrium positions near channel corners when the Reynolds number is high ($Re_c \geq 500$). (See Chun, B. and A. J. C. Ladd, Physics of Fluids, 2006. 18(3): p. 031704). The asymmetric nature of the shear rate in a rectangular cross-sectional microchannel with high aspect ratio results in preferential focusing of particles along the longer channel dimension. (See Bhagat, A. A. S., S. S. Kuntaegowdanahalli, and I. Papautsky, Microfluidics and Nanofluidics, 2009. 7(2): p. 217-225). Incorporation of channel curvature could further modify the equilibrium positions by exerting viscous drag of secondary flow on particles. Fluid passing through a curved microchannel, such as a spiral channel, is subjected to centrifugal acceleration generating a secondary flow composed of two counter-rotating vortices (Dean vortices) across the channel cross-section. (See Dean, W. R., Philosophical Magazine Series 7, 1927. 4(20): p. 208-223 and 29. Dean, W. R., Philosophical Magazine Series 7, 1928. 5(30): p. 673-695). The magnitude of the vortex flow can be expressed using the non-dimensional Dean number (De) and the viscous force, known as Dean drag force ($F_D$), experienced by the particles can be quantified by assuming Stokes drag.

$$De = \frac{\rho U_f D_h}{\mu} \sqrt{\frac{D_h}{2R}} = Re_c \sqrt{\frac{D_h}{2R}} \quad (1)$$

$$F_D = 3\pi\mu U_D a_p = 5.4 \times 10^{-4} \pi \mu De^{1.63} a_p \quad (2)$$

where $U_D$ represents the average velocity of Dean flow given by $U_D=1.8\times10^{-4} De^{1.63}$. Notably, although it is not clearly indicated in the expression of Dean drag force, both its magnitude and direction varies within the channel cross-section since the secondary flow velocity differs at different locations of Dean vortices and is almost zero at the vortex core. (See Ookawara, S., et al., Chemical Engineering Science, 2007. 62(9): p. 2454-2465). While the inertial lift force primarily dictates the particle focusing, the combinatory effect of Dean drag force and inertial lift force within the spiral channel reduces the multiple equilibrium positions of particles into two vertically overlapping positions with the same lateral distance to the inner channel wall. (See Russom, A., et al., New Journal of Physics, 2009. 11: p. 075025). Furthermore, as a result of the size-dependence of both forces ($F_L \propto a_p^4$, $F_D \propto a_p$), particles with varying diameters occupy distinct lateral positions near the inner channel wall and demonstrate different degrees of focusing when flowing through the same spiral channel under a given flow rate. Thus the spiral microchannel can be applied as a possible size-based particle/cell separation device.

Figure 13:
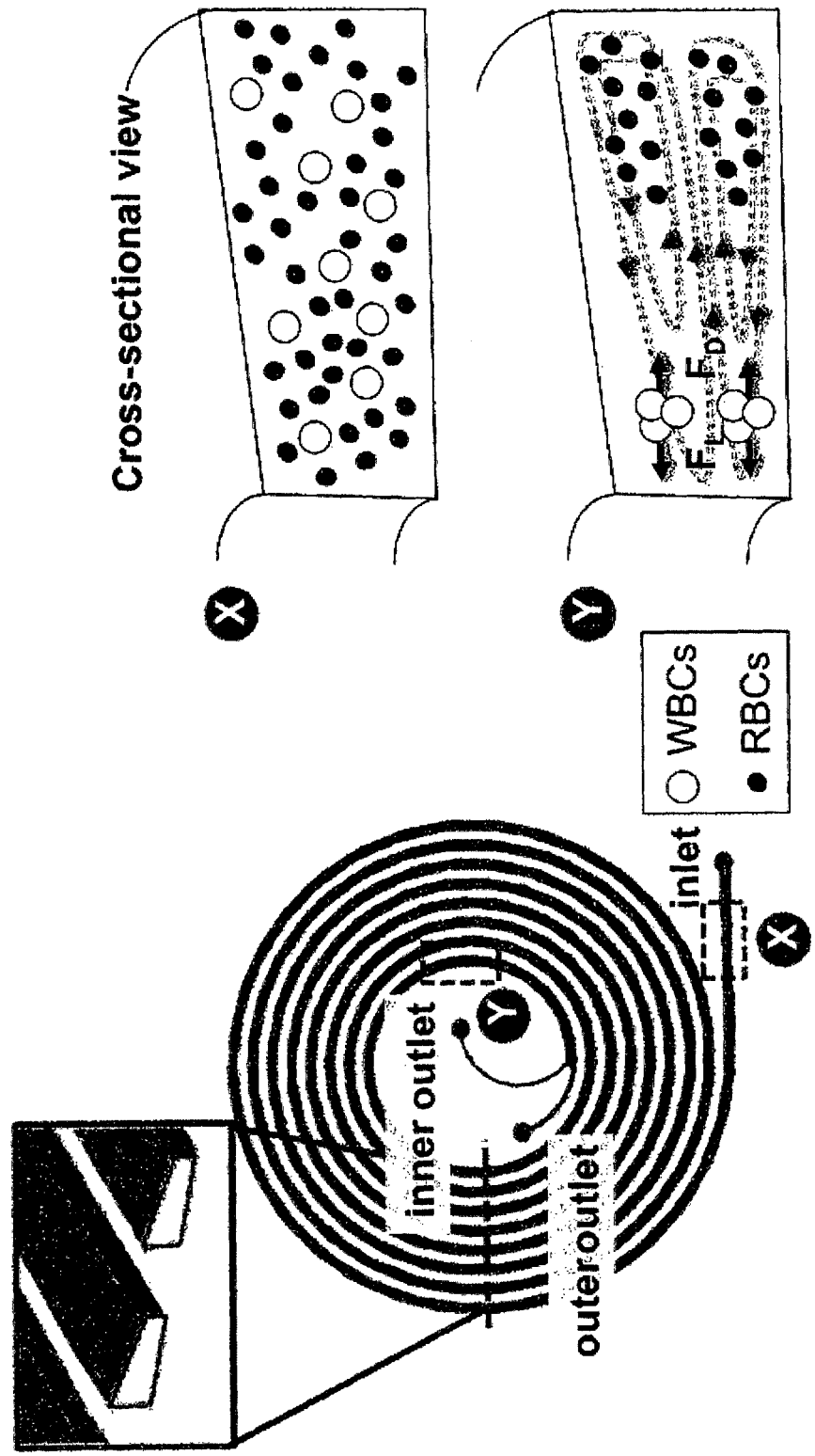
FIG. 13 is a schematic (not to scale) of a spiral channel with trapezoid cross-section of 500 μm width, 70 μm (inner) and 100 μm (outer) depth illustrating the operating principle. At the outlet, the larger white blood cells (WBCs) focus near to the inner wall due to the combination of inertial lift force ($F_L$) and Dean drag force ($F_D$), while the smaller red blood cells (RBCs) are trapped at the core of the Dean vortex and form a broad band near the outer wall.
Figures 14A, 14B, 14C, 14D:
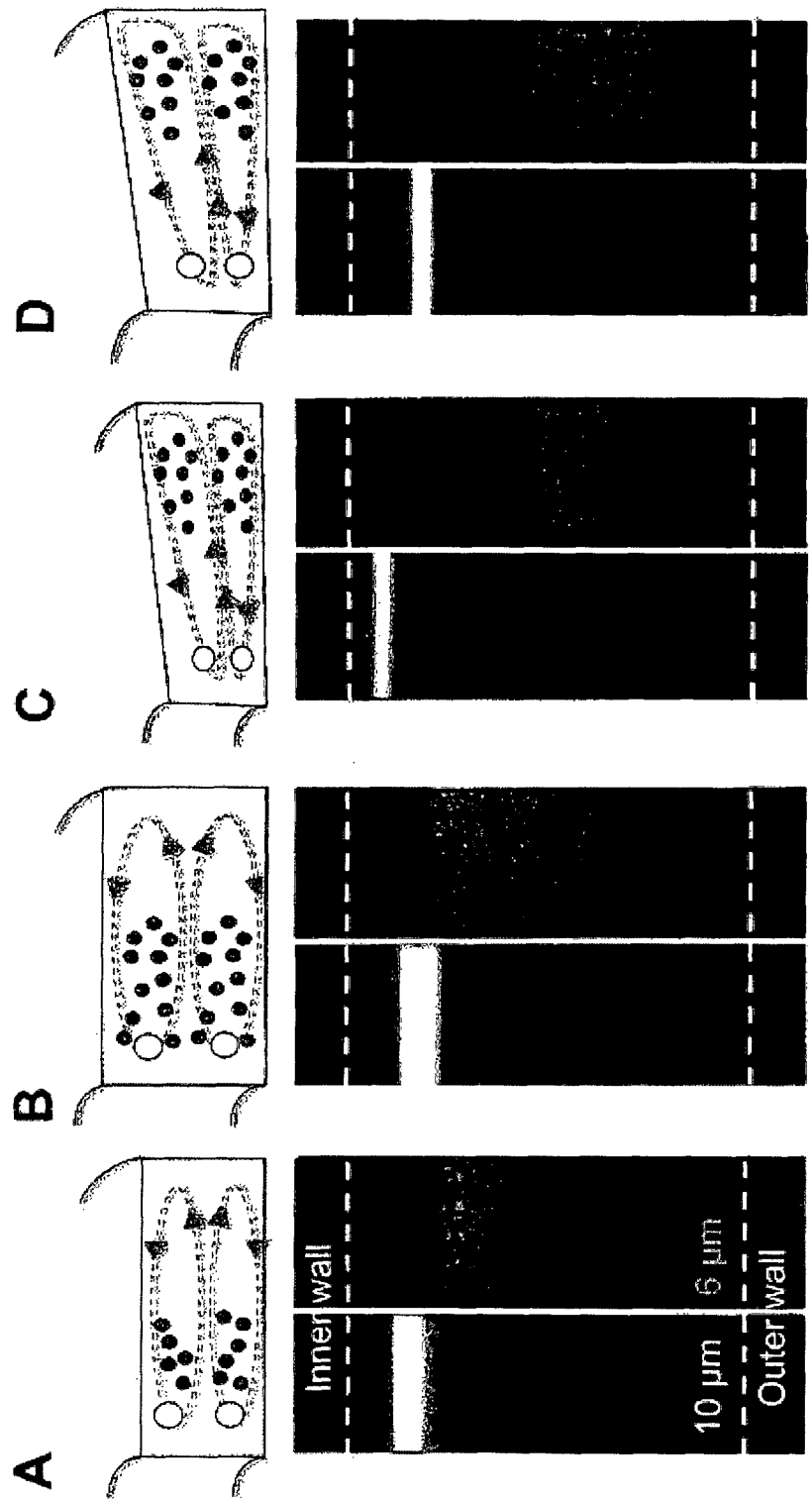
FIGS. 14A-14D are: schematic (not to scale) and average composite fluorescent images indicating the inertial focusing of 10 μm (white) and 6 μm (gray) beads in FIG. 14A) spiral channel with rectangular cross-section of 500 μm×90 μm (W×H) under optimal flow rate: 1 ml/min (De=4.31)

One major challenge of utilizing spiral microchannels in blood cell separation lies in the limited separation resolution and capacity of holding vast number of RBCs without affecting the separation efficiency. One recent work showed that polystyrene particles with a diameter of 7.32 9.92 μm, 15.02 μm and 20.66 μm, respectively, could focus into four distinct bands in a spiral microchannel with 500 μm×100 μm (W×H) rectangular cross-section at De=16.3, at a very low concentration (0.005% volume fraction particle solution). (See Chatterjee, A., S. S. Kuntaegowdanahalli, and I. Papautsky, Proceedings of the SPIE, 2011. 7929: p. 792907). However, this design cannot be directly applied to blood samples where the vast number of RBCs significantly broaden the stream width of RBCs due to cell-cell interactions and affect the focusing of other cells. To accommodate the samples with higher hematocrit, the spacing between equilibrium positions needs to be increased. The approach presented herein is to modify the spiral microchannel cross-section into a trapezoid with higher channel depth on the outer channel wall, as shown in FIG. 13. The asymmetry of the trapezoidal cross-section alters the shape of the velocity field and results in the formation of strong Dean vortex cores skewed towards the outer wall with larger channel depth even at relatively low flow rates. Therefore, while in a spiral with a rectangular cross-section the interplay between the inertial lift force and the Dean drag force leads to the focusing of large particles close to the inner wall and the trapping of small particles at the core of Dean vortices located at the center of the channel width, the modified velocity field of a spiral with a trapezoidal cross-section leads to a greater shift for small particles towards the outer wall without affecting the focusing position of large particles, thus providing a greater difference in equilibrium positions between them, resulting in higher separation resolution, as shown in FIGS. 14A-14D.

Figures 15A, 15B, 15C:
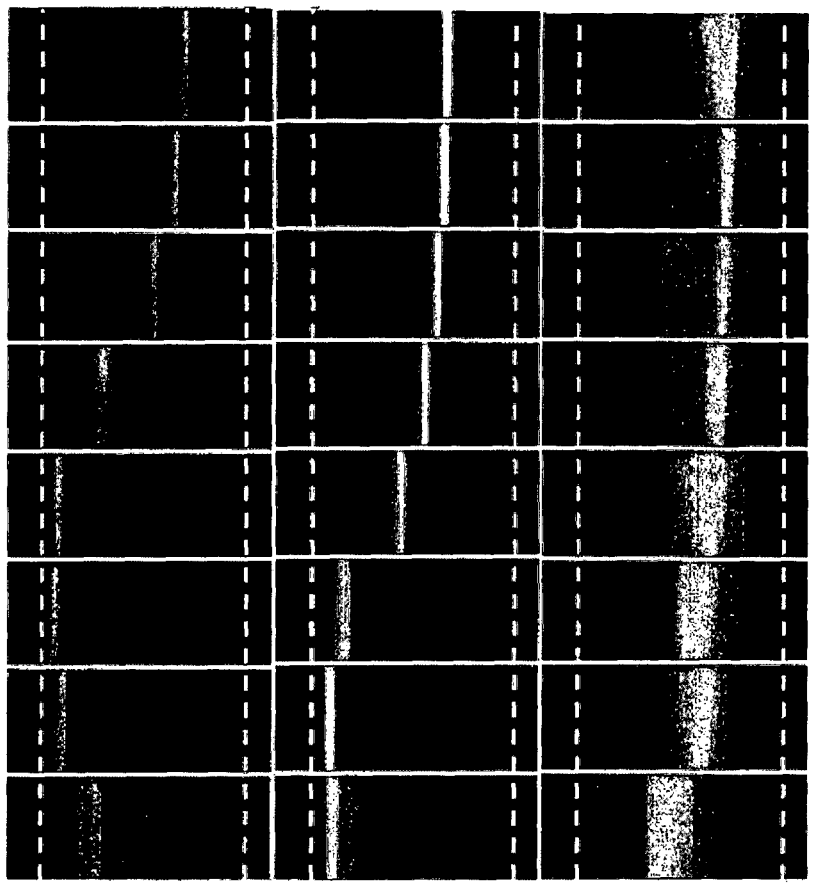
FIGS. 15A-15C are top-down view images demonstrating the focusing behavior of fluorescent particles as a function of flow rate (Q) inside spiral channel with trapezoid cross-section of 500 μm width, 70 μm (inner) and 100 μm (outer) depth.

The trapezoidal cross-section also has an impact on the size- and flow-rate-dependence of particle focusing. In a rectangular cross-sectional spiral, particles with $a_p/D_h \geq 0.07$ initially focus near the inner channel wall at low $Re_c$, and then move towards the outer wall as $Re_c$ increases. When $Re_c$ is sufficiently high, Dean drag force dominates the particle behavior leading to defocusing of particles. On the contrary, the results presented herein indicate that instead of $D_h$, the channel depth at the inner wall ($D_{inner}$) serves as a better critical channel dimension to determine whether particles of a certain diameter can form a focused stream near the inner wall. This was confirmed by using trapezoid channels satisfying a $D_{outer}/D_{inner} \leq 1.5$ criterion as shown in FIGS. 15A-15C. Interestingly, while the particle behavior of trapezoidal cross-section spiral displays a similar focusing/defocusing dependence on $Re_c$, an additional regime featured by the trapping of particles within the outer half of the channel cross-section was observed when $Re_c$ increased further. Moreover, the flow rate required to trap particles increases with particle size, making the isolation of particles within a specific size range feasible. The exact mechanism of particle trapping under high $Re_c$ remains elusive. Previous research has revealed that the position of the focused particle stream is affected significantly both by the direction and magnitude of $F_D$ acting on particles (See Ookawara, S., et al., Chemical Engineering Journal, 2004. 101(1-3): p. 171-178), while $F_L$ was the primary force dictating particle focusing in low $Re_c$ flow. (See Russom, A., et al., New Journal of Physics, 2009. 11: p. 075025). The altered velocity field within trapezoid cross-sectional spiral might lead to a skewed Dean vortex profile, acting as a particle trap at the core of the vortex. As a result, at low $Re_c$ the large particles can escape the Dean vortex cores experiencing small $F_D$ and be able to find their lateral equilibrium position primarily determined by spatial distribution of $F_L$. Further study on the inertial focusing of trapezoidal cross-sectional spirals is necessary to validate this hypothesis.

Device Performance on Human Blood Samples

Figures 16A, 16B:
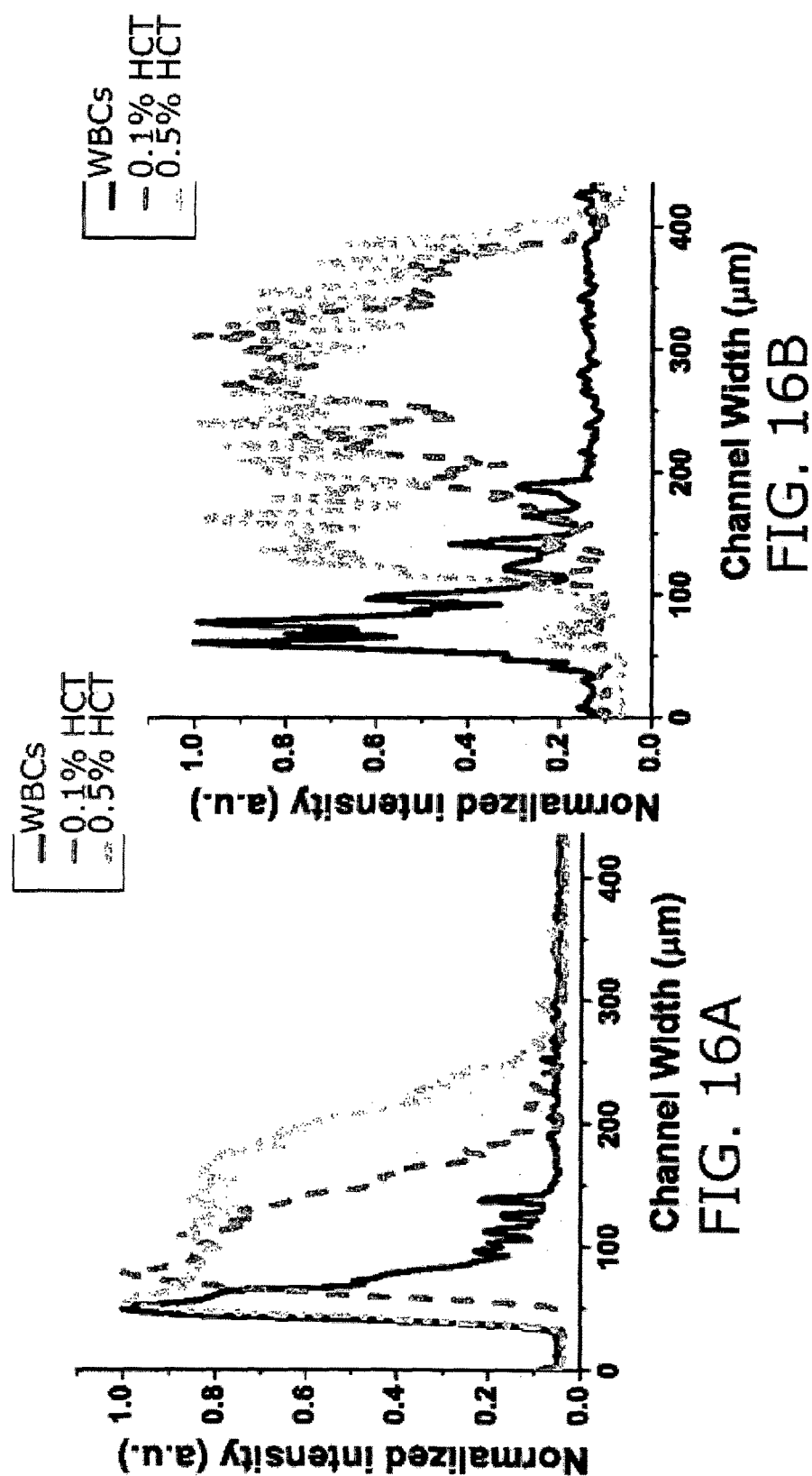
FIGS. 16A-16B are normalized intensity line scans indicating the distribution of WBCs and RBCs at different hematocrit (0.1%, 0.5%) across channel width of FIG. 16A) spiral channel with rectangular cross-section (500 μm×90 μm) under optimal flow rate (1 ml/min), or FIG. 16B) spiral channel with trapezoid cross-section (500 μm×70/100 μm) under optimal flow rate (0.8 ml/min). The inner channel wall is represented by x=0, and the outer channel wall is represented by x=500.
Figure 17B:
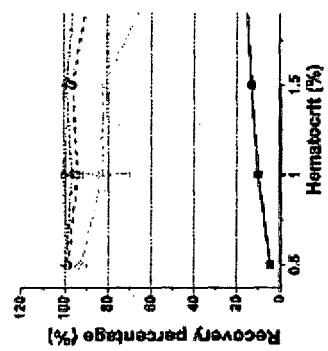
FIGS. 17A-17D are characterizations of blood cells in a spiral channel with a trapezoidal cross-section.
Figure 17D:
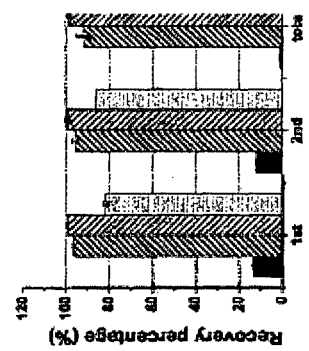
Figure 17A:
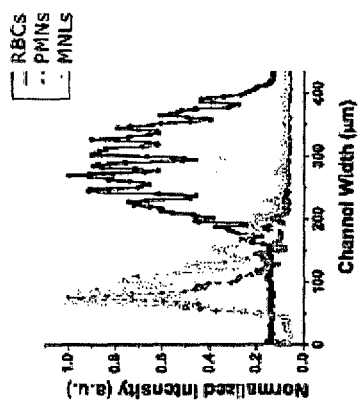
Figure 17C:
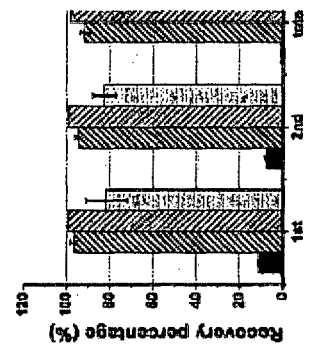

The optimized PDMS device for RBC removal developed herein consists of a 1-inlet, 2-outlet spiral microchannel with a trapezoidal cross-section of 500 μm width (485.00 μm±2.31 μm), 70 μm (inner wall, 72.84 μm±1.16 μm) and 100 μm (outer wall, 102.65 μm±3.55 μm) depth. Near the outlet region, the 485 μm wide channel was split into two outlet channels with a channel width ratio of 3:7 (inner: outer), while their channel lengths were adjusted to be equal with each other. The inner outlet was defined to be the WBC outlet with RBC-depleted sample (i.e., PMNs/MNLs) and the outer outlet to be the RBC waste outlet The optimal flow rate was experimentally determined to be 0.8 mL/min ($Re_c$=46.52; De=4.22). PMNs and MNLs isolated via centrifugation using MP-RM were injected through the device separately to determine their equilibrium positions inside the channel, shown in FIG. 17A. Under optimal flow rate, PMNs formed a focused stream at a distance of about 75 μm away from the inner channel wall in the top-down view, and MNLs occupied a similar lateral position but had a slightly wider stream width presumably due to the smaller cell size. On the contrary, RBCs with much smaller cell size displayed as a broad stream near the outer channel wall, enabling the isolation of PMNs/MNLs from RBCs at the device outlets. Compared to conventional rectangular cross-sectional spiral microchannel, shown in FIG. 16A, where the distribution of WBCs significantly overlaid with that of RBCs for input samples of ≥0.1% hematocrit, the developed trapezoidal cross-sectional spiral achieved a larger spacing between WBCs and RBCs, as shown in FIG. 16B, therefore allowing it to process input samples with higher hematocrit without compromising the purity and recovery of isolated WBCs. FIG. 17B shows the recovery of blood components from the WBC outlet of the present device after a single pass, where optimal performance was achieved for a 0.5% hematocrit blood sample with about 95% RBC removal and 98.4% of total WBC recovery (99.4% PMN recovery and 92.4% MNL recovery). Under this condition, the device's throughput translates to about 10 μL of whole blood (45% hematocrit) per minute which is significantly higher than other microfluidic leukocyte isolation devices, such as "hydrodynamic filtration" with about 29 fold WBC enrichment at 20 μL/min for 10-fold diluted blood (See Yamada, M. and M. Seki, Lab on a Chip, 2005. 5(11): p. 1233-1239), dielectrophoretic (DEP) microseparator with 92% WBC recovery at 50 μL/hr (See Han, K.-H. and A. B. Frazier, Lab on a Chip, 2008. 8(7): p. 1079-1086), and magnetophoretic microsparator with 97% WBC recovery at 2.5~20 μL/hr (See Han, K.-H. and A. B. Frazier, Lab on a Chip, 2006. 6(2): p. 265-273). Further increase in input sample hematocrit would broaden the distribution of RBCs across the channel width, leading to a decrease in both RBC removal, but the total WBC recovery and PMN recovery remained relatively constant. Up to 1.5% hematocrit, the device can still achieve 86.8% RBC removal and 96.2% of total WBC recovery. A 2-stage process, where the output sample from the WBC outlet of the first device was used as the input of the second device without any dilution, achieved high RBC removal while maintaining good WBC recovery for 1%-1.5% hematocrit samples, as shown in FIGS. 17C and 17D. Since WBCs collected from the first stage were concentrated by a factor of about 6, one can easily process 500 μL of whole blood with the 2-stage process in less than 25 min, which is comparable to the microfluidic RBC lysis device reported by Sethu et al. (See Sethu, P., et al., Analytical Chemistry, 2006. 78(15): p. 5453-5461.)

The device can also be used as a secondary step of differential centrifugation, whose performance was subjected to variance of blood source and manual transfer of different cell layers to different tubes. It is often the case that some RBC residuals stay with the isolated WBCs after the first 30-min centrifugation and additional slow centrifugation washing steps or RBC lysis step are required for further RBC removal. Here, the RBC removing ability of this device was demonstrated in processing buffy coat in a case where notable amounts of RBCs were isolated along with WBCs by centrifugation (FIGS. 18A and 18B). Based on the size distribution of cell sample, it was observed that the WBC percentage (cell diameter: 6.6-15 μm) among the whole population increased from 30% to 91% after processing by this device.

Effect of RBC Removal Techniques on the Immune-Phenotype of PMNs

Figures 19A, 19B:
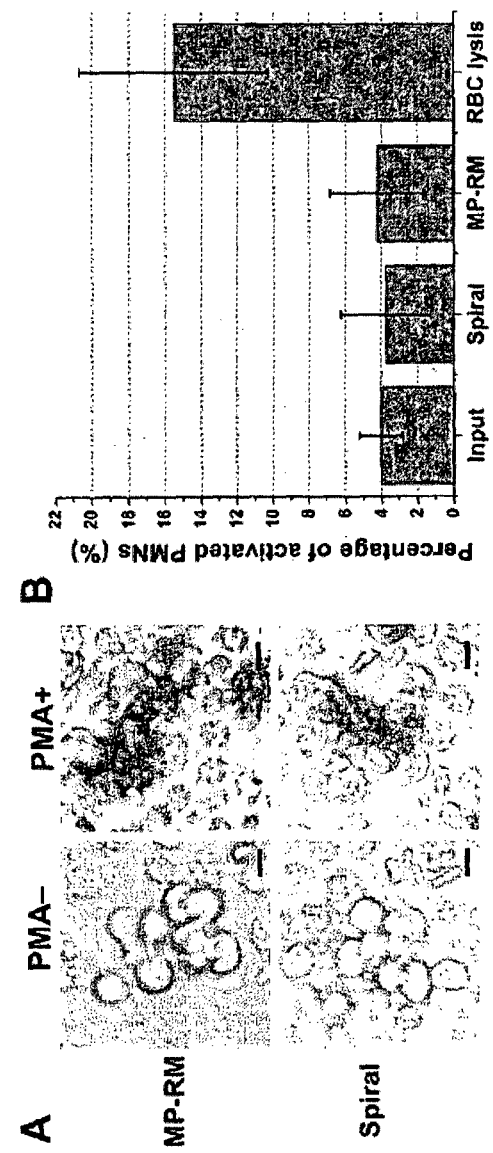
FIGS. 19A-19B are illustrations of comparisons of PMN activation by spiral and other RBC removal techniques.

Gentle depletion of RBCs from a sample is crucial for the downstream analysis of remaining cells. In a recent study, the overall gene expression profile and cell viability was measured for cancer cells, MCF7, after inertial separation under $Re_c$=21 and no significant effects caused by the separation process were observed compared to the unsorted control sample (See Hur, S. C., et al., Lab on a Chip, 2011. 11(5): p. 912-920), indicating that transient exposure of cells to a shear condition in a short time scale might not be enough to change the cell function. For the spiral device described here, the viability of isolated WBCs was found to be 98.22%±0.83% (trypan blue staining; input: 98.05%±1.08%) and their ability of producing reactive oxygen species in response to in vitro stimuli (PMA) has been measured by the NBT test. As shown in FIG. 19A, PMNs isolated by both spiral process and differential centrifugation remained passive but were able to reduce NBT in the presence of 1 μM PMA. Given the high sensitivity of white blood cells to external stimuli, the inventors compared the effect of different RBC removal techniques on the expression level of cell surface marker (FIG. 19B), CD18, which is a classical activation marker for PMNs. Both spiral process and centrifugation using MP-RM had negligible effect on PMN activation, whereas the RBC lysis method increased the percentage of activated PMNs significantly and could potentially affect the phenotype and gene expression profile.

Conclusions

A novel, high-throughput RBC removal technique has been developed using a trapezoidal cross-sectional spiral, which provides higher resolution separation as compared to a rectangular cross-section with similar dimensions, as shown by an experimental demonstration where the asymmetry velocity field within a trapezoidal spiral channel affects the inertial focusing phenomenon, indicating the feasibility of using channel cross-sectional geometry (other than width and depth) as a parameter for optimization of a curvilinear inertial microfluidic sorter. This size-based separation technique eliminates the need for long-term exposure of blood cells to nonphysiological conditions and thus minimizes artificial alterations on cellular phenotypes during separation. While clogging and low throughput are major drawbacks for most microfluidic size-based separation methods which utilize membranes (See Bruil, A., et al., Journal of Biomedical Materials Research, 1991. 25(12): p. 1459-1480) or micron-sized pillars (See Panaro, N. J., et al., Biomolecular Engineering, 2005. 21(6): p. 157-162), the relatively large dimensions of the device described above enable large volume sample processing with no clogging issues. As compared to other types of continuous cell separation methods, such as DLD and PFF techniques, the spiral microchannel described above functions at a high operational flow rate (in the mL/min range) with large channel dimensions accommodating the abundant RBCs (up to about 2% HCT), and thus possesses high throughput and is amenable to process blood samples. The highly repeatable performance and ability in enriching WBCs to >90% of total cell population also makes it a good choice to completely deplete RBCs from various biological fluids when used alone or in combination with differential centrifugation. Further optimization of channel cross-section and other structural features is possible to apply this technique to many other primary cell separation problems.

Example 3

Spiral Microchannel With Rectangular and Trapezoidal Cross-Sections for Size Based Particle Separation A method for three-dimensional observation of the location of focused particle streams along both the depth and width of the channel cross-section in spiral inertial microfluidic systems is described below. The results confirm that particles are focused near the top and bottom walls of the microchannel cross-section, revealing clear insights on the focusing and separation mechanism. Based on this detailed understanding of the force balance, a novel spiral microchannel with a trapezoidal cross-section is introduced that generates stronger Dean vortices at the outer half of the channel. Experiments show that particles focusing in such device are sensitive to particle size and flow rate, and exhibit a sharp transition from the inner half to the outer half equilibrium positions at a size-dependent critical flow rate. As particle equilibration positions are well segregated based on different focusing mechanisms, a higher separation resolution is achieved over spiral microchannels with rectangular cross-section.

Figure 20:
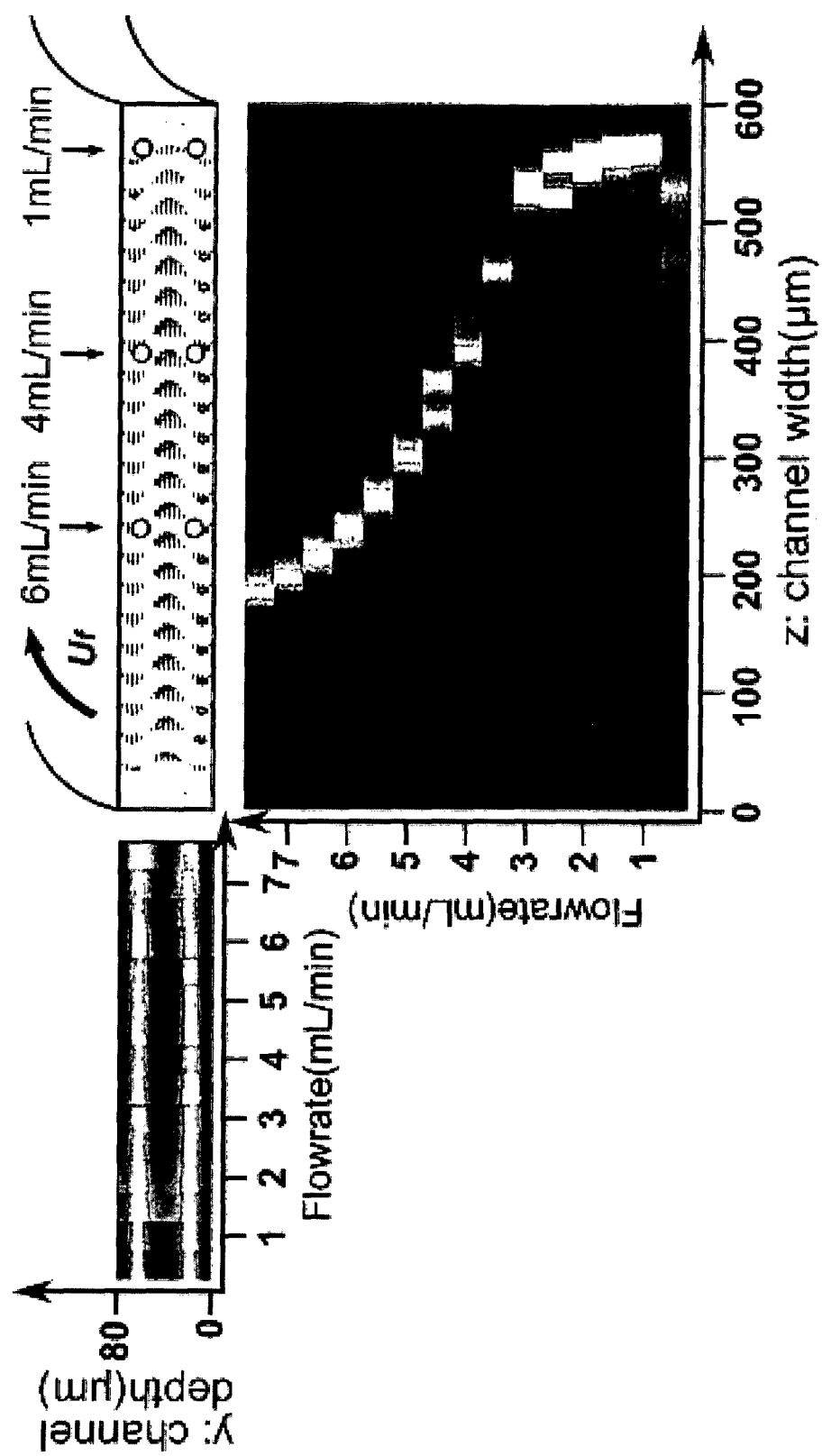
FIG. 20 is an illustration of balance of particles in a rectangular cross-section spiral microchannel. The black cones within channel cross-section are the CFD simulation result of the Dean flow field at a flow rate of 3.5 mL/min in a channel with radius 7.5 mm. The figure also shows the vector plot of the Dean drag force on the particle since the force is proportional to the Dean velocity. The experimental images of 15.5 µm fluorescent beads distribution from the top view and side view are placed at the bottom and to the left side of the simulation profile. By combining the top- and side-view observations, the positions of 15.5 µm beads at typical flow rate are drawn as gray circles in the channel cross-section.

Particle focusing positions in rectangular and trapezoidal cross-section spiral channels FIG. 20 shows the focusing positions of 15.5 μm particles from the top and side view in a spiral channel with a 80 μm×600 μm (H×W) rectangular cross-section. As seen from the top view, the focusing position of the particles moves gradually from the inner wall towards the outer wall with increasing flow. From the side view, two clear bands are observed along the depth direction, indicating two distinct focusing positions near the top and bottom walls. In contrast to the gradual change of focusing position along the width direction, the focusing position along the depth direction is largely independent of the flow rate, and remains fixed at 22.0±1.1% of channel depth from the top and bottom walls for flow rates ranging from 0.5-7.5 mL/min. The result is in line with previous simulation and experimental work in straight rectangular or circular cross-section channel. From the simulated Dean flow profile, it is seen that the Dean flow changes its direction at 28±0.5%, indicating that the Dean drag force at the focusing position (depth) is always pointing to the inner wall. These results provide important insights into the focusing mechanism of particles moving in spiral channels. Detailed force balance will be discussed below.

In a spiral channel with trapezoidal cross-section, the particle focusing behavior is different from that in a rectangular channel. In a trapezoidal channel, as shown in FIG. 21, particles focus near the inner channel wall at low flow rate (similar to channels with rectangular cross-section), while beyond a certain threshold flow rate, they suddenly switch to an equilibrium position located at the outer half. Careful examination of the focusing positions in the top and side view reveals that particles are trapped exactly at the centers of the two Dean vortices formed at the outer half of the channel.

Comparison of Top View Focusing

Figure 22:
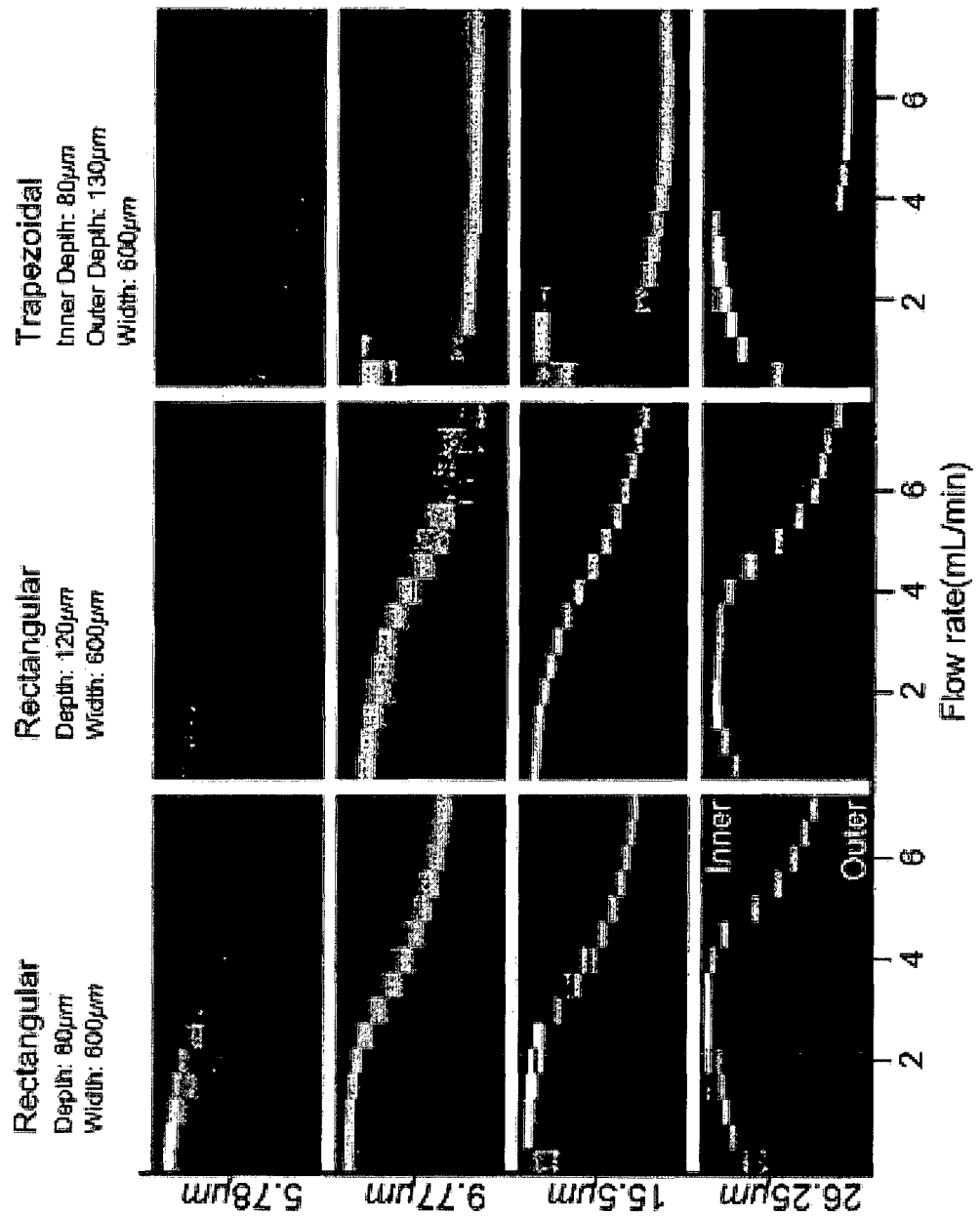
FIG. 22 is a top-view experimental observation of fluorescently labeled microparticles at the outlet of rectangular cross-section spiral microchannels with different channel depths and a trapezoidal cross-section spiral microchannel for increasing flow rates.

FIG. 22 shows the flow rate dependence of the focusing position of fluorescent particles in a spiral channel with rectangular and trapezoidal cross-sections. The diameters of the particles were 5.78 µm, 9.77 µm, 15.5 µm, and 26.25 µm respectively. The cross-sections of the rectangular channel were 80 µm×600 µm (H×W) and 120 µm×600 µm (H×W) respectively. The width of trapezoidal channel was fixed at 600 µm, and the depths at the inner and outer side of the channel are 80 µm and 130 µm, respectively. The results shown in FIG. 22 demonstrate that in the rectangular channels, particles were focused near the inner channel wall at low flow rate, and then the focusing position started to gradually move towards the outer wall as the flow rate increases. At a given flow rate, particles of varying sizes occupied different positions within the channel cross-section. This phenomenon was utilized by Kuntaegowdanahalli to demonstrate size-based separation with multi-outlets bifurcations at the end of the channel. However, since the difference in focusing positions between the particles is not significant, the resolution and throughput of separation of concentrated suspensions is limited.

Measurements of the focusing position of particles with different sizes in trapezoidal channel demonstrate clearly distinct characteristics. As shown in FIG. 22, for all the particles, there was a narrow flow rate range, i.e. a threshold, to 'switch' from inner side to the outer side of the channel as the flow rate increases. Below the threshold flow rate, particles were focused near the inner wall, while above the threshold, they were focused near the outer side of the channel. It is important to note that this threshold flow rate was a function of particle size. In particular, the 5.78 µm and 9.77 µm particles, which are smaller, shifted to the outer half of the channel at very low (<=1 ml/min) flow rate while the 15.5 µm and 26.25 µm particles remained focused near the inner wall at such low flow rate. Increasing the flow rate had no effect on the smaller particles (5.78 µm and 9.77 µm) once they were focused at the outer side. However, the 15.5 µm particles equilibrated at the outer side above 2.0 mL/min, while the 26.25 µm particles migrated at flow rates greater than 3.5 mL/min.

Separation Resolution and Throughput

For the separation of particles of two different sizes, the ideal scenario is for particles of different sizes to focus at positions as far as possible from each other. This will not only increase the separation resolution, but also allows one to process samples with higher particle concentrations by minimizing the interaction between particles of different sizes (e.g., high hematocrit cell solutions in the case of blood separation). The results in FIG. 22 demonstrate that the trapezoidal cross-section channel met these requirements. Next, tests were conducted to show actual separations between particles of varying sizes.

Figure 23:
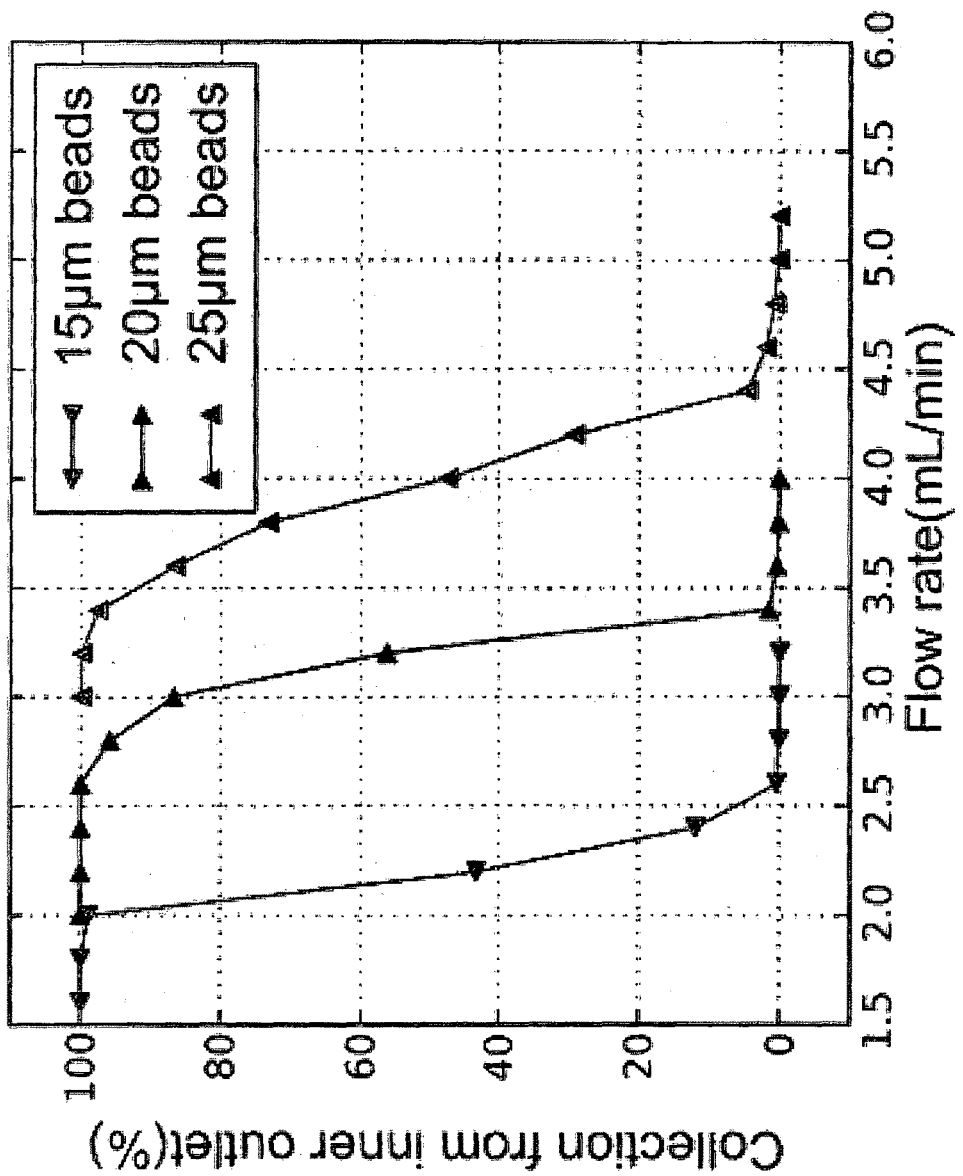
FIG. 23 is a graph of the collection from the inner outlet (%) as a function of flow rate (mL/min) showing the collection ratio of particles from the inner outlet of trapezoidal cross-section spiral channel (80 µm inner depth and 130 µm outer depth, 600 µm wide) at different flow rates for various particle sizes.

FIG. 23 presents the collection of different standard National Institute of Standards and Technology (NIST) traceable particles (nominal diameter 15 µm, 20 µm and 25 µm, mean diameter 15.61 µm, 20.85 µm and 25.63 µm, Bangs Laboratories, Inc. USA) diluted to 150-350 k/mL concentration and pumped through the spiral microchannel with trapezoidal cross-section. The outlet samples were collected and analyzed for particle recovery. The ratio of collected volumes from inner outlet and outer outlet was 1:4. The results showed that the suitable range of flow rate for the particles to migrate from the inner side to the outer half completely was between 2.0-2.6 mL/min for 15 µm beads, 2.6-3.4 mL/min for 20 µm beads and 3.4-4.8 mL/min for 25 µm beads. These data indicate that the flow rate threshold was sufficient to separate these three groups of particles with high separation resolution.

The high throughput separation capability of trapezoidal channels is presented in FIGS. 24A-24B with fluorescently labeled particles which have different mean diameters. The scatter plots in FIG. 24A indicate two groups of particles and their separation efficiency. The separation results of 15.5 µm and 18.68 µm beads at $1.61 \times 10^7$/min (1.87% volume concentration, equivalent to 'hematocrit number' in blood separation) throughput indicates over 92% separation efficiency. The separation results of 18.68 µm and 26.9 µm at an optimized flow rate of 3.4 mL/min show that the purity of both outlets was over 96%, with a total throughput of $8.85 \times 10^6$/min, which is 1.33% volume concentration. A microscope image demonstrating the separation between 18.68 µm and 26.9 µm particles is shown in FIG. 24B. The high-speed image indicates the separated particle streams near the opposite channel walls at the outlet.

Cells are different from rigid particles in terms of the deformability and shape. Hur et al. have reported that the shape of particles does not have an obvious influence on the focusing position in inertial microfluidics, but the hydraulic diameter of particles is the key factor, while the deformability has an evident effect on the focusing position of particles/cells, which makes the focused band of particles/cells slightly shift away from the channel wall as compared to that of rigid beads of the same size. If the device is employed in cell separation, the variation of cell deformability may affect the separation efficiency. But as shown in Example 2 above, the trapezoidal spiral is capable of producing comparable separation between deformable leukocytes and red blood cells, perhaps aided by the large distance between the inner focusing and outer trapping positions.

Force Balance Analysis and Focusing Mechanism in Rectangular Cross-Section Channel For the analysis of the forces exerted on a particle in curved microchannel, a coordinate system (x, y, z) is defined as shown in FIGS. 20 and 21. The direction along the channel curve (main flow direction) is along the x axis. The direction along the channel depth is the y axis, and the radial direction along the channel (the width direction), is the z axis.

Along the cross-section, the Dean induced drag force $F_{DD}$ and the inertial lift force $F_L$ are dominant among all of the forces exerted on the particles suspended in a spiral channel (details of force analysis can be found below). The equilibrium position of particles is thus dependent on the balance between these two forces.

For a particle balanced at a certain position of the channel cross-section, the difference in particle velocity along the y-z plane and the Dean flow velocity in its proximity could generate a drag force on the particle that follows Stokes' law (i.e., drag force being proportional to Dean velocity) as illustrated in FIGS. 20 and 21. This drag force $F_{DD}$ is entirely dependent on the Dean flow field. It is evident that the Dean flow pattern does not change significantly for flow rates increasing from 1.0 mL/min to 8.0 mL/min in the simulation model. At the mid-section of the channel cross-section along channel width (z-axis), the Dean flow velocity is always parallel to the z-axis and changes its direction along the channel depth as one moves closer to the top and bottom walls (y-axis). Thus, except for the inner/outer wall region, $F_{DD}$ is primarily acting parallel to the z-axis. In the region between 28±0.5% and 72±0.5% of the channel depth, $F_{DD}$ points to the negative direction of the z-axis, while at regions near the top/bottom wall, it follows along the positive direction of the z-axis.

Small particles in a shear field experience a lift force $F_L$ that is perpendicular to the direction of the flow as a result of the inertial effects in the viscous flow around the particles. For the above designs of microfluidic channel, $F_L$ is dominant in most locations compared to $F_{DD}$, except near the 'minimal lift force' regions. Although so far there has been no simulation result for the distribution of $F_L$ in low aspect ratio rectangular channel, at the center region of the channel cross-section, $F_L$ always points toward the channel top or bottom wall.

Near the channel wall, the lift force balance in a straight channel has been numerically simulated and experimentally observed in previous studies. The direct observation of focusing position in the cross-section of square channel by Choi indicated that particles will balance close to the four channel walls, which are named the "minimum lift force planes". Bhagat et al., observed the distribution of fluorescent particles from both top and side views and showed that for a rectangular straight channel, the four minimum lift force planes reduce into two minimum lift force planes along the longer side walls. Other results agree with their observation in the curved channel, in the sense that particles focused at the 22% and 78% of the channel depth along the top and bottom channel walls in the rectangular cross-section curved channel. Furthermore, according to their experimental data, particles remain dispersed along the minimum lift force planes at low flow rates, and will focus to the centers of the minimum lift force planes as the flow rate increases. This experimental behavior in a straight rectangular channel, coupled with numerical calculation, reveals that $F_L$ within the minimum lift force plane is still pushing particles toward the true equilibrium (center of the planes). While this force is weak at low flow rates, it leads to particles being dispersed along the planes. With higher flow rates, $F_L$ increases more rapidly ($F_L \sim U_m^2$, where $U_m$ is the mean velocity of main flow) and becomes significant, leading to particles being focused at the center of the minimum lift force planes.

Figure 25:
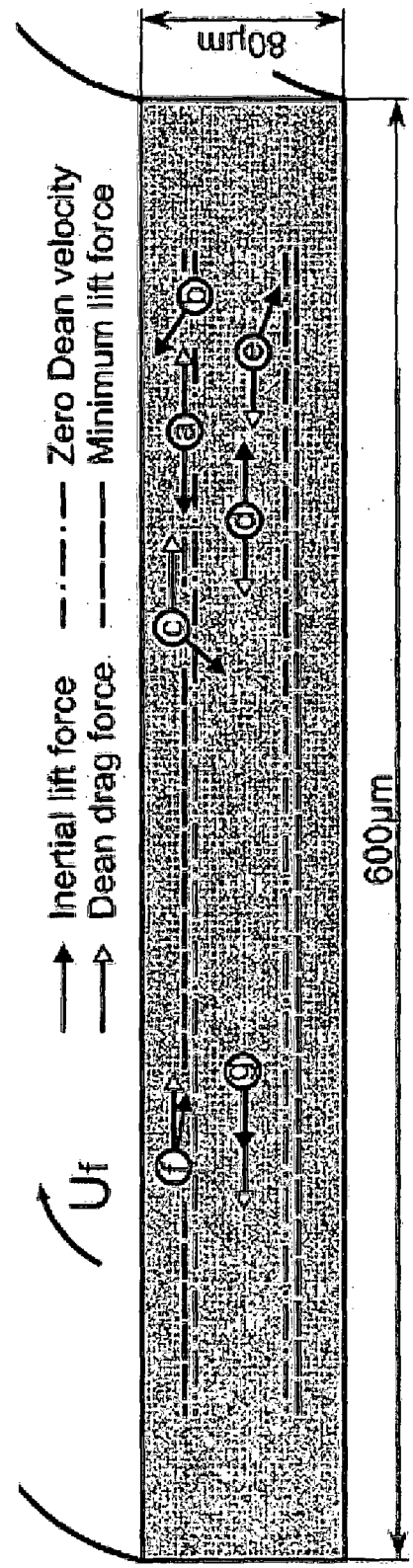
FIG. 25 is a schematic illustration of the forces acting on the particles at several typical positions in a trapezoidal cross-section microchannel. Forces acting on particles at positions a indicate the imbalance at inner side at high flow rate. Forces acting on particles at positions b, c, d and e illustrate that these particles tend to be trapped near the Dean vortices centered at different points. White cones indicate the direction and logarithmic magnitude of simulated Dean velocity as well as Dean drag.

The behavior of particle in a curved rectangular channel can similarly be explained. Because there is no $F_{DD}$ in the y direction except near the side wall regions, the focusing position of all the particles along the y axis is determined by $F_L$, which focuses particles at 22% and 78% of the channel depth as in the straight rectangular channel. At these minimum lift force planes (22% and 78%), the Dean flow pushes the particles toward the inner wall until the particles start to experience a weaker $F_{DD}$ (due to edge effect, around 10% of the width from the inner wall) and are balanced by weak $F_L$ within the minimum lift force planes. This (position a in FIG. 25) is a stable equilibrium, since any departure (in y axis) would create much stronger $F_L$, forcing the particle to return to the minimum lift force planes (positions b and c in FIG. 25). The focusing position here will depends on the size of the particle, mainly through the $F_{DD}$ term (~r), pushing larger particles further into the inner side wall compared with the smaller ones. In this regime (below about 3 mL/min in FIG. 23) a higher flow, rate will push the particle further toward the wall, due to increased $F_{DD}$ (~$U_m^2$).

When the flow rate increases (above about 3 mL/min in FIG. 23), $F_L$ (~$U_m^2$) along the z-axis increases faster than $F_{DD}$ (~$U_m^{1.63}$ or $U_m^{1.8}$), and the particle focusing position will start to move towards the outer wall. (FIG. 22). For different-sized-particles, the magnitude of $F_L$ ($F_L \sim r^3$) grows faster with the flow rate than $F_{DD}$ for larger particles. This is the mechanism behind the second transition of focusing position (above about 3 mL/min) from the inner to the outer side of the channel. In this regime, the larger particles will undergo this transition more abruptly (more rapid increase in $F_L$) than the smaller particles, as one can see in FIG. 22. The significant implication is that the physical separation between the larger and the smaller particle streams becomes smaller, simply because the larger particle stream comes to the outer side more abruptly and overlaps with the smaller particle stream. As a result, separation resolution of the spiral inertial sorter with rectangular cross-section can be optimized at a certain flow rate, and cannot be further improved solely by changing flow rates.

On the other hand, particles at the center line (particle d in FIG. 25) could also be balanced at the inner half of channel, where $F_L$ (inward) and $F_{DD}$ (outward) are in opposite direction. However, this equilibrium, if it does exist, is not a stable one, since a small offset from the center line will result in significant particle position deviation (Particle e in FIG. 25) toward the nearby minimum lift force plane. In the outer half of the channel, $F_L$ and $F_{DD}$ are generally in the same direction and therefore it is not possible to balance the forces (particles f and g).

Notably, the above analysis does not consider the interaction between the particles and the flow field. In fact, it has been proposed that the presence of the particles could change the distribution of main flow dramatically, and even induce lateral flow. The change of the main flow can directly affect $F_L$ and $F_{DD}$. Since the Dean flow is caused by the heterogeneity of the main flow, the distribution of Dean flow will also be modified by both the change of the main flow and the particle induced lateral flow, changing the magnitude of $F_{DD}$ in turn. Therefore, it would be difficult to give a quantitative analysis of these forces even when the simulation data of $F_L$ in a straight channel is available. However, based on this simplified force analysis, one can still get a qualitative understanding of the force balancing within spiral inertial microfluidic channels, where the lift force is primarily balanced by the drag force.

Focusing Mechanism in a Trapezoidal Channel

Figure 26:
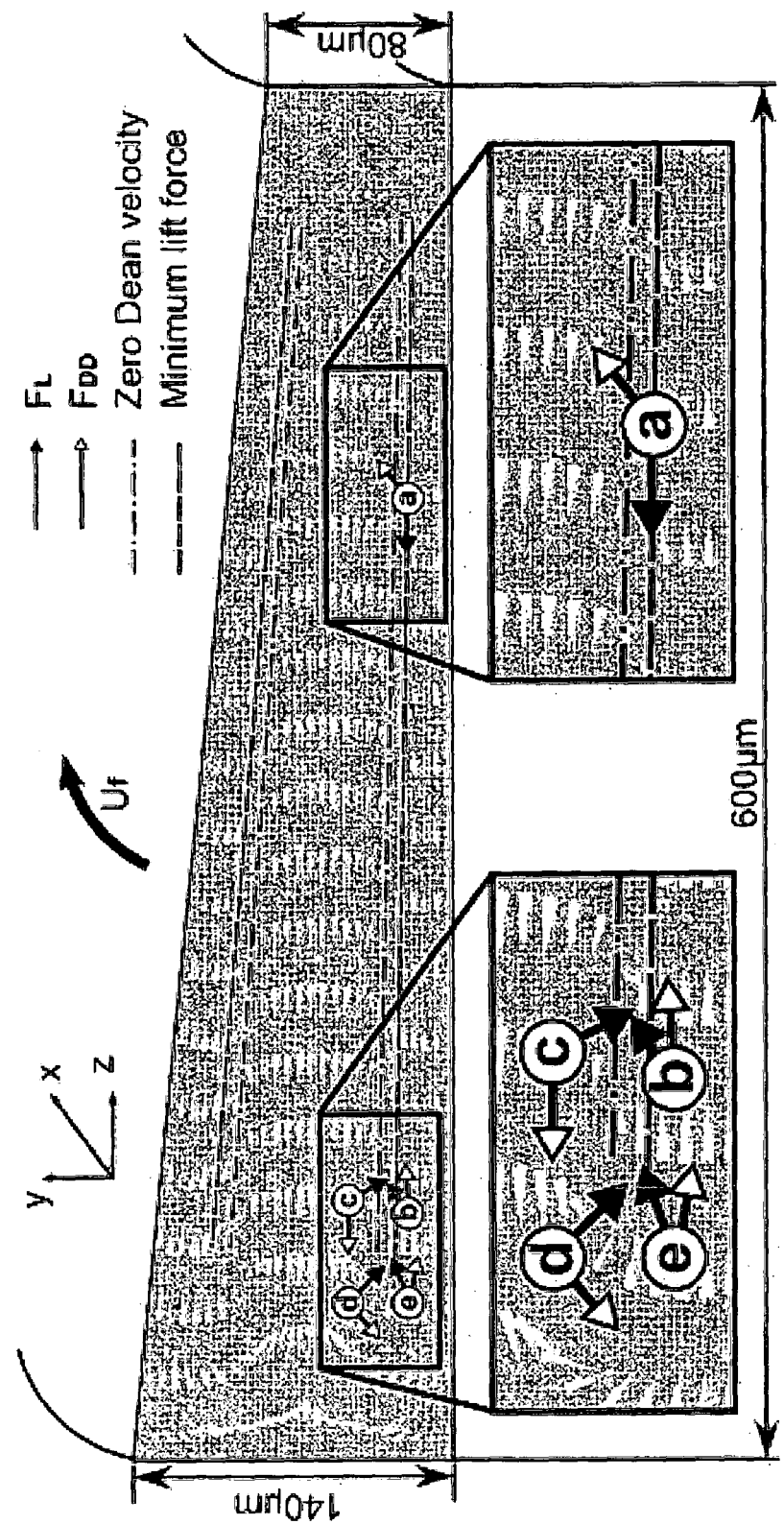
FIG. 26 is a schematic illustration of the forces acting on the particles at several typical positions in a trapezoidal cross-section microchannel. Forces acting on particles at positions a indicate the imbalance at inner side at high flow rate. Forces acting on particles at positions b, c, d and e illustrate that these particles tend to be trapped near the Dean vortices centered at different points. White cones indicate the direction and logarithmic magnitude of simulated Dean velocity as well as Dean drag.

In rectangular cross-section channels, particles focus at certain positions (typically at the inner side of the curved channel) as a result of the balance between $F_{DD}$ and $F_L$. If any force is changed, the balance is broken and the particles will shift to a new focusing position in the cross-section. The modification of the focusing position can be easily achieved by altering the geometry of the channel's cross-section. A trapezoidal channel with shallow inner and deep outer cross-section, for example, causes the main flow to shift towards the outer side of the channel cross-section. This generates a stronger Dean flow at the outer side and a weaker Dean flow at the inner side (FIG. 26). Significant differences exists between the Dean flow field at the inner half of the rectangular and trapezoidal cross-section channels, with the latter having a Dean flow velocity with a significant component along the y-axis (i.e., the minimum lift force plane and the Dean flow field are not parallel with each other, as in the case of rectangular channels). It means that if particles are placed at corresponding minimum lift force planes in the trapezoidal cross-section channel, the particles will be subject to a component of $F_{DD}$ pointing to the channel center along y-axis direction. Thus, particles will then balance further away (toward the center) from the minimum lift force planes in trapezoidal channels. This is supported by the experimental data showing that particles are focused at 25.5-27.1% of the local channel depth at flow rates ranging 0.5-3.0 mL/min, which is indeed very close to the "zero Dean flow plane" in the rectangular channel. Indeed there is no true 'zero Dean flow plane' in the trapezoidal channel, except the Dean vortex core on the outer side of the channel.

Within the inner half of trapezoidal cross-section, the distribution of the Dean flow is similar to that in a rectangular cross-sectional channel, despite the lower magnitude, since the center of the Dean vortices are far away from the inner wall. At low flow rates, where the lift force is not high enough to push particles away from the inner side, the large particles will remain focused near the inner channel wall, as in the case of rectangular channels. With increasing flow rates, particles begin to move towards the outer wall due to the increase in $F_L$ along z-axis. $F_{DD}$ has two components here, a component along y-axis pointing toward the center of channel cross-section near "zero Dean flow plane", termed as $F_{Dy}$ and the corresponding component along z-axis, termed as $F_{Dz}$. From FIG. 26 it can be seen that even at "zero Dean flow plane", $F_{Dy}$ remains non-zero and its magnitude is increasing from the inner side to the outer. This generally renders the balancing between $F_{DD}$ and $F_L$ more unstable, especially at higher flow rate. More specifically, as the particle in position a shows, the higher flow rate tends to push the focusing position toward the center of the channel, to where the Dean flow is stronger and therefore could strip the particles away from being trapped by the lift force.

Once the particle moves to the outer half of the channel near one of the vortex centers, the resultant force of $F_{DD}$ and $F_L$ will push the particle to an equilibrium position close to the center of the vortices. The forces acting on the particle near vortex center are illustrated in FIG. 26. The trapping is caused by a dynamic balance of these two forces, which rely on many parameters, such as the slant of channel, the flow rate, and the diameter of particle. For example, under the resultant force of $F_{DD}$ and $F_L$, a particle at position b will tend to cross the minimum lift plane and migrate towards position c, where a strong $F_{DD}$ can then push the particle towards position d. Qualitatively, near the Dean core, particles on the minimum lift force plane (positions b, e) experience $F_{DD}$ that pushes them towards the Dean core, while the particles trapped near the Dean core (or zero $F_{Dz}$ line, positions c, d) experience both $F_{DD}$ and $F_L$ that drive the particle back to minimum lift force planes.

A trapezoidal cross-section with a deeper inner wall compared to the outer wall will have strong vortices formed at the inner side, resulting in all the particles being trapped despite varying particle size and flow rate. Such geometry is not applicable for size based separation. Microchannels were also fabricated with the top wall having a concave, convex or just a regular slanted top wall and their effect on particle focusing and trapping was studied. The experimental comparison of these three patterns is discussed below.

For a trapezoidal cross-section spiral microchannel, there are several factors that affect the focusing position and separation efficiency, such as the width, inner and outer depth of channel cross-section, the radius of the spiral curvature, and the slant angle. As analyzed above, the slant of the channel affects the focusing.behavior in two ways: (i) the threshold flow rate required to trap particles in the Dean vortex as a function of particle size and (ii) the location of the Dean vortex core. A large slant angle will lead to strong Dean at the outer side and increase trapping capability of particle. Large slant angle can also decrease the threshold flow rate required to trap the particles of a certain size within the Dean vortex. This understanding was further validated by the observation of particle bands in channels with different slant angles and three different channel cross-section geometries (data and discussion included below).

Experimental results confirming the three dimensional particle focusing in spiral microchannels are presented herein. The results indicate that particles form two bands along the depth symmetrically between the zero-lift force plane and the centers of the Dean vortex in spiral channels. Based on the experimental evidence and the numerical simulation of the Dean flow profile, a detailed explanation of the focusing mechanism is presented, taking into account of various forces acting on the particle. With this understanding of the particle focusing mechanism, a trapezoidal cross-section spiral microchannel for particle separation was developed and analyzed. A multi-loop microchannel was employed to calibrate the focusing of different size standard micro particles of 5.78 µm, 9.77 µm, 15.5 µm, and 26.25 µm diameter for flow rates ranging from 0.5-7.5 mL/min. The experimental results indicate that particles occupy an equilibrium position near the inner microchannel wall when particles are introduced under a lower flow rate. However, beyond a threshold flow rate (which is size-dependent) the equilibrium position is moved to the outer microchannel wall, suggested to be a Dean vortex trap. Taking advantage of this sudden transition, the trapezoidal cross-section spiral microchannel is capable of producing higher resolution separation of particles than conventional rectangular cross-section spiral. Separation of 15.5 µm and 18.68 µm beads at an ultra-high throughput of about $1.61 \times 10^7$/min with over 92% efficiency was achieved with this device.

Methods

Device Design and Fabrication

Pressure-driven flows through a rectangular channel have a hyperbolic profile with the maximum velocity at the centroid of the cross section of the channel and zero velocity at wall surfaces. Particles suspended in such non-uniform flow fields experience appreciable inertial lift force resulting in their focusing at specific positions within the microchannel cross section. In a curved channel, the fluid experiences centrifugal acceleration directed radially outward giving rise to transverse flows characterized by two counter-rotating vortices, known as Dean vortices, at the top and bottom halves of the channel (see FIG. 27A).

Although inertial focusing within straight channels has been reported to require only 4 cm, the Dean vortices generated in curvilinear microchannel apply additional force on the particles, requiring longer channel length for the suspended particles to migrate to their balancing position. Considering this, all the microfluidic channels used in these experiments were designed to be 8-loops single-inlet two-outlet spiral with radius increasing from 8 mm 24 mm to provide sufficient length for the particle migration. Since the dimensions of the channel are in sub-millimeter range, the master mold with the specific channel cross-sections for subsequent polydimethylsiloxane (PDMS) casting was milled in polymethyl methacrylate (PMMA). Due to the limitation of the milling tool, the tolerance of the pattern is controlled to within 10 µm in the x-y direction and 2 µm in the z-direction with a surface roughness of Ra of about 0.8 µm. The mold was carefully inspected and its dimensions were measured accurately before use. The microchannels were then made by casting Sylgard 184 silicone elastomer (PDMS) prepolymer mixed in a 10:1 ratio with the curing agent. After curing, the PDMS was peeled from the mold and plasma bonded to another 3 mm thick flat PDMS layer. Input and output ports were punched prior to bonding.

Figures 27A, 27B:
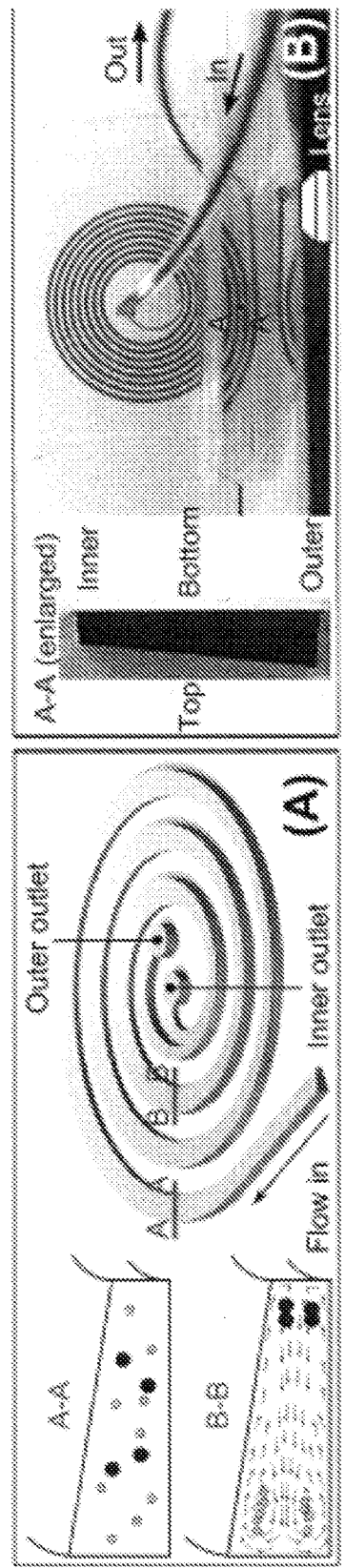
FIG. 27A is a schematic illustration of a trapezoidal cross-section spiral microchannel illustrating the principle of particle focusing and trapping within the Dean vortices.
FIG. 27B is an illustration of an actual spiral microfluidic device for side view focusing position measurement. The microfluidic channel is filled with dye for visualization. Samples are flowed from center loops to outer loops for the measurement.

For the measurement of the vertical focusing positions, the device was cut along the periphery of the spiral channel with about a 2 mm gap between the channel and the edge of the PDMS part. The PDMS mold with the microchannel pattern was then placed vertically in a flat-bottomed petri-dish and a second cast of PDMS was poured to hold the chip vertically (FIG. 27B). Tygon tubing was connected to the ports before the second cast to prevent PDMS from flowing into the channel. During the experiment, the device is placed on an inverted microscope and the image of the straight section is captured using fluorescent particles. Since PDMS is an elastic material the cross-section of the channel would undergo pressure induced deformation due to high driving pressure. High speed images are taken near the outer reservoir where the pressure of channel is close to atmospheric pressure to minimize the influence of channel expansion. The device shown in FIG. 27B is also used for size based particle separation. For separation experiments, the second cast was not required.

Fluid Preparation

For the observation of particle focusing from the side view, a spiral channel with a low aspect ratio rectangular cross-section was fabricated. The microchannel was 600 µm wide and 80 µm deep, with the aspect ratio of 7.5 (width/depth). If the refractive index difference between the fluid and PDMS channel is large, the imaging of fluorescent particles within the channel through a thick piece of PDMS is challenging due to significant refraction at the interface. To overcome this, dimethyl sulfoxide (DMSO) was mixed with ethanol in a 1:1 volume ratio, which produces a mixture with refractive index of 1.42, density of 0.9805 g/ml and viscosity of 0.978 mPa·s at 298.15K. The refractive index of the mixture is similar to that of PDMS (1.43) and enhances imaging by elimination of refraction based dispersion. The solution was shown to dissolve the polystyrene (PS) particles (Bangs Laboratories, Inc. USA) and Tygon tubing after prolonged immersion of 1 week. However, for the short duration of the experiments, the fluid mixture had no effect on both the particles and the tubings, making it an ideal replacement to water for the experiments.

Numerical Simulation

The Dean flow field of the fluid in curved channel was simulated using commercial computational fluid dynamics (CFD) software COMSOL 4.2a (Burlington, Mass.). Curved micro-channel sections with different cross sectional geometries were modeled as a 120° arc with a radius of 7.5 mm. The parameters of the density and the dynamic viscosity of the fluid in the channel section were set to that of water. The equations of laminar flow used in this simulation are given by $\rho(u \cdot \nabla)u = \nabla \cdot [-pI + \mu(\nabla u + (\nabla u)^T)] + F$ and $\rho \nabla \cdot u = 0$, where the symbols follow the default definition in COMSOL. The physical model was set to be incompressible and non-turbulent. The inlet boundary condition was set with the specified flow rate while the outlet was set to zero pressure with no viscous stress condition. At the channel walls, no slip boundary condition was applied. Typical flow rates from 1.0 mL/min to 8.0 mL/min were simulated to get the full solution for fluid flow at the steady state. Components of the flow velocity within the cross-section, i.e., the secondary Dean flows, were extracted at the center of the arc.

Discussion

Force Balance Analysis of Particle in Curved Channel

A particle flowing with surrounding fluid is subject to the following known forces: the drag force $F_D$, the centrifugal force $F_C$, the buoyancy force, i.e., the pressure gradient force $F_B$, two unsteady forces due to a change of the relative velocity, the added mass force or virtual mass force $F_A$, and the Basset History force $F_H$, the gravitational force $F_G$, and the inertial lift force $F_L$. Each of these forces will be discussed as applied on the suspended particles in the inertial flow regime.

Figure 28A:
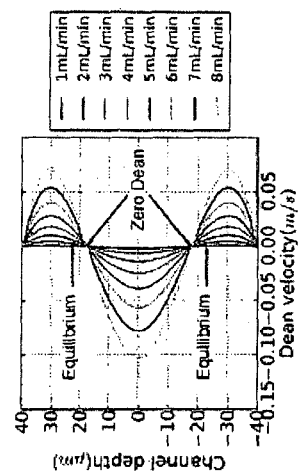
FIG. 28A is a schematic illustration of the relative flow velocity around a particle from top view of a curved channel.

(i) Drag force $F_D$—The drag force on the particle is in the direction of relative flow velocity $U_r$ with respect to the particle. The magnitude of $F_D$ can be given as $$F_D = \frac{1}{2}\pi \rho_f r^2 C_D U_r^2$$

where $C_D$ is the drag coefficient, $\rho_f$ is the density of fluid, and r is the radius of particle. In a curved channel with secondary flow, $U_r$ is a combination of two perpendicular relative flow velocities: the slip velocity $U_s$ along the main flow, which is refer to the velocity difference between particle and fluid along x direction, and the Dean velocity $U_D$ for a particle focused at a balanced point in the channel's cross-section. Thus we have $U_r = U_s + U_D$ as shown in FIG. 28A.

According to Yang's simulation, in a tube Poiseuille flow with a freely rotating particle of a radius r=0.075 D at equilibrium position under moderate Reynolds number $$Re = \frac{8\rho_f r^2 U_m}{\mu D},$$

where $U_m$ is the mean velocity of the main flow in the channel, D is the hydraulic diameter of the tube (equivalent to the depth of the channel here), and µ is the dynamic viscosity of the fluid, the flow velocity of particle $U_p$ is smaller than that of the surrounding fluid $U_f$. The slip velocity is given by $$U_s = U_f - U_p = \frac{0.0412 Re^{1.04} \mu}{2 r \rho_f} \approx 0.05 U_m.$$

Figure 28B:
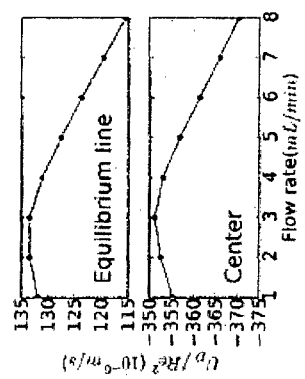
FIG. 28B are graphs of the Dean velocity as a function of flow rate (mL/min) showing that the Dean velocity $U_D$ increases with Re according to simulation in a rectangular channel. The value of $U_D$ in the top curve is the magnitude of Dean velocity at 22% of channel depth (focusing position), while $U_D$ in the bottom curve is the value of Dean velocity at the center of the channel.
Figure 28C:
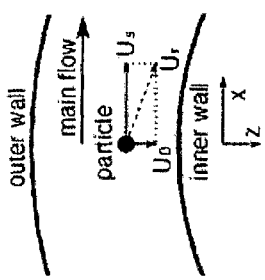
FIG. 28C is a graph of the channel depth (µm) as a function of the Dean velocity (m/s) showing the magnitude of the Dean velocity along the y-axis at different flow rates at the center line of channel width.

For a given point, $U_D$, according to the simulation result for an 80 μm deep 600 μm wide rectangular cross-section channel, is generally proportional to $Re^2$, i.e. the magnitude of $U_m^2$, which is different from Ookawara's result of $U_D \sim U_m^{1.63}$. The disagreement might be due to the difference of structural parameters between the two models. From FIGS. 28B and 28C, it can be seen that the Dean flow velocity increases slightly faster than $\sim U_m^2$ when the flow rate is less than 3 mL/min, both at the center and at 22% of channel (near the minimum lift force plane (see FIG. 25), where particles are focused). On the other hand, $U_D$ increases more slowly than $U_m^2$ (approximately $\sim U_m^{1.8}$) at flow rate >4.0 mL/min. The maximum magnitude of $U_D$ achieved in the system is 0.037 $U_m$, which is at the flow rate of 8.0 mL/min ($U_m$=2.778 m/s).

In this system, for flow rates from 1.0 to 8.0 mL/min, one has the Reynolds number of the particle $$0.26 < Re_p = \frac{2\rho_f r U_r}{\mu} < 2.59$$

calculated based on the above analysis of $U_r$. Based on Morsi's analysis/model, the $C_D$ for $0.1<Re_p<1.0$ and $1.0<Re_p<10.0$, could be estimated by equation $$C_D = \frac{22.73}{Re_p} + \frac{0.0903}{Re_p^2} + 3.69 \text{ and } C_D = \frac{29.1667}{Re_p} - \frac{3.8889}{Re_p^2} + 1.22,$$

respectively. Here, to simplify the analysis, the first-order approximation is taken, $$C_D = \frac{24}{Re_p},$$

which will make the calculated $F_D$ slightly smaller than the actual value. The drag force then follows Stokes Law as $$F_D = \frac{1}{2}\pi\rho_f r^2 \frac{24}{Re_p} U_r^2 = 6\pi\mu r U_r.$$

The component of $F_D$ induced by the Dean flow in the channel's cross-section is thus given by $$F_{DD} = 6\pi\mu r U_D$$

Although there is shear in the Dean flow and the particle will rotate according to both the shear of the main flow and the Dean flow in the channel, Kurose demonstrated that the shear rate and rotation velocity caused by the Dean flow do not have significant effect on the direction and magnitude of the drag force at $Re_p$ in above range. The Dean induced drag $F_{DD}$ is thus always along the Dean direction and is proportional to the local Dean velocity $U_D$.

(ii) Lift force $F_L$—Since $U_D$ is two orders of magnitude smaller than $U_m$ in the curved channel, here one only considers the lift force induced by the main flow. The lift force comes from two separate effects: the slip-shear of the fluid surrounding the particle, which is first identified by Saffman, and the slip rotation of the particle in fluid, known as the Magnus effect. The distribution of $F_L$ in a square cross-section straight channel was studied by others, however no mathematical calculations were given. Here, to show the relationship between $F_L$ and the flow velocity as well as the particle diameter, the lift force equation of a freely rotating particle in steady flow within a cylindrical tube by Yang is used. In a tube Poiseuille flow with a freely rotating particle of radius r=0.075 D near the equilibrium position, $$F_L = 1.085 Re^{1.064} \mu r U_s \left(\frac{\omega_d}{\omega_e} - 1\right) \approx \frac{8.68\rho_f r^3 U_m U_s}{D}\left(\frac{\omega_d}{\omega_e} - 1\right)$$

where D is the (hydraulic) diameter of tube, $\omega_d$ and $\omega_e$ are the slip angular velocities of the particle at a position with relative distance d from the center of the tube's cross-section and equilibrium position respectively. The term $\omega_d/\omega_e$ is a function of particle position d and Reynolds number Re $$\frac{\omega_d}{\omega_e} = 0.00913 e^{9.2d} Re^{1.08-2.1d}$$

$F_L$ is zero at the equilibrium position, which is around 20% of D from the wall, and changes its direction when the particle moves across the equilibrium position. The magnitude of $F_L$ near the equilibrium position, according to above equations, is approximately proportional to $U_m U_s \sim 0.05 U_m^2$.

(iii) Centrifugal force $F_C$—For a particle flowing in a curved channel with the radius of curvature R, the centrifugal force subjected to the particle is pointing towards the outer side of the channel along the z direction and is proportional to $U_p^2$):

$$F_C = -\frac{m_p U_p^2}{R},$$

where $$m_p = \rho_p V_p = \frac{4}{3}\rho_p \pi r^3$$

is the mass of the particle. $\rho_p$ and $V_p$ represent the density and volume of the particle, respectively.

(iv) Buoyancy force $F_B$—In a fluid with constant pressure gradient, particles are subjected to a buoyancy force pointing to the center of the channel curvature, i.e., along the z-axis direction, $$F_B = \rho_f a_f V_p,$$

where $$a_f = \frac{U_f^2}{R}$$

is the centripetal acceleration of fluid around the particle. The force is opposite to $F_C$ and proportional to $U_f^2$.

(v) Added mass force $F_A$—If $U_f \neq U_p$, the centripetal acceleration or deceleration of particles must displace some volume of surrounding fluid as it moves through it, since the object and fluid cannot occupy the same physical space simultaneously. The particle can thus be considered to have an added mass. This added mass subjects the particles to an additional force since the particle and surrounding fluid are under different centrifugal velocity. This force points towards the outer side of the channel i.e., opposite to the z-axis, given by $$F_A = -m_A(a_f - a_p) = \frac{1}{2}\rho_f V_p \frac{U_p^2 - U_f^2}{R}.$$

(vi) Basset history force $F_H$—The Basset force describes the force due to the lagging boundary layer development with changing relative velocity (acceleration) of bodies moving through a fluid. It is difficult to calculate accurately and is commonly neglected for practical reasons.

(vii) Gravitational force $F_G$—Gravity is at least one order smaller than centrifugal force in this case. It can be neglected here.

The resultant force acting on the particle in the yz plane (cross-section of the channel), neglecting the smaller terms ($F_G$, $F_H$), $$m_p \frac{dU_p}{dt} = F_{DD} + F_L + F_C + F_B + F_A$$

If one assumes $\rho_p = \rho_f = \rho$, then one has $$F_{ABC} = F_C + F_B + F_A = \frac{2\pi\rho r^3(U_f^2 - U_p^2)}{3R} \approx \frac{4\pi\rho r^3 U_f U_s}{3R}$$

Figure 29:
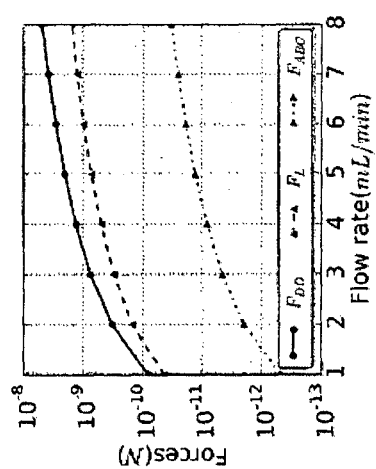
FIG. 29 is a graph of forces (N) as a function of flow rate (mL/min) showing the magnitude of 3 major forces on a 15.5 µm particle. $F_{DD}$ and $F_{ABC}$ are calculated based on the simulation of a rectangular cross-section channel; the particle is placed at the equilibrium position (22% of channel depth). $F_L$ is calculated following Yang's simulation, and the direction is along the axial direction of a cylindrical tube.

The resultant force $F_{ABC}$ is pointing to the center of the channel curvature, and the magnitude is proportional to $U_f U_s$, i.e. proportional to $U_m^2$. It is one or two order smaller than $F_{DD}$, as shown in FIG. 29. The effect of $F_{ABC}$ on the focus position is thus not dominant.

The Effect of Geometry of Channel Cross-Section

Figure 30:
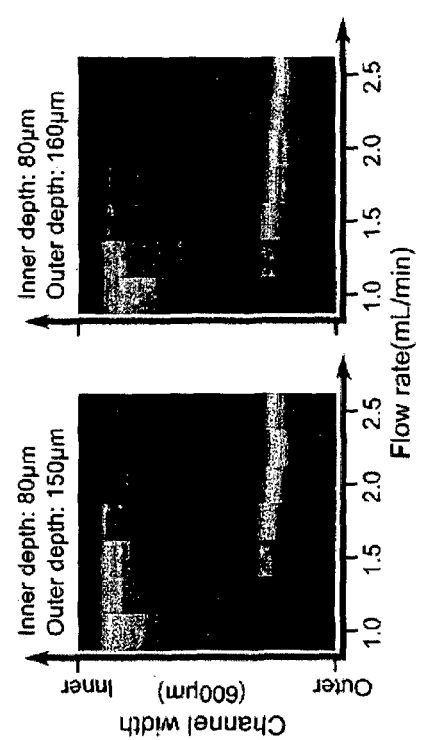
FIG. 30 is an illustration of the effect of slant angle on particle focusing in trapezoidal cross-section spiral microfluidic channel. The white band in the image indicates the focus band of 15.5 µm fluorescent beads from the top view.

For a trapezoidal channel with a higher outer wall, there are many factors affecting the focusing position and separation efficiency, such as the width, inner and outer depth of the channel cross-section, the radius of the spiral curvature, and the slant angle. As analyzed above, the slant of the channel affects the focusing behavior in two ways: (i) at lower inner side, the increase of channel depth breaks the balance of the lift and drag force at high flow rate resulting in particle migration to the outer side and trapped at the vortex core, i.e., determines the threshold flow rate; and (ii) the location of the Dean vortex core. A large slant angle will lead to strong Dean at the outer side and increase trapping capability of particle. A large slant angle can also decrease the flow rate to drag out particles from the inner side. Particles will switch to the outer side at lower flow rate for a large slant angle channel, which is confirmed by experimental observation shown in FIG. 30 as well as the observation shown in FIG. 22.

As another validation of this understanding, three different channel cross-section geometries were fabricated and tested (see FIGS. 31A-31C): normal trapezoidal cross-section with constant slant angle, top wall convex cross-section that have a large slant angle at the inner side but a small slant angle at the outer side, and a concave cross-section with only the outer half having a large slant angle. For a convex slant channel (shown in FIG. 31A), the increase of depth mostly occurred at the inner side. Focused particle streams moved to the outer side gradually with the increase of flow rate. Only a small shift occurred at 2 mL/min, and stopped at the middle of channel, where the slant angle decreased. In general, the performance of convex slant channel was closer to that of a rectangular cross-section channel, and shares the same drawback of narrow physical separation between streams of different particle sizes when utilized for separation.

For a concave slant channel (shown in FIG. 31C), the increase of channel depth mostly occurred at the outer side. Therefore, it generated strong Dean vortices even at lower flow rate. These strong Dean vortices were able to trap particles at a much lower flow rate, compared with the normal slant channel (shown in FIG. 31B). On the other hand, since the slant angle was small, particles continued to remain focused at the inner side, generating two semi-stable focusing positions around 1 mL/min flow rate. In this situation, particles were separated into two bands at both sides of channel, which is also not desirable for particle separation. Beside convex and concave trapezoidal channels, spiral channels with varying top wall geometries were also tested—stepped profile, as shown in FIG. 2c, and a square wave profile, as shown in FIG. 2d.

Example 4

Slanted Spiral Microfluidics for the Ultra-Fast, Label-Free Isolation of Circulating Tumor Cells The enumeration and characterization of circulating tumor cells (CTCs), found in the peripheral blood of cancer patients, provide a potentially accessible source for cancer diagnosis and prognosis. A spiral microfluidic device with trapezoidal cross-section is described herein for ultra-fast, label-free enrichment of CTCs from clinically relevant blood volumes. The technique utilizes the inherent Dean vortex flows present in curvilinear microchannels under continuous flow, along with inertial lift forces which focus larger CTCs against the inner wall. Using a trapezoidal cross-section as opposed to a traditional rectangular cross-section, the position of the Dean vortex core can be altered to achieve separation. Smaller hematologic components are trapped in the Dean vortices skewed towards the outer channel walls and eventually removed at the outer outlet, while the larger CTCs equilibrate near the inner channel wall and are collected from the inner outlet. Using a single spiral microchannel with one inlet and two outlets, more than 80% of cancer cell line cells (MCF-7, T24 and MDA-MB-231) spiked in 7.5 mL of blood were successfully isolated and recovered within 8 min with extremely high purity (400-680 WBCs/mL; about 4 log depletion of WBCs). Putative CTCs were detected and isolated from 100% patient samples (n=10) with advanced stage metastatic breast and lung cancer using standard biomarkers (CK, CD45 and DAPI) with frequency ranging from 3-125 CTCs/mL. This approach can surmount the shortcomings of traditional affinity-based CTC isolation techniques as well as enable fundamental studies on CTCs to guide treatment and enhance patient care.

In contrast to rectangular cross-section channels that typically use a sheath flow originating from a separate inlet to pinch the sample at the inlet to confine the sample to a narrow region across the channel width, so that all the cells start to migrate from approximately the same location, and thereby improve particle dispersion inside the channels when the particle concentration is high, the trapezoidal channels only need a single inlet for the sample, in which the sample can be introduced, e.g., using a single syringe pump, and two outlets for waste and enriched cell collection, respectively, during operation. In some aspects, the sample can be introduced using a piston pump, a gear pump, a peristaltic pump, a piezoelectric micropump, or using a controllable pressure regulator. Using a microfluidic device with this newly designed microchannel, enrichment of a high number of CTCs (3-125 CTCs/mL) from peripheral blood of patients with metastatic breast and lung cancer has been demonstrated. This device can process 7.5 mL of red blood cell lysed blood in about 8 min, allowing enrichment of viable CTCs with relatively high purity and yield. The trapezoidal spiral channels can be produced at extremely low-cost and with high resolution using conventional micro-milling and PDMS casting, and can be operated using a single syringe pump, which facilitates easy automation. This strategy can be utilized for large-scale processing of clinical samples in order to enrich sufficient amount of CTCs for various detailed molecular analyses as well as clinical monitoring of individual patients undergoing therapy. The device is well suited to process even larger quantities of blood if required (20 mL in about 15 min), to satisfy a growing need for obtaining large number of CTCs for multiple downstream tests.

Material and Methods

Device Design and Fabrication

The device design consists of an 8-loop spiral microchannel with one inlet and two outlets with radius increasing from 8 mm to 24 mm for efficient cell migration and focusing. The width of the channel cross-section is 600 μm and the inner and outer heights were optimized at 80 μm and 130 μm, respectively, for the trapezoid cross-section. The mold with specific channel dimensions was designed using SolidWorks software and then fabricated by conventional micro-milling technique (Whits Technologies, Singapore) on polymethyl methacrylate (PMMA) sheet for subsequent PDMS casting. The microfluidic device was fabricated by casting degassed PDMS (mixed in a 10:1 ratio of base and curing agent, Sylgard 184, Dow Corning Inc.) on the mold and subsequent baking inside an oven for 2 hours at 70° C. After curing, the PDMS was peeled from the mold and access holes (1.5 mm) for fluidic inlet and outlets were punched with a Uni-Core™ Puncher (Sigma-Aldrich Co. LLC. SG) and the PDMS devices were irreversibly bonded to another layer of cured PDMS using an oxygen plasma machine (Harrick Plasma, USA) to complete the channels. The assembled device was finally placed inside an oven at 70° C. for 30 minutes to further enhance the bonding.

Cell Culture and Sample Preparation

Two commercially available green fluorescent protein (GFP)-tagged human cancer cell lines, namely breast adenocarcinoma (MCF-7 and MDA-MB-231), one bladder (T24; HTB-4 ATCC, USA) and one lung (H159; HTB-4 ATCC, USA) were used to mimic CTC separation. SKBR3 cell line was also employed as a control for DNA FISH analysis of HER2 in enriched CTCs. The aforementioned cells have an average diameter in a range of between about 10 μm and about 50 μm. The cells were seeded into coated T25 flasks (Becton, Dickinson and Company, Franklin Lakes, N.J., USA) and cultured with high-glucose Dulbecco's modified Eagle's medium (DMEM) (Invitrogen, USA) supplemented with 10% fetal bovine serum (FBS) (Invitrogen, USA) and 1% penicillin-streptomycin (Invitrogen, USA). The culture was kept in a humidified atmosphere at 37° C. containing 5% (v/v) $CO_2$ and harvested at 80% confluence for spiking. Sub-confluent monolayers were dissociated using 0.01% trypsin and 5.3 mM EDTA solution (Lonza, Switzerland). For all experiments unless otherwise mentioned, whole blood obtained from healthy donors and patient samples were lysed with RBC lysis buffer (G-Bioscience, USA) for 5 minutes at room temperature with continuous mixing. Lysis was stopped by dilution with PBS buffer and cell pellet was obtained under centrifugation at 1000 g for 5 min. The cell pellet was resuspended to desired concentrations with PBS.

Device Characterization

In all the experiments, the spiral biochip was initially mounted on an inverted phase contrast microscope (Olympus IX71) equipped with a high speed CCD camera (Phantom v9, Vision Research Inc., USA). The biochip was primed with a priming buffer (1× PBS, 2 mM EDTA supplemented with 0.5% BSA) using a syringe pump (PHD 2000, Harvard Apparatus, USA) for around 2 minutes at a flow rate of 2 mL/min. During testing, cancer cells and blood sample were filled in a 10 mL syringe and pumped through the device using a syringe pump connected to the microchannel through flexible Tygon® tubing. The flow rate was set to 1700 μL/min for all the experiments. High speed videos were captured at the channel outlet using the Phantom Camera Control software and then analyzed using ImageJ® software.

Immunofluorescence Staining

To calculate the separation efficiency and enrichment ratio between the sample and sorted CTCs, flow cytometry using a BD Accuri™ C6 Flow Cytometer was employed for both the inlet and the CTC outlet. Immunofluorescence staining based on common markers for cancer cells and white blood cells (WBCs) was used for differentiation and quantification. The enriched cells from the CTC outlet were stained for fluorescein isothiocyanate (FITC) conjugated pan-cytokeratin (CK) (1:100, MiltenyiBiotec Asia Pacific, Singapore) and allophycocyanin (APC) conjugated CD45 marker (1:100, MiltenyiBiotec Asia Pacific, Singapore) for 30 minutes to identify cancer cells and WBCs, respectively. For clinical samples, CTCs were identified by staining with FITC-conjugated pan-cytokeratin (CK) (1:100, MiltenyiBiotec Asia Pacific, Singapore). Cells staining positively for pan-CK and Hoechst (nuclei stain) and negatively for CD45 with characteristic morphology of cancer cells (i.e., high nucleus to cytoplasm ratio) are identified as CTCs. Cells staining positively for CD45 and Hoechst and negatively for pan-cytokeratin are identified as leukocytes.

Cell Viability Assay (Using PI Staining and Culturing)

MDA-MB-231 and MCF-7 GFP-tagged cells mixed with blood from healthy donors were processed through the spiral microfluidics, and cell viability was assessed via trypan blue (or Propidium iodide (PI)) exclusion assay and through long-term re-culturing. Isolated CTCs were seeded onto polylysine-coated 2D cell culture substrates and cultured overnight as described. Cells were then stained with propidium iodide (PI) stain in situ. Cells were imaged and enumerated for PI positive staining to determine the percentage of cell viability after lysis and processing. The cell viability numbers were compared with cells obtained after lysis without spiral biochip processing.

Clinical Samples

Human whole blood samples were obtained from healthy donors and metastatic lung and breast cancer patients. This study was approved by the institutional review board and local ethics committee according to a protocol permitted by the Institutional Review Board (IRB). A total of 10 blood samples from healthy donors were used as controls and 10 samples from lung and breast cancer patients were processed for CTC enumeration. Blood samples were collected in vacutainer tubes (Becton-Dickinson, Franklin Lakes, N.J., USA) containing EDTA anticoagulant and were processed within 2-4 h to prevent blood coagulation. For all the samples, 7.5 mL of whole blood was lysed initially using RBC lysis, buffer and re-suspended in PBS prior to processing on chip. As an alternative to lysing, the whole blood can also be diluted by a factor in a range of between 5 times and 10 times prior to processing on chip.

Fluorescence In Situ Hybridization

Fluorescence in situ hybridization (FISH) was performed on SKBR3 (amplified HER2 signals) and MDA-MB-231 (non-amplified HER2 signal) cells lines as well as isolated CTCs according to the manufacturer's protocol. Cells were spun onto slides using a Cytospin centrifuge (Thermo Scientific, USA) at 600 rpm for 6 minutes. Slides were fixed in 4% PFA at room temperature for 10 minutes and dehydrated via ethanol series (80%, 90%, and 100%). For FISH analysis, slides were treated with RNase (4 mg/mL) (Sigma, USA) for 40 minutes at 37° C., washed with 1× PBS/0.2% Tween 20 (Sigma, USA) thrice and denatured with 70% formamide/2×SCC (saline sodium citrate, Path Vysion, Abbott, USA) for 10 minutes at 80° C. They were then quench dehydrated again via ice-cold ethanol series. HER2/neu (Abbott Laboratories, Illinois, USA) probes were directly applied to slides maintained at 42° C. Hybridization was continued at 42° C. under dark and humid conditions overnight. Slides were washed with 50% formamide/2×SSC and 2×SSC at 45° C. under shaking, counterstained with 4',6-diamidino-2-phenylindole Immunofluorescence for Assay Characterization To characterize the phenotypic ratio of CTC cultures, cells were incubated with a variety of antibodies, including fluorescein isothiocyanate (FITC) conjugated pan-cytokeratin (CK) (1:100, Miltenyi Biotec Asia Pacific, Singapore), fluorescein isothiocyanate (FITC) conjugated CD44 (1:100, Miltenyi Biotec Asia Pacific, Singapore), allophycocyanin (APC) conjugated CD24 (1:100, Miltenyi Biotec Asia Pacific, Singapore), allophycocyanin (APC) conjugated CD45 marker (1:100, Miltenyi Biotec Asia Pacific, Singapore) and Hoechst (Invitrogen, USA). Staining could be done either by adding the staining reagents directly onto the assay or in cell suspension after trypsinization. Cells were incubated for 30 minutes on ice with permeabilization (0.1% Triton 100×, Thermo Scientific, USA) after fixation with 4% paraformaldehyde (PFA) (Sigma Aldrich, USA).

Results and Discussion

Design Principle

Figure 32A:
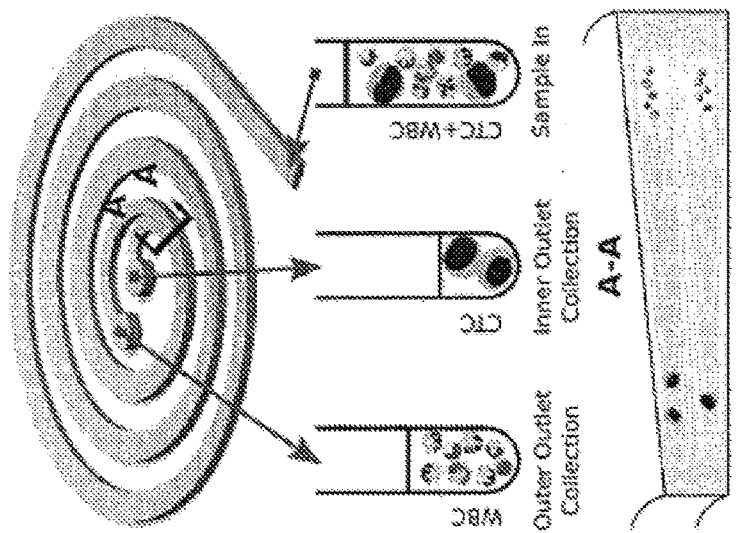
FIG. 32A is an illustration of the operating principle of CTC enrichment by a spiral channel with trapezoid cross-section (80/130 µm: inner/outer channel height). CTCs are focused near the inner wall due to the combination of inertial lift force and Dean drag force at the outlet while white blood cells (WBCs) and platelets are trapped inside the core of the Dean vortex formed closer to the outer wall.
Figure 32B:
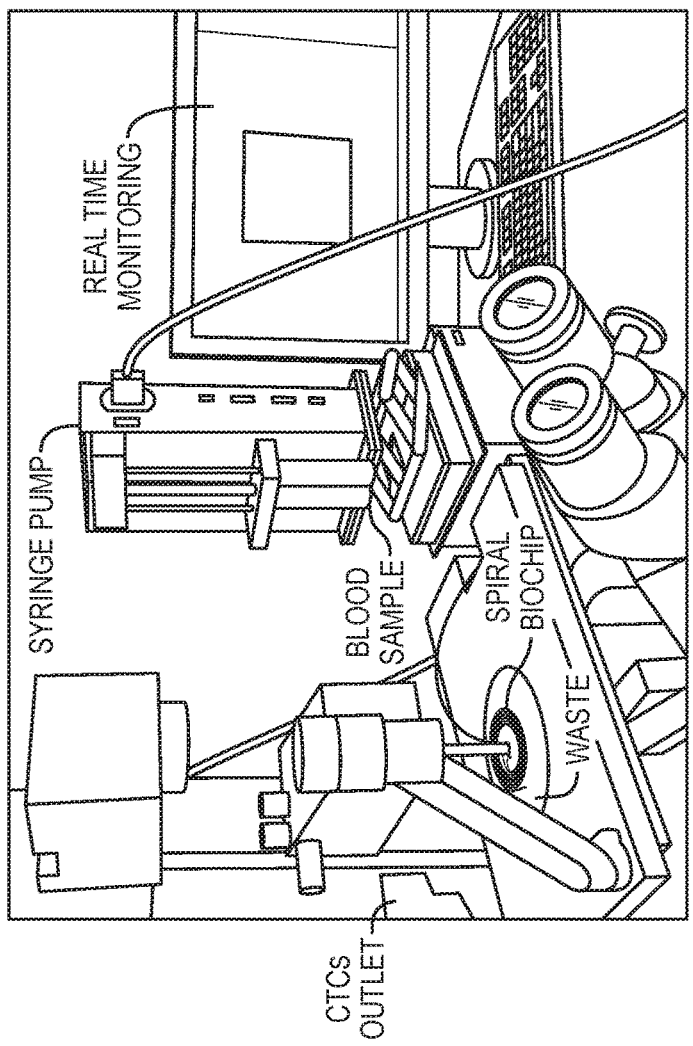
FIG. 32B is a line drawing of the workstation setup for CTC separation. The lysed blood is pumped through the spiral chip using a syringe pump where CTCs are separated from other blood components rapidly and efficiently.

When particles flow within a spiral microchannel, neutrally buoyant particles under the influence of inertial lift forces arising from the parabolic nature of the laminar velocity profile migrate across the streamlines to an equilibrium position away from the channel center towards the channel walls. At the same time, they also experience a drag force introduced by Dean vortices along the Dean flow arising due to the curvilinear geometry. The combination of inertial and Dean forces reduces the equilibrium positions to a single position at the inner microchannel wall within the channel width, inducing a continuous inertial focusing. Since both forces are a function of particle size, particles of different sizes occupy distinct lateral positions near the channel wall and exhibit different degrees of focusing, allowing size-based separation. One major challenge of utilizing a spiral microchannel with rectangular cross-section is that spacing between equilibrium positions of particles with varying diameters is narrow. This can affect the separation resolution. As discussed above, modifying the channel cross-section into a trapezoidal geometry can significantly enhance the separation resolution. This is mainly due to the fact that the asymmetry of trapezoid cross-section influences the velocity profile and results in the formation of strong Dean vortex cores near the outer wall that has the larger channel depth, as shown in FIG. 32A. Therefore, in contrast to the rectangular cross-section channels where small particle focus near the center of channel width under the balance of inertial and drag force, the modified velocity field of the trapezoidal spiral traps the smaller particles within the strong Dean vortex cores near the outer wall. With the large cells focused at the inner side, the spacing between the two cell streams is maximized and high throughput high-resolution sorting can be achieved. This unique design is ideally suited for enriching larger-diameter but lower-abundance target cells out of smaller but higher-abundance background cell mixtures, such as the isolation of leukocytes from raw blood, or enriching ultra-low abundance CTCs from blood as demonstrated herein. FIG. 32B shows a line drawing of the experimental setup during sample processing. The continuous collection of CTCs facilitates coupling of the device with conventional 96-well plate or a membrane filter for subsequent downstream analysis such as immunostaining, qRT-PCR, FISH and sequencing.

Characterization of Spiral Performance

Figure 33:
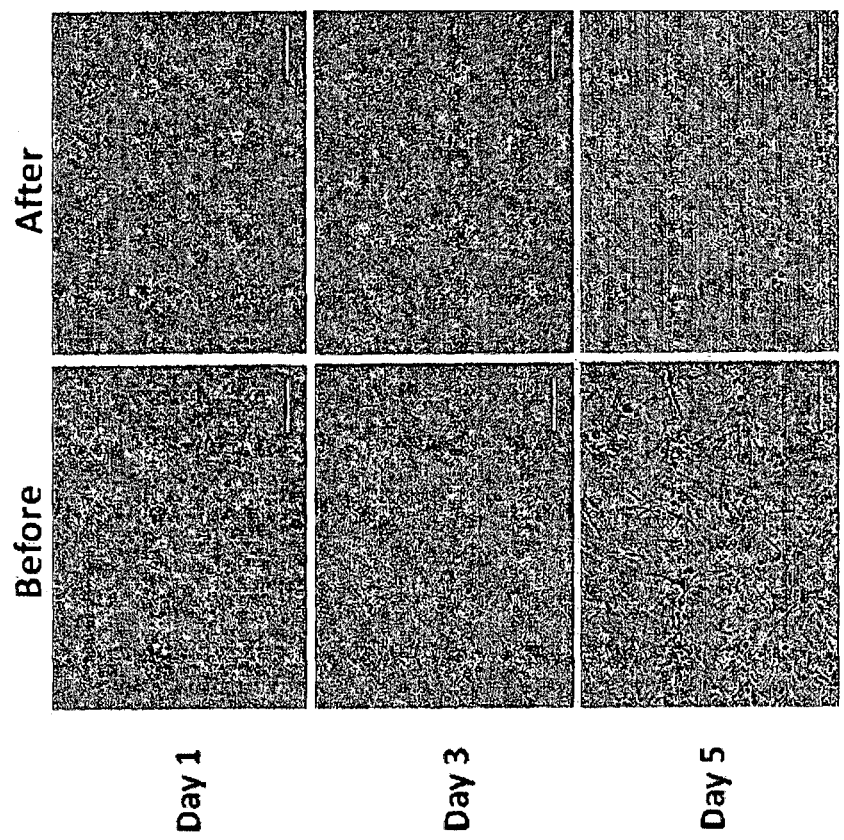
FIG. 33 are phase contrast micrographs of cultures of control (unsorted) MDA-MB-231 cells and cells enriched by spiral chip. The images indicate no significant differences between the morphology and proliferation rate of the cells suggesting high viability and sterility. Scale bar is 200 µm.
Figure 34A:
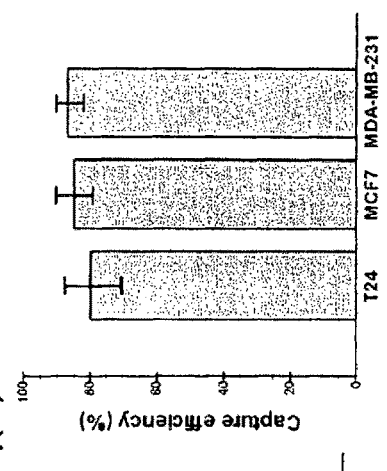
FIG. 34A is a graph of the number of WBCs/mL as a function of concentration factor showing the effect of WBC concentration on the performance of the trapezoidal spiral biochip and final purity.

An optimal technology for CTC isolation must aim to isolate the maximum number of viable cells with acceptable degree of purity (i.e., depending upon the contamination tolerance of downstream molecular assays) without relying on specific markers (e.g., EpCAM) with minimum sample processing steps. To increase the purity and minimize the cellular components passing through the spiral chip, a conventional chemical RBC lysis approach was utilized to boost the throughput of the system while maximizing the number of enriched CTCs. Although it has been reported that RBC lysis and density gradient centrifugation steps can lead to cell loss (10-30%), the experimental results showed that cell loss is less than 8% during the entire process. Furthermore, exposure to lysis buffer also did not alter the morphology and size of the cells, as shown in FIG. 33. Extensive characterization was performed to find the optimal device design by studying the effect of various parameters, including channel aspect ratio, flow rate and sample concentration using both latex particles and healthy blood samples spiked with cancer cell lines. As WBCs and platelets concentrations are relatively high (>3%) in the lysed blood, their complete removal is pivotal for achieving meaningful enrichment. To investigate the impact of input sample cell concentration on the output purity, processing of blood was carried out under different nucleated cell concentrations. Initial 7.5 mL whole blood samples collected from healthy donors were lysed chemically using ammonium chloride and the nucleated cell fraction was re-suspended back to 15 mL (0.5× concentration), 7.5 mL (1× concentration) and 5 mL (1.5× concentration) using PBS buffer for processing. The collected cells were stained using DAPI and CD45 antibodies to quantify the number of contaminated WBCs. FIG. 34A shows the total cells count (DAPI+/CD45+) collected from the CTC outlet at different sample concentrations. This graph shows that this device perform best when cell concentration is below 1× (about $3.5-4 \times 10^6$ WBC/mL) where minimum contamination of WBCs is observed (mean, 500 WBCs/mL of lysed blood; range, 400 to 680 WBCs/mL). Hence, 0.5× concentration was selected as being optimal for processing of clinical samples which translates to a total processing time of around 8 min for a 7.5 mL blood sample. It is believed that this is the highest throughput achieved by a microfluidic platform for CTC isolation reported to date. In addition, the processing time can be further decreased by multiplexing of biochips together.

Isolation Efficiency and Cell Viability using Cancer Cell Lines

Figure 34B:
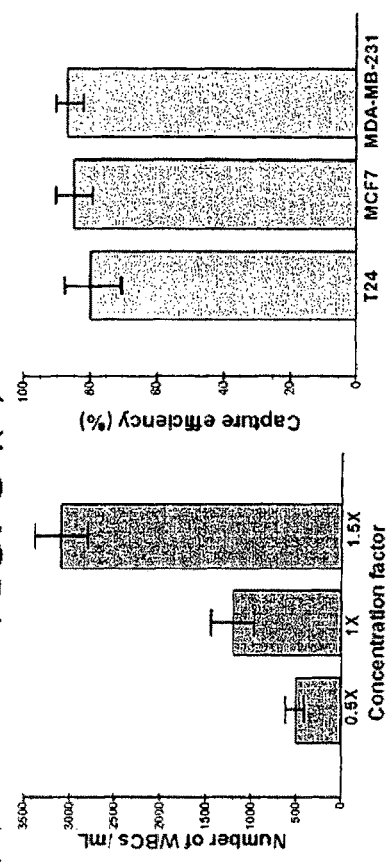
FIG. 34B is a histogram plot indicating a high separation efficiency of about 85% for different cancer cell lines tested.
Figure 34C:
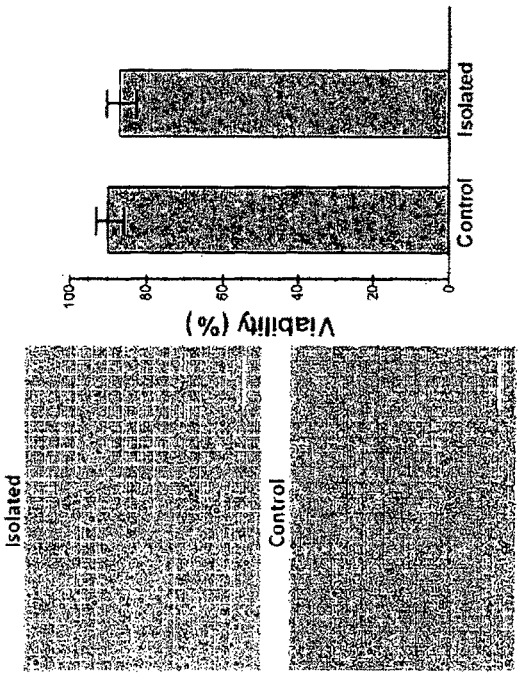
FIG. 34C are phase contrast micrographs of control (unsorted) and sorted MDA-MB-231 cells stained using trypan-blue dye indicating high cell viability, and bar graph results that confirm that the shear exerted on the cells during sample processing did not compromise their viability, retrieving >90% viable cells.
Figure 35:
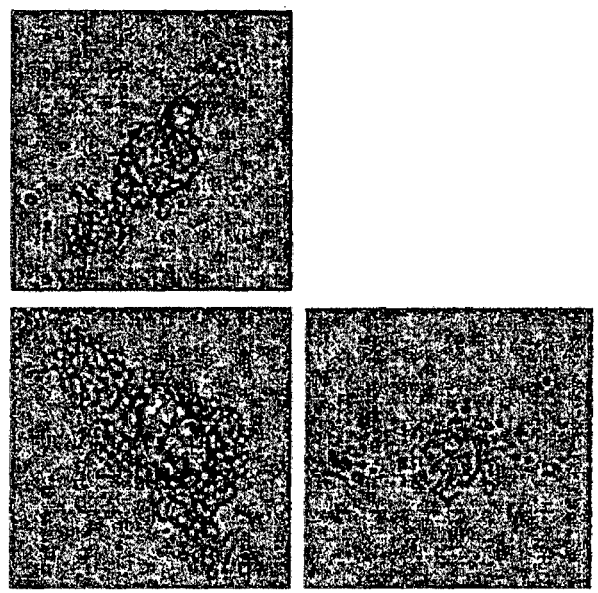
FIG. 35 are photographs illustrating the viability of captured CTCs by trapezoidal cross-section chip. Captured cells are plated onto 2D polylysine coated substrates and allowed to spread overnight. Clustering of platelets with CTCs can be observed in vitro. Viability of CTCs was confirmed using PI staining.

Since CTCs are extremely rare in blood stream, it is crucial to isolate the maximum number of target cells in a blood sample for various downstream assays. For this purpose, three different cell lines (i.e., MCF-7, T24 and MDA-MB-231) were employed in this study to quantify the performance of the trapezoidal spiral biochip for CTC isolation and recovery. These cell lines were chosen to ascertain the versatility of the technique in the detection of CTCs. The aforementioned cells have an average diameter in a range of between about 10 μm and about 50 μm. The model system is constructed by spiking a known number of cells (about 500 cells) into 7.5 mL of blood obtained from healthy donors. After RBC lysing and resuspension to the optimized concentration (about 0.5×), the sample was passed through the spiral chip for ultra-fast enrichment of spiked cells. Following enrichment, cancer cells were identified by immunofluorescence staining by either enumerating under epi-fluorescence microscope or flow cytometry analysis with common surface markers (CK+/CD45−). FIG. 34B shows a summary of capture efficiency of tumor cells spiked into whole blood with an average recovery of 80% for T24, 85% for MCF-7 and 87% for MDA-MB-231 cell lines (n=3). To validate the viability of the captured tumor cells using this device, the isolated cells were re-cultured onto 2-D culture substrates where they attached and proliferated under standard culture conditions (see FIG. 35). The viability of cells before and after processing was also validated using functional assays including staining with propidium iodide (PI) and/or Trypan blue. The results demonstrate high viability of captured cells confirmed by their minimal staining (<10%) with Trypan blue (see FIG. 34C). Further morphological analysis of cancer cells also confirmed that cells remain relatively unchanged during multiple steps of processing (data not shown).

Clinical Samples

To validate the clinical utility of the trapezoidal spiral biochip, a 7.5 mL of blood sample was obtained from each of (i) 5 healthy individuals (control), (ii) 5 patients with metastatic breast cancer (MBC) and (iii) 5 patients with non-small cell lung cancer (NSCLC) (Table 1).

TABLE 1

Clinico-pathological characteristics of patients enrolled in this study for quantification of CTC counts.

| Sample no | Subject initial | CTCs/mL |
|---|---|---|
| 1 | Healthy | 1 |
| 2 | Healthy | 2 |
| 3 | Healthy | 3 |
| 4 | Healthy | 2 |
| 5 | Healthy | 2 |
| 1 | Breast | 57 |
| 2 | Breast | 33 |
| 3 | Breast | 43 |
| 4 | Breast | 40 |
| 5 | Breast | 6 |
| 1 | Lung | 3 |
| 2 | Lung | 125 |
| 3 | Lung | 38 |
| 4 | Lung | 17 |
| 5 | Lung | 7 |

Presence of isolated CTCs was determined by immunostaining with Hoechst (DNA), FITC-pan-cytokeratin (CK) antibodies (cancer/epithelial biomarker), and APC-anti-CD45 antibodies (hematologic biomarker) (see FIG. 36A). Hoechst+/pan-CK+/CD45− cells were scored as CTCs. Data presented in Table 1 demonstrates the clinico-pathological characteristics of the breast and lung cancer patients, as well as the CTC counts obtained from the spiral biochip. CTCs were detected in 10/10 patient samples (100% detection) with counts ranging from 6-57 CTCs/mL for MBC samples and 3-125 CTCs/mL for NSCLC samples (FIG. 36B). Epithelial cells positive for cytokeratin were also detected in healthy volunteers (1-4 per mL), but a distinct detection threshold can be drawn in comparison with that of patient samples. Threshold analysis demonstrated 3-4 CTCs per 7.5 mL of blood sample as the optimal cut-off value for predicting metastatic disease.

Figure 37:
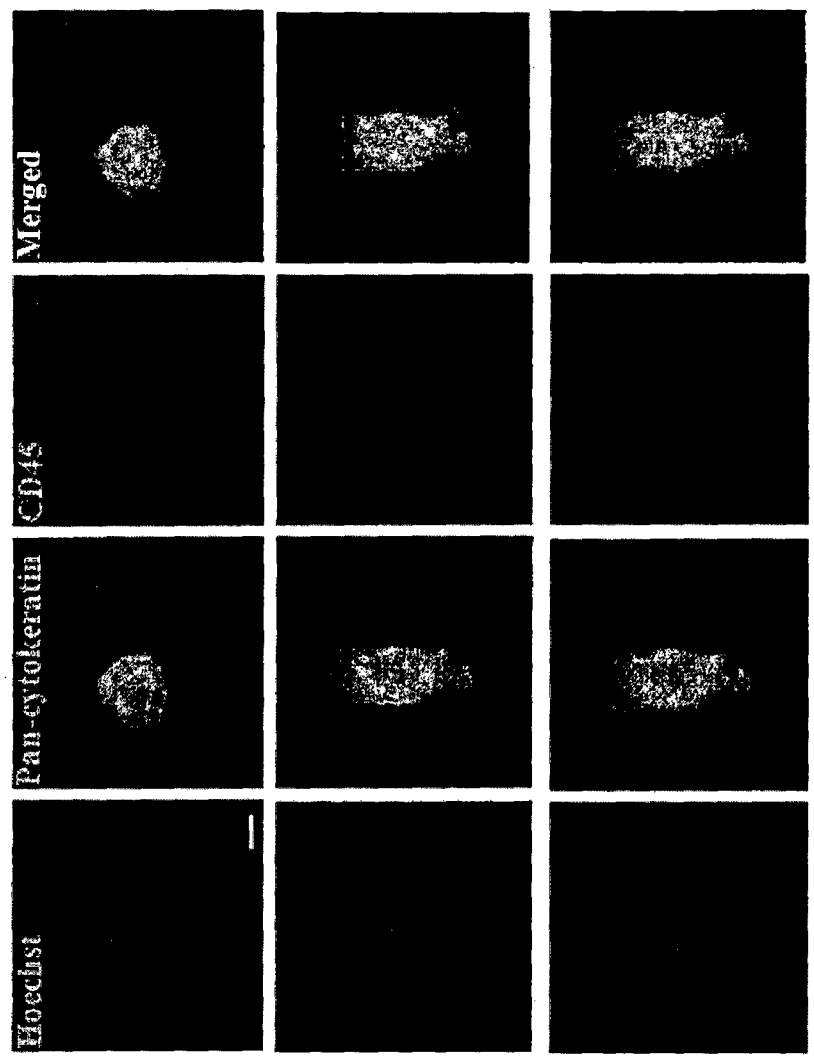
FIG. 37 are photographs of a library of CTC images displaying cell size and nuclei heterogeneity among them. The scale bar is 10 µm.
Figure 38:
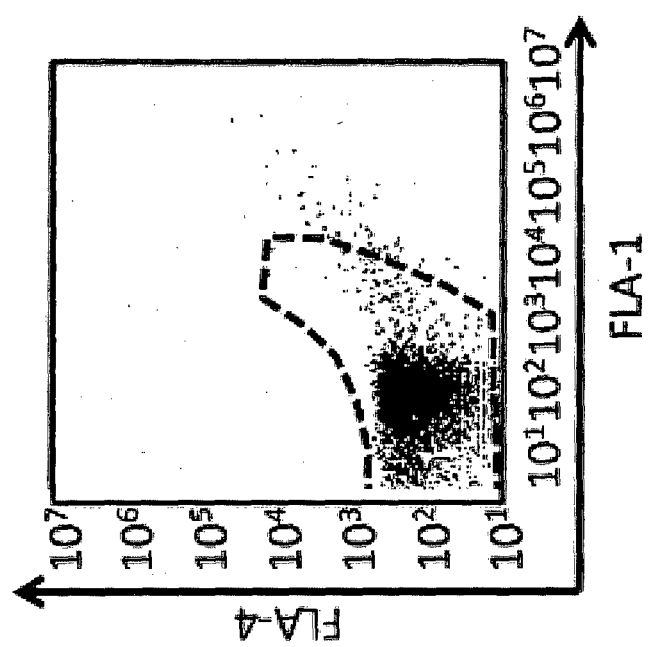
FIG. 38 is a graph of FLA-4 as a function of FLA-1 illustrating a flow cytometric analysis of isolated CTCs for cleaved caspase-3 protein. Only 9.9% of cells were positive for cleaved caspase-3, confirming that the high flow rates in the microfluidic chip do not affect cell viability and integrity.

Enriched CTCs are highly heterogeneous as previously reported in various studies (see FIG. 37). Staining of cancer stem cell markers CD44 and CD24 reveals distinct populations of CTCs which are mostly either CD44+/CD24− or CD44−/CD24+ (FIG. 36C). CD44+/CD24− cells are evidently larger in size than the CD44−/CD24+ cells. It should also be noted that a portion of CTCs are likely apoptotic. This is demonstrated by staining for cleaved caspase-3 marker which plays an integral role in the apoptotic process of mammalian cells. The results of the analysis showed that only 1-2% of isolated CTCs were positive for cleaved caspase-3, indicating that most of the CTCs enriched with the spiral biochip do not display characteristics that reflect the apoptotic processes. Flow cytometry analysis also revealed that only 9.9% of total isolated cells were positive for cleaved caspase-3, which could be most probably WBCs (FIG. 38). These findings were confirmed with immunofluorescence staining of the cells as shown in FIG. 36D, which was also in close agreement with previous findings. See T. J. Metzner, K. Bethel, E. H. Cho, M. S. Luttgen, D. C. Lazar, M. L. Uson, J. J. Nieva, L. Bazhenova, A. Kolatkar and P. Kuhnl, Cancer Res., 2012, 72, Supplement 1. In addition, the presence of EpCAM−/pan-CK+ cells and EpCAM+/pan-CK+ cells were detected in the isolated CTCs. The population of EpCAM−/pan-CK+ cells were much lower among lung cancer samples as compared to breast samples, indicating significant limitation of EpCAM based approaches for accurate detection and enrichment of putative CTCs. The ability to capture viable CTC is demonstrated by overnight culture of the isolated cells. In this study, isolated cells, shown in FIG. 35, were seeded onto polylysine coated well culture plates overnight under culture conditions as described above. Viable cells were able to spread onto the substrates and appeared negative for propidium iodide (PI) when stained.

FISH Analysis

Figure 39:
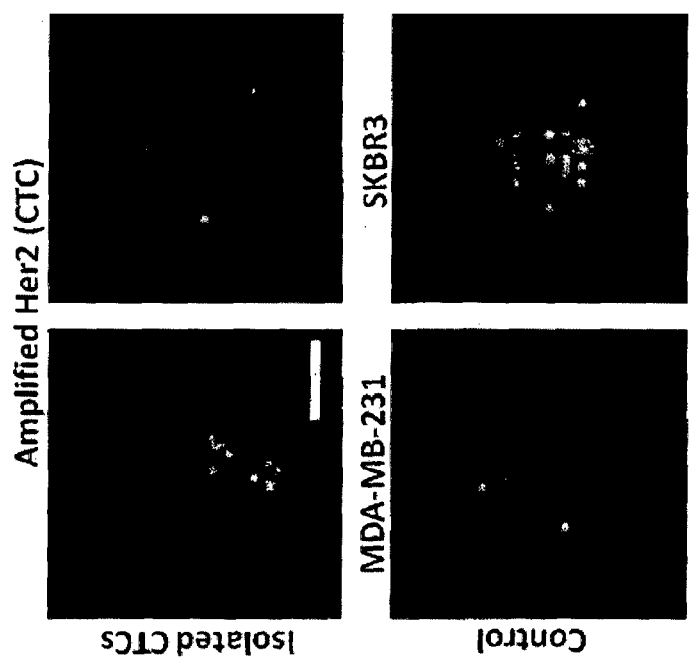
FIG. 39 are photographs illustrating the detection of Centromere of chromosome 17 (Cen-17) and HER2 of enriched CTCs. Cells were amplified for HER2 if HER2/Cen17 ratio is >2. MDA-MB-231 and SKBR3 breast cancer lines were used as controls. Merged images (DAPI, Spectrum: HER2 signal, Spectrum: Cen-17) are under 20× magnification. Scale bar: 10 µm.

Tumor cell heterogeneity in many different aspects has been apparent and widely reported previously. See A. A. Powell, A. H. Talasaz, H. Zhang, M. A. Coram, A. Reddy, G. Deng, M. L. Telli, R. H. Advani, R. W. Carlson and J. A. Mollick, PLoS One, 2012, 7, e33788. Herein, the variation of HER2 expression in CTCs isolated with the trapezoid chip is shown using samples from patients with HER2-tumors. Pantel et al. have shown that HER2 status in CTCs varies with respect to the primary tumor. See B. R. BAS Jaeger, U Andergassen, J K Neugebauer, C A Melcher, C Scholz, C Hagenbeck, K Schueller, R Lorenz, T Decker, G Heinrich, T Fehm, A Schneeweiss, W Lichtenegger, M W Beckmann, K Pantel, H L Sommer, K Friese, and W Janni, presented in part at the Thirty-Fifth Annual CTRC-AACR San Antonio Breast Cancer Symposium, San Antonio, Tex., 2012. Specifically, HER2+ CTCs may be observed in about 30% of samples obtained from HER2-origin. DNA fluorescence in-situ hybridization (FISH) was carried out to evaluate HER2 status in isolated CTCs. HER2 signals in isolated CTCs were compared against control breast cancer cell lines MDA-MB-231 (non-amplified HER2 signal) and SKBR3 (amplified HER2 signals) as shown in FIG. 39. Amplified HER2 expression is determined when the ratio of HER2/centromere of Chromosome 17 (Cen17) signals in single nuclei is >2. A range of HER2/Cen-17 signal was observed. Cells displaying a ratio of HER2/Cen-17=1 are likely to be WBC or non-amplified HER2 CTCs, and can be distinguished with further immunostaining. However, cells with amplified HER2 signals were also detected, indicating the definite presence of CTCs. This is in accordance with previous findings that heterogeneity of HER2 status is evident in CTC as compared to the primary tumor.

CONCLUSIONS

The "Holy Grail" of cancer medicine is the establishment of personalized therapies, where treatments shift from fixed regimes to therapies tailored to individual patients' tumor conditions. Circulating tumor cells have been shown to be a good alternative to primary tumor biopsies, carrying similar genetic information. Detection of CTCs in the peripheral blood of cancer patients at different disease stages has shown promise as a prognostic marker for treatment efficacy and patient survival, indicating strong clinical relevance. However, systematic characterization of CTCs in vitro via downstream assays has been delayed by the lack of reliable and sensitive methods to detect and enrich these cells. Despite the rapid advancement in microfluidic technologies, the isolation of CTCs with high throughput, high purity and high cell viability remains elusive. The application of a novel microfluidic platform for ultra-fast enrichment of putative CTCs using inertial microfluidics in spiral microchannels with trapezoidal cross-section is demonstrated herein. This improved device achieved higher (blood) volume processing, and increased CTC capture efficiency and yield. In addition to the rapid blood processing speed of 1.7 mL/min, the simple yet efficient trapezoidal spiral channels greatly facilitate scaled-up device production, and will thus enable larger-scale clinical studies. As described above, the trapezoidal spiral biochip successfully isolated CTCs from 10 out of 10 (100%) patients with advanced stage metastatic breast and lung cancer (3-125 CTCs/mL) and allowed extensive heterogeneity studies via immunostaining and DNA FISH analysis. Viability of isolated CTCs was also retained after processing which will allow potential culture and expansion studies. The majority of isolated CTCs from peripheral blood of breast cancer patients are viable but non-proliferative after days in culture, suggesting the requirement of new therapeutic approaches that targets cells in dormancy. In addition, the continuous collection of CTCs facilitates coupling of the device with conventional 96-well plate or a membrane filter for subsequent downstream analysis such as immunostaining, qRT-PCR, FISH and sequencing.

The precision and recovery rates at low cell spiking levels given by the inertial microfluidic system were high. Because this approach does not require initial cell surface biomarker selection, it is suitable for use in different cancers of both epithelial and non-epithelial origin. CTCs are reported to be highly heterogeneous and variable in EpCAM and cytokeratin expression, biomarkers used for CTC enrichment in many microfluidic devices. The selection criteria of cell size will overcome this limitation and capture a wider proportion of CTCs. Cells with lower expression of specific cytokeratins will still be identified with immunostaining due to the use of pan-cytokeratin antibodies. The sensitivity of the system was analyzed by determining the recovery rate of GFP-tagged breast (MCF-7 and MDA-MB-231) and bladder (T24) cancer cell lines spiked into blood obtained from healthy volunteers at the concentration of 500 cells/7.5 mL of blood. General limitations of various model systems are as described by Ring et al. See A. Ring, I. E. Smith and M. Dowsett, Lancet Oncol., 2004, 5, 79-88. Capture efficiency of cancer cells was high, ranging from 80-90%. This variability can partly be attributed to the differences in cell size between cancer types. Nevertheless, the flexibility and simplicity of the system allows for maximum cell isolation from different cancer types by moderate alterations of the channel design. The results demonstrate the versatility of the system for enriching CTCs of different cancer types, thus acting as a potential tool for the continuous assessment of CTCs and reliable CTC count detection in patients. The system is further validated by clinical trials on 10 blood samples from advanced stage metastatic breast and lung cancer. CTCs are detected in 10/10 samples, which clearly demonstrated the sensitivity of the system. However, inter-patient variability is observed, a trend reported previously. See M. Cristofanilli, T. Budd, M. J. Ellis, A. Stopeck, J. Matera, M. C. Miller, J. M. Reuben, G. V. Doyle, J. Allard, L. W. M. M. Terstappen and D. F. Hayes, N. Engl. J. Med., 2004, 351, 781-791; W. J. Allard, J. Matera, M. C. Miller, M. Repollet, M. C. Connelly, C. Rao, A. G. J. Tibbe, J. W. Uhr and L. W. M. M. Terstappen, Clin. Cancer Res., 2004, 10, 6897. This variability does not reflect the analytic performance of the system; rather it depends on various factors such as the stage of the disease and patient conditions that may affect on the number of CTCs present in the blood.

The application of standard histopathology and immunostaining procedures are essential to the understanding of the role of CTCs in cancer metastasis and potential drug treatment. To date, very low CTC counts were isolated by commercial platforms, limiting these downstream procedures. Improvement of CTC isolation will facilitate the use of standardized procedures for characterization, such as cytological examination by Papanicolaou (PAP) stains and DNA FISH. CTCs isolated with the trapezoidal spiral biochip were treated by PAP stain and revealed high nuclear to cytoplasmic (N/C) ratio, which is characteristic of cancer cells. Some CTCs are HER2+ when treated by respective DNA FISH probes. The presence of HER2+ CTCs varies across samples and is also observed in samples derived from patients with HER2-tumors (2 out of 5). This supports previous finding that heterogeneity of HER2 status is evident in CTC as compared to the primary tumor. See S. Riethdorf, H. Fritsche; V. Mülller, T. Rau2, C. Schindlbeck, W. J. Brigitte Rack, C. Coith, K. Beck, F. Jänicke, S. Jackson, T. Gornet, M. Cristofanilli and K. Pantel, Clin. Cancer Res., 2007, 13, 920. Detection of HER2 amplification in CTCs may identify high-risk breast cancer patients who may benefit from HER2 associated therapeutic strategies. In conclusion, this study shows the examination of blood samples for CTCs with the inertial microfluidic system.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A micro-fluidic device that can preferentially generate at least one strong Dean vortex along a flow stream for at least one of particle trapping and cell trapping, the micro-fluidic device comprising:
   i) at least one inlet;
   ii) a curvilinear microchannel having a cross section defined by a constant width along the microchannel, and a radially inner side, a radially outer side, a bottom side, and a top side, the cross section having the radially inner side and the radially outer side unequal in height, resulting in the generation of at least one strong Dean vortex core, a channel depth of the radially outer side being between about 100 µm and about 140 µm, and a channel depth of the radially inner side being between about 70 µm and about 90 µm;
   the curvilinear microchannel being configured to trap at least one of a particle and a cell in the at least one strong Dean vortex along the radially outer side of the curvilinear microchannel; and
   iii) at least one outlet.

2. The micro-fluidic device of claim 1, wherein the top side includes at least one step forming a stepped profile.

3. The micro-fluidic device of claim 1, wherein the cross section is a right trapezoidal cross section.

4. The micro-fluidic device of claim 1, wherein the top side or bottom side of the cross section is curved.

5. The micro-fluidic device of claim 4, wherein the top side or the bottom side of the cross section is convex or concave.

6. The micro-fluidic device of claim 1, wherein the top side or bottom side of the cross section has a width in a range of between about 100 microns and about 2000 microns.

7. The micro-fluidic device of claim 1, wherein the curvilinear microchannel is a spiral microchannel or a serpentine microchannel.

8. The micro-fluidic device of claim 1, wherein the curvilinear microchannel has a radius of curvature in a range of between about 2.5 mm and about 25 mm.

9. The micro-fluidic device of claim 1, wherein the curvilinear microchannel has a length in a range of between about 4 cm and about 100 cm.

10. The micro-fluidic device of claim 1, wherein the cross section is a right trapezoidal cross section comprising a slant angle of between about 2 degrees and about 60 degrees.

11. A method of separating by size one or more particles from a mixture of particles suspended in a liquid media, comprising introducing the mixture into at least one inlet of a micro-fluidic device that can preferentially generate at least one strong Dean vortex along a flow stream for particle trapping, the micro-fluidic device comprising:
   i) at least one inlet;
   ii) a curvilinear microchannel having a cross section defined by a constant width along the microchannel, and a radially inner side, a radially outer side, a bottom side, and a top side, the cross section having the height of the radially inner side being smaller than the height of the radially outer side, resulting in the generation of at least one strong Dean vortex core, a channel depth of the radially outer side being between about 100 µm and about 140 µm, and a channel depth of the radially inner side being between about 70 µm and about 90 µm;
   the curvilinear microchannel being configured to trap at least one of a particle and a cell in the at least one strong Dean vortex along the radially outer side of the curvilinear microchannel; and
   iii) at least one outlet;
   the mixture being introduced into the at least one inlet of the micro-fluidic device at a flow rate that isolates particles along portions of the cross-section of the microchannel based on particle size, wherein larger particles flow along the radially inner side of the microchannel to a first outlet and smaller particles are trapped in at least one strong Dean vortex core near the radially outer side and flow to at least one other outlet, thereby size separating the particles from the mixture.

12. The method of claim 11, wherein the particles are cells or a mixture of cells.

13. The method of claim 12, wherein the cells are stem cells; the mixture of cells is a blood sample; the mixture of cells is a bone marrow sample; the mixture of cells are stem cells and hematologic cells; the mixture of cells are CTC's and hematologic cells; or the mixture of cells are leukocytes and hematologic cells.

14. A method of mixing cells in a liquid, comprising introducing a liquid and cells into at least one inlet of a micro-fluidic device, the micro-fluidic device comprising:
   i) at least one inlet;
   ii) a curvilinear microchannel having a cross section defined by a constant width along the microchannel, and a radially inner side, a radially outer side, a bottom side, and a top side, the cross section having the radially inner side equal in height to the radially outer side, and wherein the top side has at least two continuous straight sections, each unequal in width to the bottom side, the top side including at least one shallow region, between the radially inner side and the radially outer side, that is shallower than both a channel depth of the radially inner side and a channel depth of the radially outer side; and
   iii) at least one outlet;
   the introducing the liquid and the cells into the at least one inlet of the micro-fluidic device being at a flow rate that mixes cells along the microchannel and directs the mixture to a first outlet and optionally collecting the mixture from the first outlet.

15. A micro-fluidic device for mixing cells in a liquid, the micro-fluidic device comprising:
   i) at least one inlet;
   ii) a curvilinear microchannel having a cross section defined by a constant width along the microchannel, and a radially inner side, a radially outer side, a bottom side, and a top side, the cross section having the radially inner side equal in height to the radially outer side, wherein the top side has at least two continuous straight sections, each unequal in width to the bottom side, and wherein the top side includes at least one shallow region, between the radially inner side and the radially outer side, that is shallower than both a channel depth of the radially inner side and a channel depth of the radially outer side; and
   iii) at least one outlet.

* * * * *